United States Patent [19]

Ishida et al.

[11] Patent Number: 5,017,212
[45] Date of Patent: May 21, 1991

[54] SULFONYLUREA COMPOUNDS AND HERBICIDAL USE

[75] Inventors: Yasuo Ishida, Suita; Kazunari Ohta, Ashiya; Tatsuo Nakahama, Akashi; Harutoshi Yoshikawa, Yawata, all of Japan

[73] Assignee: Takeda Chemical Industries, Ltd., Osaka, Japan

[21] Appl. No.: 26,989

[22] Filed: Mar. 17, 1987

[30] Foreign Application Priority Data

Mar. 20, 1986 [JP] Japan .................. 61-63740
Dec. 23, 1986 [JP] Japan .................. 61-311419

[51] Int. Cl.⁵ .................. A01N 43/54; C07D 401/14; C07D 403/14; C07D 413/14

[52] U.S. Cl. .................. 71/92; 71/93; 71/90; 71/91; 544/295; 544/296; 544/320; 544/321; 544/281; 544/184; 544/331; 544/332; 544/212; 544/179; 544/91; 544/48; 544/10; 544/282; 544/238; 544/279; 544/236; 544/235

[58] Field of Search .................. 71/92, 90, 91, 93; 544/331, 332, 295, 321, 212, 48, 238, 235

[56] References Cited

U.S. PATENT DOCUMENTS 4,678,499 7/1987 Pasteris et al. .................. 71/90

4,681,620 7/1987 Bohner et al. .................. 71/93

FOREIGN PATENT DOCUMENTS 96003 12/1983 European Pat. Off. .
152286 8/1985 European Pat. Off. .
168264 1/1986 European Pat. Off. .
203679 12/1986 European Pat. Off. .
60-208977 10/1985 Japan .
61-37782 2/1986 Japan .

*Primary Examiner*—John M. Ford
*Attorney, Agent, or Firm*—Wenderoth, Lind & Ponack

[57] ABSTRACT

A compound of the general formula:

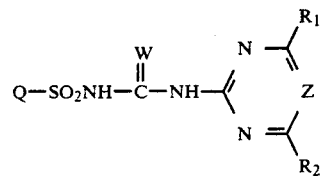

wherein Q is a condensed heterocyclic group having an N atom in the bridgehead which may be substituted, W is O or S, $R_1$ and $R_2$ each are an alkyl group, an alkoxy group or halogen and Z is CH or N, and a salt thereof, which is useful as a herbicide.

22 Claims, No Drawings

SULFONYLUREA COMPOUNDS AND HERBICIDAL USE

This invention relates to new condensed heterocyclic sulfonylurea compounds, their production and herbicidal use.

The condensed heterocyclic sulfonylurea compounds (the compounds of the general formula (I) mentioned below and salts thereof) according to this invention have an excellent herbicidal effect on paddy weeds and field weeds and no substantial damage on crops such as rice, wheat, barley, corn, soy bean, etc., and can be used as an excellent selective herbicide in a paddy and field.

Hitherto, various sulfonylurea derivatives having herbicidal property have been reported. For example, Japanese Unexamined Patent Publication Nos. 37,782/1986 and 208,977/1985 and EP-A-96,003 describe sulfonylurea derivatives represented by the general formula:

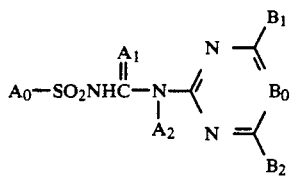

in which $A_0$ is a 5-membered heterocyclic group such as pyrazolyl or imidazolyl; $A_1$ is oxygen or sulfur; $A_2$ is hydrogen or a $C_{1-5}$ alkyl group; $B_0$ is CH or N; $B_1$ and $B_2$ each are hydrogen, a lower alkyl group, etc. The substituent $A_0$ on sulfonyl group of the above mentioned sulfonylurea however is a 5-membered heterocyclic group such as pyrazolyl which is quite different from a condensed heterocyclic group having an N atom in the bridgehead of the compound of this invention. In addition, the above mentioned sulfonylurea derivatives are not satisfactory with respect to herbicidal effect and damage on crops. Further, EP-A-152,286 discloses pyrazolylsulfonyls represented by the formula:

$$L_0-SO_2NHC(=O)-N(L_2)-L_1 \text{ in which } L_0 \text{ is}$$

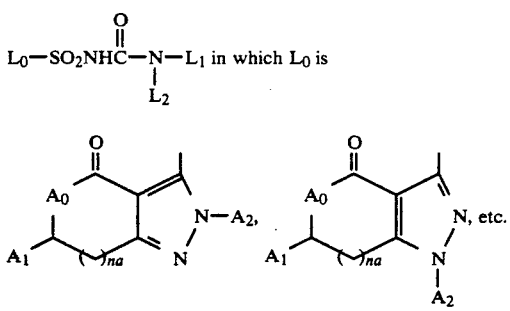

($A_0$ is oxygen, sulfur, etc; $A_1$ is hydrogen or a $C_{1-3}$ alkyl group; $A_2$ is hydrogen atom, a $C_{1-3}$ alkyl group, etc; na is 0 or 1); $L_1$ is

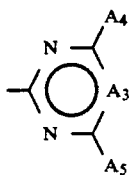

$A_3$ is CH or N; $A_4$ is methyl, methoxy, etc; $A_5$ is hydrogen or a $C_{1-3}$ alkyl group), and $L_2$ is hydrogen or methyl. Such pyrazolylsulfonylureas also are different from the compounds of this invention on the point of structure, because the condensed pyrazolyl group which is the substituent on the sulfonyl group in the above mentioned pyrazolylsulfonylureas does not possess an N atom in the bridgehead. Moreover, when used as herbicide, the above mentioned pyrazolylsulfonylureas are not satisfactory with respect to herbicidal effect, damage on crops (e.g., rice) or the like.

The inventors of this invention have made investigation after investigation with a view to developing selective herbicides having excellent herbicidal activity and no damage on crops, and found that the compounds of the below-mentioned general formula (I) and their salts have a strong herbicidal activity and a remarkably reduced damage on crops such as rice, wheat, barley, corn, soy bean and the like, and accordingly exhibit a highly selective herbicidal effect. On the basis of such findings, the inventors have made various further investigations and completed the present invention.

According to the invention, it provides (1) a compound having the general formula:

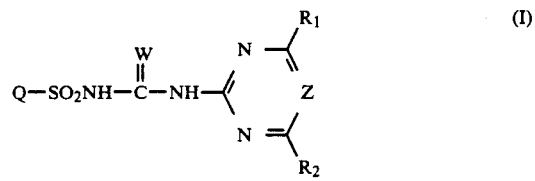

wherein Q is a condensed heterocyclic group having an N atom in the bridgehead which may be substituted; W is O or S; $R_1$ and $R_2$ each are an alkyl group, an alkoxy group or a halogen and Z is CH or N, or a salt thereof;

(2) a process for the production of the compound (I) or salt thereof which comprises reacting a compound of the general formula:

$$Q-SO_2X \quad (II)$$

or salt thereof, with a compound of the general formula:

or salt thereof, wherein either of X or Y is amino group and the other is a group of the formula

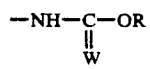

W is O or S and R is a hydrocarbon residue) or a group of the formula —N=C=W (W has the same meaning as described above), and the other symbols have the same meanings as described above;

(3) a process for the production of a compound of the general formula:

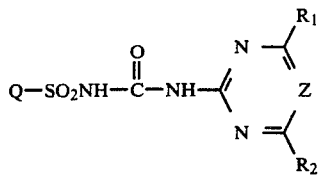 (I')

wherein the symbols have the same meanings as described above, or salt thereof which comprises reacting a compound of the general formula:

Q—H  (IV), wherein Q has the same meaning as described above, or salt thereof, with a compound of the general formula:

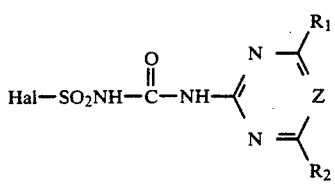 (V)

wherein Hal is a halogen e.g., fluorine, chlorine or bromine) and the other the same meanings as described above; and (4) a herbicidal composition comprising the compound (I) or salt thereof.

In the above mentioned general formulae, Q is a condensed heterocyclic group having an N atom in the bridgehead which may be substituted. The condensed heterocyclic group having an N atom in the bridgehead means a condensed heterocylic group in which the atom(s) at the head or end of the bridgehead, i.e., both or either one of the bridgehead atoms are nitrogen atom(s). The condensed heterocyclic group having an N atom in the bridgehead which may be substituted and which is represented by the symbol Q is, for example, the group which is formed from a condensed heterocyclic ring by the general formula:

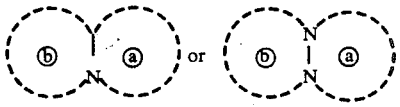

(wherein the rings a and b are a nitrogen-containing heterocyclic ring which may be substituted) by removing one hydrogen atom bonded to a ring-constituting carbon atom at a position other than the bridgehead. Examples of such condensed heterocyclic groups are those of the general formula:

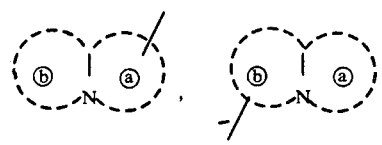

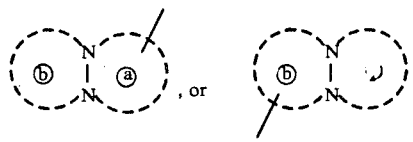

wherein—is a bonding arm, and the other symbols are as defined above.

The nitrogen containing heterocyclic ring of the ring ⓐ or the ring ⓑ means a 4 to 8 (preferably 5 or 6) membered heterocyclic ring including the bridgehead atoms and containing 1 to 4 nitrogen atoms and optionally, 1 to 3 oxygen atoms and/or 1 to 3 sulfur atoms (which may be in mono- or di-oxide form) which may be condensed with a 5 or 6 membered alicyclic ring (e.g., cyclopentane or cyclohexane), an aromatic ring (e.g., benzene or naphthalene) or a heterocyclic ring (preferably a 5 to 6 membered heterocyclic ring containing 1 to 4 hetero atoms such as nitrogen (which may be oxidized), oxygen or sulfur (which may be oxidized). The preferred one is a group of the formula:

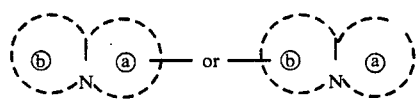

In the above formula, the ring ⓐ is preferred to be a 5 membered heterocyclic ring containing 1 to 3 nitrogen atoms and the ring ⓑ is preferred to be a 6 membered heterocyclic ring containing 1 to 2 nitrogen atoms or a 5 membered heterocyclic ring containing 1 to 2 nitrogen atoms and one sulfur atom (which may be in mono- or di-oxiodized form).

The rings a and b may be substituted by the same or different one to three substituents of $B_1$, $B_2$ and $B_3$ as defined later. Specifically, the group of

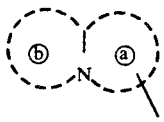

is

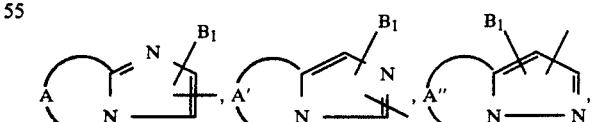

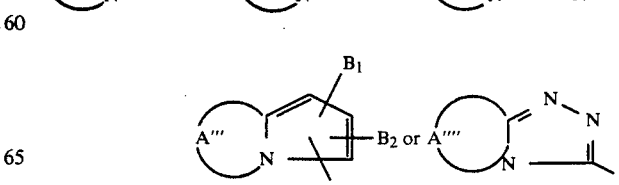

and the group of

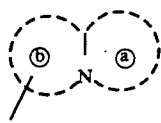

is

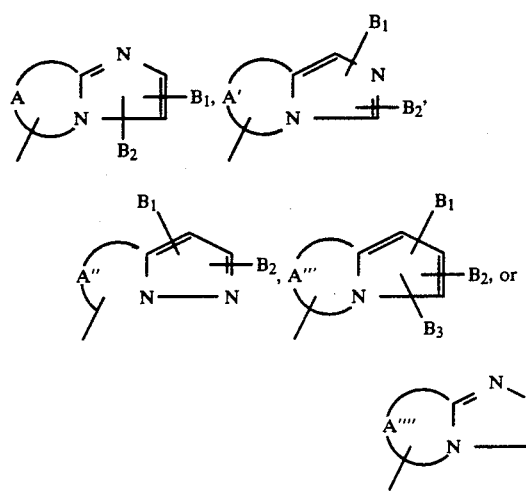

wherein A is a group which forms a condensed ring at the [1,2]position of the imidazole ring A, is a group which forms a condensed ring at the [1,5]position of the imidazole ring, A" is a group which forms a condensed ring at the [1,5]position of the pyrazole ring, A''' is a group which forms a condensed ring a the [1,2]position of the pyrrole ring, A'''' is a group which forms a condensed ring at the [3,4]position of the triazole ring, and $B_1$, $B_2$ and $B_3$ each are hydrogen, hydroxy, amino, cyano, sulfamoyl, sulfamoyloxy, mercapto, nitro, a halogen or an organic residue. The carbon atom or nitrogen atom constituting a ring atom in the group A, A', A", A''' or A'''' may be substituted by the same or different 1 to 3 substituents suitably such as hydroxy, amino, cyano, sulfamoyl, sulfamoyloxy, mercapto, nitro, a halogen, an organic residue or sulfo. The carbon atom and nitrogen atom, or the carbon atom and carbon atom which are adjacent to each other, and which constitute a ring atom in the group A, A', A", A''' or A'''' may form another condensed ring (5 or 6 membered condensed ring). The ring-constituting sulfur atom may be in mono or di-oxide form.

The organic residue of $B_1$, $B_2$ or $B_3$ has the same meaning as that of the substituent on the condensed heterocyclic ring which is defined below.

The group A, A', A", A''' or A'''' contains 1 to 4, preferably 3 or 4 of carbon atoms as the ring-constituting atom and may further contain 1 to 3 of nitrogen atom, oxygen atom and/or sulfur atoms (may be in mono- or di-oxide form).

Examples of the condensed rings represented by

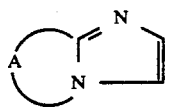

as the skelton of the group of the general formula:

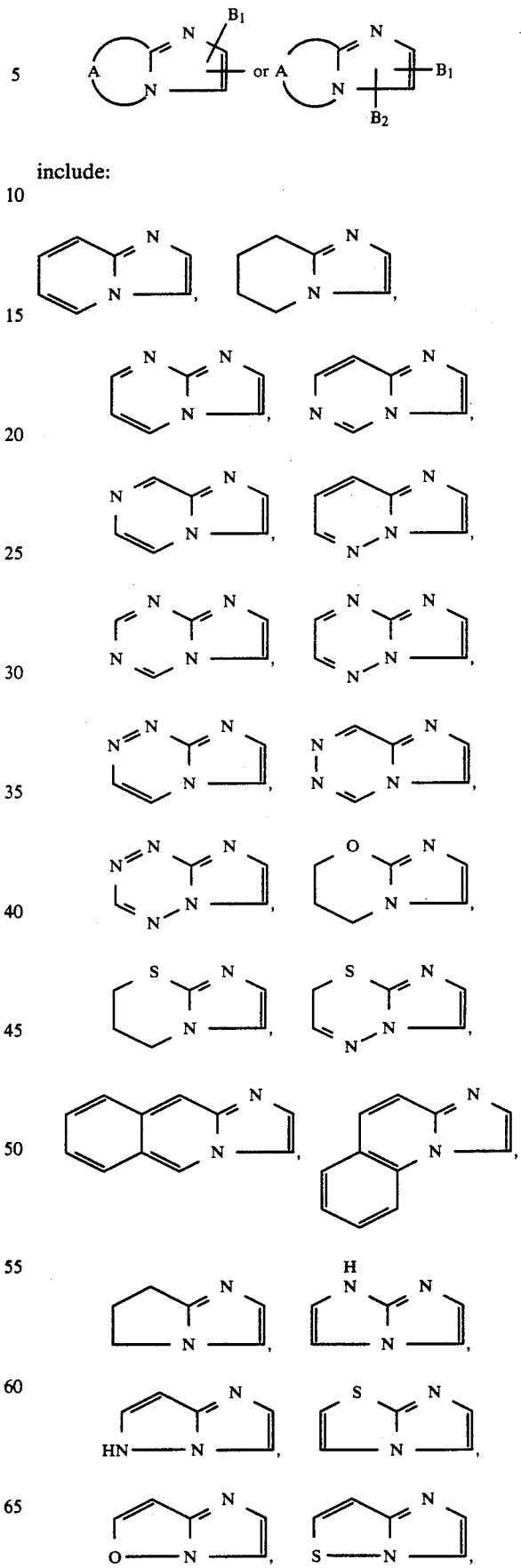

include:

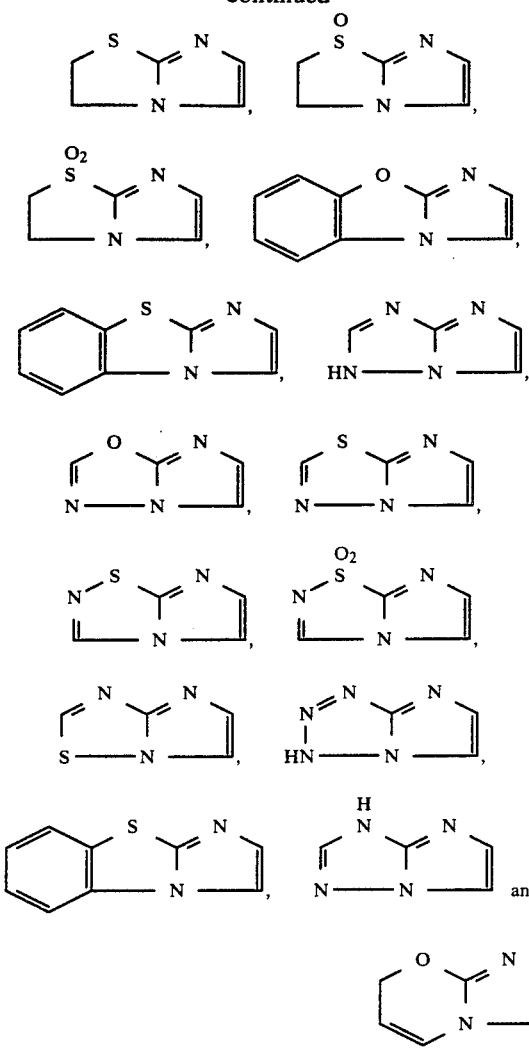
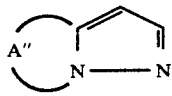
Examples of the condensed rings represented by
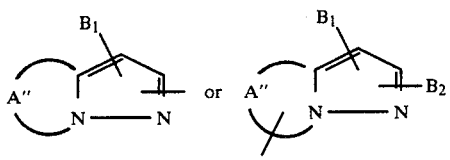
as the skelton of the group of the general formula:
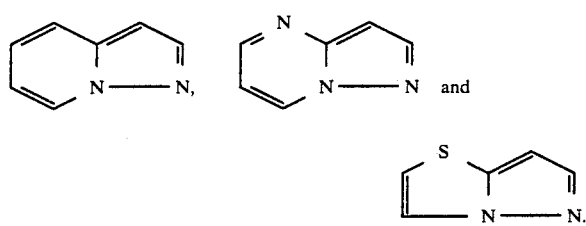
are:
Examples of the condensed rings represented by
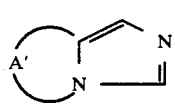
as the skelton of the group of the general formula:
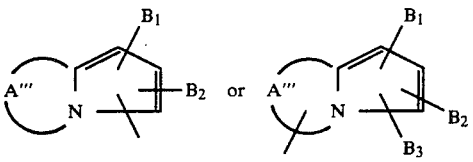
are:
Examples of the condensed rings represented by
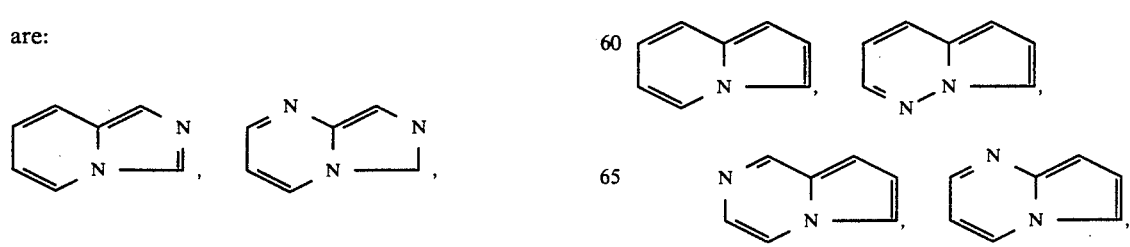
as the skelton of the group of the general formula:

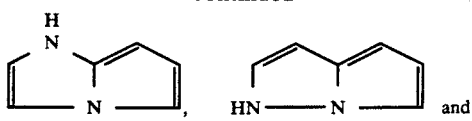

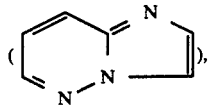 and

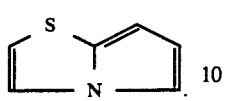

Examples of the condensed rings represented by

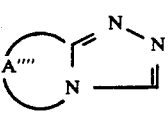

as the skelton of the group of the general formula:

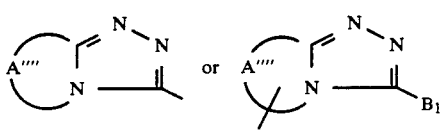

are:

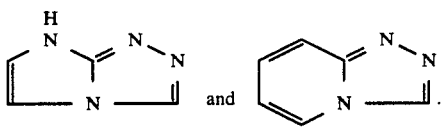

Preferred ones of these heterocyclic rings are imidazo[1,2-a]pyridine

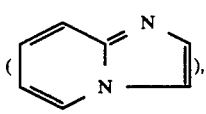

imidazo[2,1-b]thiazole

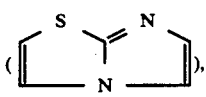

imidazo[1,2-a]pyrimidine

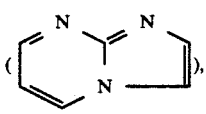

imidazo[1,2-b]pyridazine

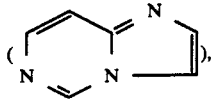

imidazo[1,2-c]pyrimidine

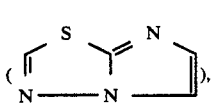

imidazo[1,2-a]imidazole

imidazo[2,1-b](1,3,4)thiadiazole 2,3-dihydroimidazo[2,1-b]thiazole

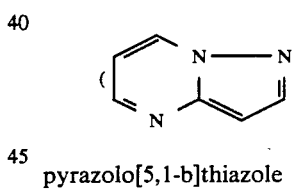

(or its mono- or di-oxide form) (n is 0,1 or 2), pyrazolo[1,5-a]pyrimidine pyrazolo[5,1-b]thiazole pyrazolo[1,5-a]pyridine pyrrolo[1,2-a]pyridine imidazo[1,5-a]pyridine

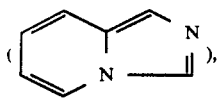

imidazo[1,2-b]triazole

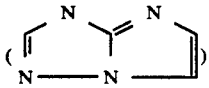

and (1,2,4) triazolo[3,4-b]thiazole

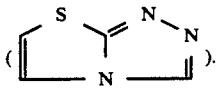

The more preferred ones are imidazo[1,2-a]pyridine, imidazo[2,1-b]thiazole and imidazo[1,2-b]pyridazine.

As stated above, the condensed heterocyclic group having an N atom in the bridgehead for Q is the group which is formed from a condensed heterocyclic ring by removing one hydrogen atom bonded to a ring-constituting carbon atom at a position other than the bridgehead. For example, the condensed heterocyclic groups corresponding to imidazo[1,2-a]pyridine as a condensed heterocycle are:

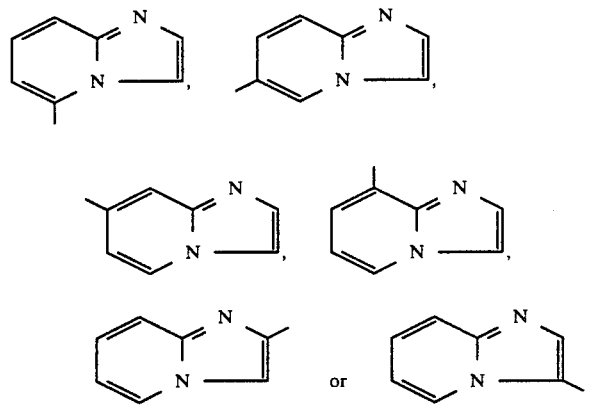

The suitable ones of the above mentioned groups are of the general formula:

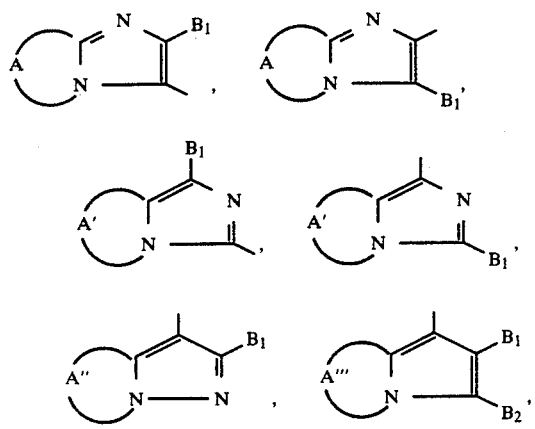

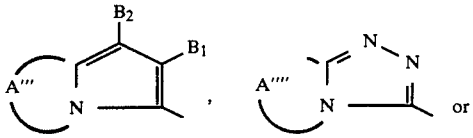

In the group A, the ring-constituting atoms comprise preferably four carbon atoms; two or three carbon atoms and one nitrogen atom; two carbon atoms and one sulfur atom (which may be in mono- or di-oxide form); each one of carbon atom, sulfur atom and nitrogen atom; or one carbon atom and two nitrogen atoms.

In the groups A' and A''', the ring-constituting atoms comprise preferably four carbon atoms.

In the group A'', the ring-constituting atoms comprise preferably four carbon atoms; three carbon atoms; one nitrogen atom; and two carbon atoms and one sulfur atom.

In the group A'''', the ring-constituting atoms comprise preferably two carbon atoms and one sulfur atom.

The condensed heterocyclic group having an N atom in the bridgehead may be sutstituted by one to three substituents, the same or different, such as hydroxy, amino, cyano, sulfamoyl, sulfamoyloxy, mercapto, nitro, a halogen, an organic residue or sulfo, as mentioned above.

The preferred substituents are cyano, sulfamoyl, sulfamoyloxy, nitro, a halogen or an organic residue and the more preferred ones are cyano, a halogen or organic residue.

The halogen atom used here is, for example, fluorine, chlorine, bromine or iodine.

The organic residue is, for example, a hydrocarbon residue, a heterocyclic group, an acyl group, a group of the formula - T - $Q_0$ ($Q_0$ is a hydrocarbon residue, a heterocyclic group or an acyl group and T is O, S-(O)$_n$ or S-S, n being 0,1 or 2), a group of the formula

$Q_1$ is hydrogen, a hydrocarbon residue or an acyl group and $Q_2$ is a hydrocarbon residue or an acyl group), a group of the formula

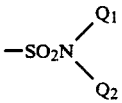

($Q_1$ and $Q_2$ have the same meanings as mentioned above), carbamoyl, carbamoyloxy, ureido, thiocarbamoyl, carboxyl, a group of the formula —O—SO$_2$—Q$_2$ ($Q_2$ has the same meaning as mentioned above), or the like.

The above-mentioned hydrocarbon residue, heterocyclic group and acyl group as the example of the organic residue; the hydrocarbon residue, heterocyclic group and acyl group of $Q_0$; and the hydrocarbon residue and acyl group of $Q_1$ or $Q_2$ are in detail explained below.

The above-mentioned carbamoyl group, carbamoyloxy group, ureido group and thiocarbamoyl group may be substituted by the same or different 1 or 2 substituents of the below-mentioned hydrocarbon residue, heterocyclic group and acyl group.

The heterocyclic group as the example of the organic residue and in $Q_0$ may be substituted by one to three of such below-mentioned hydrocarbon residue, acyl group and halogen atom.

Examples of the above-mentioned hydrocarbon residues include a straight chain, branched chain or cyclic aliphatic group which may have one or more double or triple bonds, or an aryl or aralkyl group, more concretely, an alkyl, alkenyl, alkynyl, aryl or aralkyl group. The alkyl group is preferably a straight chain, branched chain or cyclic alkyl group containing 1 to 6 carbon atoms, such as methyl, ethyl, n-propyl, isopropyl, n-butyl, isobutyl, sec-butyl, tert-butyl, n-pentyl, sec-pentyl, isopentyl, neopentyl, cyclopentyl, n-hexyl, isohexyl or cyclohexyl. The alkenyl group is preferably a straight chain, branched chain or cyclic alkenyl group containing 3 to 6 carbon atoms, such as allyl, isopropenyl, 1-butenyl, 2-pentenyl or 2-hexenyl. The alkynyl group is preferably an alkynyl group containing 3 to 6 carbon atoms, such as propargyl, 2-butynyl, 3-butynyl, 3-pentynyl or 3-hexynyl. The aryl group is preferably an aryl group containing 6 to 14 carbon atoms, such as phenyl, naphthyl, biphenylyl or anthryl. The aralkyl group is preferably an aralkyl group containing 7 to 19 carbon atoms, such as benzyl, phenethyl, phenylpropyl, biphenylylmethyl, benzhydryl or trityl.

The above-mentioned heterocyclic group is, for example, a 5 or 6 membered heterocyclic group containing 1 to 4 hetero atoms such as nitrogen atom (which any be oxidized), oxygen atom or sulfur atom (which may be oxidized), or a condensed ring group thereof, preferably a condensed ring group of said 5 or 6 membered heterocyclic group which may contain 1 to 4 hetero atoms of nitrogen atom (which may be oxidized)-,oxygen atom or sulfur atom (which may be oxidized), specifically, 2- or 3-pyrrolyl, 3-, 4- or 5-pyrazolyl, 2-, 4- or 5-imidazolyl, 1,2,3-triazol-4-yl, 1,2,4-triazol-3-yl, 1H- or 2H-tetrazol-5-yl, 2- or 3-furyl, 2- or 3-thienyl, 2- or 3-thienyl-1,1-dioxide, 2-,4- or 5-oxazolyl, 3-,4- or 5-isoxazolyl, 1,2,3-oxadiazol-4 or 5-yl, 1,2,4-oxadiazol-3 or 5-yl, 1,2,5-oxadiazol-3 or 4-yl, 1,3,4-oxadiazol-2 or 5-yl 2-,4- or 5-thiazolyl, 3-,4- or 5-isothiazolyl, 1,2,3-thiadiazol-4 or 5-yl, 1,2,4-thiadiazol-3 or 5-yl, 1,2,5-thiadiazol-3 or 4-yl, 1,3,4-thiazol-2 or 5-yl 2- or 3-pyrrolidinyl, 2-,3- or 4-pyridyl, 2-,3- or 4-pyridyl-N-oxide, 3- or 4-pyridazinyl, 3- or 4-pyridazinyl-N-oxide, 2-,4- or 5-pyrimidinyl, 2-,4- or 5-pyrimidinyl-N-oxide, pyrazinyl,2-,3- or 4-piperidinyl, piperazinyl, 3H-indol-2 or 3-yl, 2-,3- or 4-pyranyl, 2-,3- or 4-thiopyranyl, 2-,3- or 4-thiopyranyl-1,1-dioxide, benzopyranyl, quinolyl, pyrido 2,3-d pyrimidnyl (e.g., pyrido[2,3-d]pyrimidin-2-yl), 1,5-, 1,6-, 1,7-, 1,8-, 2,6- or 2,7-naphthyridinyl (e.g., 1,5-naphthyridin-2 or 3-yl), thieno[2,3-d]pyridyl (e.g., thieno[2,3-d]pyridin-3-yl) pyrazinoquinolyl (e.g., pyrazino[2,3-d]quinolin-2-yl) or chromenyl (e.g., 2H-chromen-2 or 3-yl).

The above-mentioned acyl group is an acyl group derived from an organic carboxylic acid, such as an alkanoyl group preferably containing 1 to 7 carbon atoms (for example, formyl, acetyl, propionyl, butyryl, isobutyryl, pentanoyl, hexanoyl or heptanoyl), an arylcarbonyl group preferably containing 6 to 14 carbon atoms (for example, benzoyl or naphthalenecarbonyl), an alkoxycarbonyl group preferably containing 1 to 6 carbon atoms (for example, ethoxycarbonyl, ethoxycarbonyl, propoxycarbonyl, isopropoxycarbonyl, butoxycarbonyl, isobutoxycarbonyl, sec-butoxycarbonyl or tert-butoxycarbonyl), an aryloxy carbonyl group preferably containing 6 to 14 carbon atoms (for example, phenoxycarbonyl), an aralkylcarbonyl group preferably containing 7 to 19 carbon atoms (for example, benzylcarbonyl, phenethylcarbonyl, phenylpropylcarbonyl, benzhydrylcarbonyl or naphthylethylcarbonyl), a 5 or 6 membered heterocycle-carbonyl group preferably containing 1 to 4 hetero atoms such as nitrogen atom (which may be oxidized), oxygen atom or sulfur atom (which may be oxidized) in the heterocycle, such as, 2-,3- or 4-pyrrolylccarbonyl, 3-,4- or 5-pyrazolylcarbonyl, 2-,4- or 5-imidazolylcarbonyl, 1,2,3-triazol-4-ylcarbonyl or 1,2,4-triazol-3-ylcarbonyl, 1H- or 2H-tetrazol-5-ylcarbonyl, 2- or 3-furylcarbonyl, 2- or 3-thienylcarbonyl, 2-,4- or 5-oxazolylcarbonyl, 3-,4- or 5-isoxazolylcarbonyl, 1,2,3-oxadiazol-4 or 5-ylcarbonyl, 1,2,4-oxadiazol-3 or 5-ylcarbonyl, 1,2,5-oxadiazolyl-3 or 4-carbonyl, 1,2,4-oxadiazol-2- or 5-ylcarbonyl, 2-,4- or 5-thiazolylcarbonyl, 3-,4- or 5-isothiazolylcarbonyl, 1,2,3-thiadiazol-4 or 5-ylcarbonyl, 1,2,4-thiadiazol-3 or 5-ylcarbonyl, 1,2,5-thiadiazol-3 or 4-ylcarbonyl, 1,3,4-thiadiazol-2 or 5-ylcarbonyl, 2- or 3-pyrrolidinylcarbonyl, 2-,3- or 4-pyridylcarbonyl, 2-,3- or 4-pyridyl-N-oxide-carbonyl, 3- or 4-pyridazinylcarbonyl, 3- or 4-pyridazinyl-N-oxide-carbonyl, 2-,4- or 5-pyrimidinylcarbonyl, 2-,4- or 5-pyrimidinyl-N-oxide-carbonyl, pyrazinylcarbonyl, 2-,3- or 4-piperidinylcarbonyl, piperazinylcarbonyl, 3H-indol-2 or 3-ylcarbonyl, 2-,3- or 4-pyranylcarbonyl, 2-,3- or 4-thiopyranylcarbonyl, 3-,4-,5-,6-,7- or 8-quinolylcarbonyl, pyrido[2,3-d]pyrimidinylcarbonyl (e.g., pyrido[2,3-a]pyrimidin-2-ylcarbonyl), 1,5-, 1,6-, 1,7-, 1,8-, 2,6- or 2,7-naphthyridinylcarbonyl (e.g., 1,5-naphthyridin-2 or 3-ylcarbonyl), thieno[2,3-d]pyridylcarbonyl (e.g., thieno[2,3-d]pyridin-3-ylcarbonyl) pyrazinoquinolylcarbonyl (e.g., pyrazino [2,3-b]quinolin-2-ylcarbonyl), or chromenylcarbonyl (e.g., 2H-chromen-2 or 3-ylcarbonyl); or a 5 or 6 membered heterocycle-acetyl group, preferably containing 1 to 4 hetero atoms such as nitrogen atom (which may be oxidized), oxygen atom or sulfur atom (which may be oxidized) in the heterocycle, such as 2-pyrrolylacetyl, 3-imidazolylacetyl or 5-isoxazolylacetyl.

The group of the formula -T-$Q_0$ includes an alkyloxy, alkenyloxy, aryloxy, aralkyloxy, heterocycleoxy, acyloxy group, alkylthio, alkenylthio, arylthio, aralkylthio, heterocyclethio, acylthio, alkyldithio, aryldithio, aralkyldithio, alkylsulfinyl, alkenylsulfinyl, arylsulfinyl, aralkylsulfinyl, heterocyclesulfinyl, alkylsulfonyl, alkenylsulfonyl, arylsulfonyl, aralkylsulfonyl and heterocyclesulfonyl groups.

Here, the alkyloxy group means a straight chain, branched chain or cyclic alkyloxy group preferably containing 1 to 6 carbon atoms, such as methoxy, ethoxy, n-propoxy, isopropoxy, n-butoxy, isobutoxy, sec-butoxy, tert-butoxy, n-pentyloxy, sec-pentyloxy, isopentyloxy, neopentyloxy, cyclopentyloxy, n-hexyloxy, isohexyloxy or cyclohexyloxy. The alkenyloxy group means a straight chain, branched chain or cyclic alkenyloxy group preferably containing 3 to 6 carbon atoms, such as allyloxy, isopropenyloxy, 1-butenyloxy, 2-pentenyloxy or 2-hexenyloxy, The aryloxy group means an aryloxy group preferably containing 6 to 14 carbon atoms, such as phenoxy, naphthyloxy or biphenylyloxy. The aralkyloxy group means an aralkyloxy group preferably containing 7 to 19 carbon atoms, such as benzyloxy, phenethyloxy or phenylpropyloxy. The heterocycleoxy group means a group of the formula T'-O- (T' is the heterocyclic group as mentioned above), such as 2- or 3-pyrrolyloxy, 3-,4- or 5-pyrazolyloxy, 2-,4- or 5-imidazolyloxy, 1,2,3-triazol-4-yloxy, 1,2,4-triazol-3-yloxy, 1H- or 2H-tetrazol-5-yloxy, 2-or 3-furyloxy, 2- or 3-thienyloxy, 2- or 3-thienyloxy-1,1-dioxide or 2-,4- or 5-oxazolyloxy. The acyloxy group means a group of the formula T''—O— (T'' is the acyl group as mentioned above), such as acetoxy, propionyloxy, butyryloxy, pentanoyloxy, hexanoyloxy, benzylcarbonyloxy, phenethylcarbonyloxy, benzoyloxy, naphthoyloxy, thienylcarbonyloxy or benzothienylcarbonyloxy. The alkylthio group means a straight chain, branched chain or cyclic alkylthio group preferably containing 1 to 6 carbon atoms, such as methylthio, ethylthio, n-propylthio, isopropylthio, n-butylthio, isobutylthio, sec-butylthio, tert-butylthio, n-pentylthio, sec-pentylthio, isopentylthio, neopentylthio, cyclopentylthio, n-hexylthio, isohexylthio or cyclohexylthio. The alkenylthio group means a straight chain, branched chain or cyclic alkenylthio group preferably containing 3 to 6 carbon atoms, such as allylthio, isopropenylthio, 1-butenylthio, 2-pentenylthio or 2-hexenylthio. The arylthio group means an arylthio group preferably containing 6 to 14 carbon atoms, such as phenylthio, naphthylthio or biphenylylthio. The aralkylthio group means an aralkylthio group preferably containing 7 to 19 carbon atoms, such as benzylthio, phenethylthio or phenylpropylthio. The heterocyclethio group means a group of the formula T''S— (T' denotes a heterocyclic group as mentioned above), such as 2- or 3-pyrrolylthio, 3-,4- or 5-pyrazolylthio, 2-,4- or 5-imidazolylthio, 1,2,3-triazol-4-ylthio, 1,2,4-triazol-5-ylthio 1H- or 2H-tetrazol-5-ylthio, 2- or 3-furylthio, 2- or 3-thienylthio, 2- or 3-thienylthio-1,1-dioxide, 2-,4- or 5-oxazolylthio or the like. The acylthio group means a group of the formula T'''-S- (T'' is an acyl group as mentioned above), such as acetylthio, propionylthio, butyrylthio, pentanoylthio, hexanolythio, benzylcarbonylthio, phenethylcarbonylthio, benzoylthio, naphthoylthio, thienylcarbonylthio or benzothienylcarbonylthio. The alkyldithio group means a straight chain, branced chain or cyclic alkyldithio group preferably containing 1 to 6 carbon atoms, such as methyldithio, ethyldithio, n-propyldithio or cyclopentyldithio. The aryldithio group means an aryldithio group preferably containing 6 to 14 carbon atoms, such as phenyldithio, naphthyldithio or biphenylyldithio. The aralkyldithio group means an aralkyldithio group preferably containing 7 to 19 carbon atoms, such as benzyldithio or phenethyldithio. The alkylsulfinyl group means a straight chain, branched chain or cyclic alkylsulfinyl group preferably containing 1 to 6 carbon atoms, such as methylsulfinyl, ethylsulfinyl, n-propylsulfinyl, n-hexylsulfinyl or cyclohexylsulfinyl. The alkenylsulfinyl group means a straight chain, branched chain or cyclic alkenylsulfinyl group preferably containing 3 to 6 carbon atoms such as allylsulfinyl. The arylsulfinyl group means an arylsulfinyl group preferably containing 6 to 14 carbon atoms such as phenylsulfinyl. The aralkylsulfinyl group means an aralkylsulfinyl group preferably containing 7 to 19 carbon atoms, such as benzylsulfinyl; the heterocyclesulfinyl group means a group of the formula T'-SO- (T' denotes the heterocyclic group as mentioned above), such as 2- or 3-pyrrolylsulfinyl or 3-,4- or 5-pyrazolylsulfinyl. The alkylsulfonyl group means a straight chain, branched chain or cyclic alkylsulfonyl group preferably containing 1 to 6 carbon atoms, such as methylsulfonyl, ethylsulfonyl or cyclohexylsulfonyl. The alkenylsulfonyl group means a straight chain, branched chain or cyclic alkenylsulfonyl group preferably containing 3 to 6 carbon atoms, such as allylsulfonyl. The arylsulfonyl group means an arylsulfonyl group preferably containing 6 to 14 carbon atoms, such as phenylsulfonyl, naphthylsulfonyl or biphenylylsulfonyl. The aralkylsulfonyl group means an aralkylsulfonyl group preferably containing 7 to 19 carbon atoms, such as benzylsulfonyl, phenethylsulfonyl or phenylpropylsulfonyl. The heterocyclesulfonyl group means a group of the formula T'—SO$_2$— (T' is the heterocyclic group as mentioned above), such as 2- or 3-pyrrolylsulfonyl or 3-, 4- or 5-pyrazolylsulfonyl.

The group of the formula

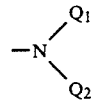

includes an alkylamino group, preferably, a mono- or di-alkylamino group containing 1 to 6 carbon atoms in each alkyl, such as methylamino, ethylamino, n-propylamino, n-butylamino, tert-butylamino, n-pentylamino, n-hexylamino, dimethylamino, diethylamino, methylethylamino, di-(n-propyl)amino or di-(n-butyl)amino; a cycloalkylamino group, preferably, a mono- or dicycloalkylamino group containing 3 to 6 carbon atoms in each cycloalkyl, such as cyclopropylamino, cyclopentylamino, cyclohexylamino or dicyclohexylamino; an arylamino group preferably containing 6 to 14 carbon atoms, such as anilino or N-methylanilino, an aralkylamino group preferably containing 7 to 19 carbon atoms, such as benzylamino, 1-phenylethylamino, 2-phenylethylamino, benzhydrylamino or tritylamino; and an acylamino group of the formula T''—NH— or (T'')$_2$N— (T'' is the acyl group as mentioned above, and the two T'' groups may form a ring together with the nitrogen atom), for example, an alkylcarbonylamino group, an arylcarbonylamino group, a heterocyclecarbonylamino group or a cyclic imido group (here, the alkyl, aryl and heterocyclic groups are preferably the same with those mentioned above), such as acetamido, propionamido, butyrylamino, pentanoylamino, hexanoylamino, succinimido, benzylcarbonylamino (benzylcarboxamido), phenethylcarbonylamino (phenethylcarboxamido), benzoylamino (benzamido), naphthoylamino, phthalimido, thienylcarbonylamino (thienylcarboxamido) or benzothienylcarbonylamino (benzothienylcarboxamido).

The group of the formula

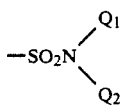

includes a mono- or di-alkylsulfamoyl group preferably containing 1 to 6 carbon atoms in each alkyl, such as methylsulfamoyl, ethylsulfamoyl, n-propylsulfamoyl, n-hexylsulfamoyl, dimethylsulfamoyl, diethylsulfamoyl, methylethylsulfamoyl or di-(n-butyl)sulfamoyl; a cycloalkylsulfamoyl group preferably containing 3 to 6 carbon atoms, such as cyclopropylsulfamoyl or cyclohexylsulfamoyl; an arylsulfamoyl group preferably containing 6 to 14 carbon atoms, such as phenylsulfamoyl, an aralkylsulfamoyl preferably containing 7 to 19 carbon atoms, such as benzylsulfamoyl, 1-phenylethylsulfamoyl, 2-phenylethylsulfamoyl, benzhydrylsulfamyl or tritylsulfamoyl; and an acylsulfamoyl group of the formula T''—NHSO$_2$— or (T'')$_2$N—SO$_2$— (T'' is the acyl group as mentioned above), such as acetylsulfamoyl, benzylcarbonylsulfamoyl or thienylcarbonylsulfamoyl.

The group of the formula $Q_2$—SO$_2$—O— includes an alkylsulfonyloxy group preferably containing 1 to 6 carbon atoms, such as methanesulfonyloxy or ethanesulfonyloxy; an arylsulfonyloxy group preferably containing 6 to 14 carbon atoms such as benzenesulfonyloxy or p-toluenesulfonyloxy; an aralkylsulfonyloxy group preferably containing 7 to 19 carbon atoms, such as benzylsulfonyloxy or phenethylsulfonyloxy; and an acylsulfonyloxy group such as acetylsulfonyloxy or butyrylsulfonyloxy.

The above mentioned alkyl, alkyloxy (or alkoxy), alkylthio, alkyldithio, alkylsulfinyl, alkylsulfonyl, alkylamino, cycloalkylamino, alkenyl, alkenyloxy, alkenylthio, alkenyldithio, alkenylsulfinyl, alkenylsulfonyl, alkinyl, alkoxycarbonyl, alkanoyl and alkylsulfonyloxy groups may be further substituted by one to three of alkylthio group (for example, a straight chain or branched chain alkylthio group containing 1 to 4 carbon atoms, such as methylthio, ethylthio, n-propylthio or isopropylthio), a halogen atom (for example, fluorine, chlorine, bromine or iodine), an alkoxy group (for example, a straight chain or branched chain alkoxy group containing 1 to 6 carbon atoms, such as methoxy, ethoxy, n-propoxy, tert-butoxy or n-hexyloxy), nitro, an alkoxycarbonyl group (for example, an alkoxycarbonyl group containing 1 to 6 carbon atoms in the alkoxy moiety, such as methoxycarbonyl, ethoxycarbonyl, n-propoxycarbonyl, i-propoxycarbonyl, n-butoxycarbonyl, i-butoxycarbonyl, sec-butoxycarbonyl or tert-butoxycarbonyl), or an alkylamino group (for example, mono- or di-(C$_{1-6}$ alkyl)amino group, such as methylamino, ethylamino, n-propylamino, n-butylamino, tert-butylamino, n-pentylamino, n-hexylamino, dimethylamino, diethylamino, methylethylamino, di-(n-propyl)amino or di-(n-buthyl)amino).

In case where any of the above mentioned groups is substituted by two alkoxy groups, these alkoxy groups may be combined to form alkylenedioxy group containing 1 to 3 carbon atoms, such as methylenedioxy, ethylenedioxy or propylenedioxy, or alkylidenedioxy containing 2 to 6 carbon atoms, such as ethylidenedioxy, propylidenedioxy or i-propylidenedioxy.

The above-mentioned aryl, aryloxy, aryloxycarbonyl, arylcarbonyl, arylthio, aryldithio, arylsulfinyl, arylsulfonyl, arylamino, aralkyloxy, aralkyloxycarbonyl, aralkylthio, aralkyldithio, aralkylsulfinyl, aralkylsulfonyl, aralkylamino, aralkylcarbonyl, arylsulfonyloxy, and aralkylsulfonyloxy groups may be further substituted on their aromatic ring by one to three of alkyl, alkenyl, alkynyl, alkoxy, acyl, acyloxy, nitro, cyano, halogen, acylamino or alkylthio. Here, the same alkyl, alkenyl, alkynyl, alkoxy, acyl, acyloxy, acylamino or alkylthio group or halogen atom as mentioned above are used.

In case of being substituted by two alkyl groups adjacent to each other, these groups may be combined to form a bivalent group such as trimethylene or tetramethylene and in case of being substituted by two alkenyl groups adjacent to each other, they may be combined to form a bivalent group such as propenylene, 1-butenylene, 2-butenylene or butadienylene.

In such cases, these bivalent groups may form a 5 or 6 membered alicycle (for example, cyclopentane, cyclohexane or cyclohexadiene), an aromatic ring (for example, benzene) or a 5 or 6 membered heterocycle containing 1 to 4 hetero atoms such as nitrogen atom (which may be oxidized), oxygen atom or sulfur atom (which may be oxidized), together with the condensed heterocyclic group.

Preferred examples of the organic residues include (1) an alkyl group which may be substituted by the same or different 1 to 3 substituents of halogen, alkylthio or alkoxy, (2) an aryl group, (3) an alkylthio group, (4) an alkenylthio group, (5) an alkylsulfinyl group, (6) an alkylsulfonyl group, (7) an alkenylsulfonyl group, (8) an alkoxycarbonyl, (9) carbamoyl group, (10) butadienylene group and (11) an alkylamino group.

The above mentioned heterocycleoxy, heterocyclethio, heterocyclesulfinyl, heterocyclecarbonyl and heterocyclesulfonyl groups may be substituted on their heterocyclic group by one or three of the above mentioned alkyl, alkenyl, alkinyl, aryl, aralkyl, alkanoyl, arylcarbonyl, alkoxycarbonyl, aryloxycarbonyl, aralkylcarbonyl, nitro, amino, hydroxyl, cyano, sulfamoyl or mercapto group or a halogen atom (for example, fluorine, chlorine, bromine, iodine).

Preferred examples of Q include a group of the formula:

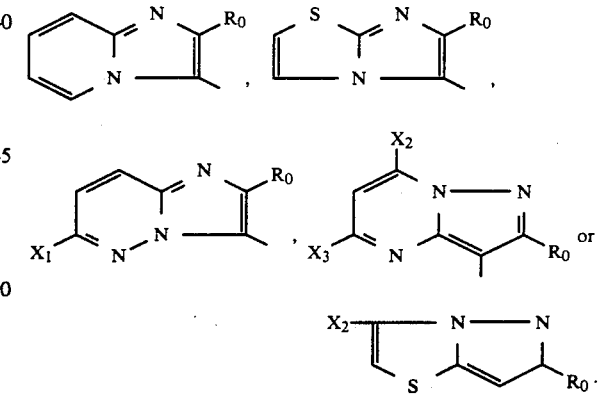

wherein R$_0$ is hydrogen, a lower alkyl group which may be substituted by halogen, a lower alkylthio, lower alkylsulfonyl or lower alkoxycarbonyl group or a halogen; X$_1$ is hydrogen, a halogen, or a lower alkoxy, lower alkylthio, lower alkylamino or di-(lower alkyl)amino group; and X$_2$ and X$_3$ each are hydrogen or a lower alkyl group.

The lower alkyl group in the lower alkyl, lower alkyl optionally substituted by halogen, lower alkylthio, lower alkylsulfonyl, lower alkylamino and di-(lower alkyl) amino groups may be an alkyl group containing 1 to 4 carbon atoms (for example, methyl, ethyl, n-propyl, isopropyl, n-butyl or t-butyl).

The lower alkoxy group may be an alkoxy group containing 1 to 4 carbon atoms (for example, methoxy, ethoxy, propoxy, isopropoxy or t-butoxy).

The halogen and the halogen in the lower alkyl group which may be substituted by halogen may be fluorine, chlorine or bromine.

The alkyl group of $R_1$ and $R_2$ is preferably a straight chain, branched chain or cyclic alkyl group containing 1 to 6 carbon atoms, such as methyl, ethyl, n-butyl, isobutyl, sec-butyl, tert-butyl, n-pentyl, sec-pentyl, iso-pentyl, neopentyl, cyclopentyl, n-hexyl, isohexyl, cyclohexyl or the like. The alkoxy group of $R_1$ and $R_2$ is preferably a straight chain or branched chain alkoxy group containing 1 to 6 carbon atoms, such as methoxy, ethoxy, n-propoxy, isopropoxy, n-butoxy, isobutoxy, sec-butoxy, tert-butoxy, n-pentyloxy, n-hexyloxy or the like. The halogen atom of $R_1$ and $R_2$ means fluorine, chlorine, bromine, iodine or the like.

More preferred $R_1$ and $R_2$ each are a lower alkyl group containing 1 to 4 carbon atoms such as methyl, ethyl, n-propyl, isopropyl, n-butyl or t-butyl; a lower alkoxy group containing 1 to 4 carbon atoms such as methoxy, ethoxy, n-propoxy, isopropoxy, n-butoxy or t-butyl, or a halogen such as fluorine, chlorine or bromine. The most preferred $R_1$ and $R_2$ each are methyl, methoxy or chlorine. Preferred W is O. Preferred Z is CH.

The compound (I) can form an inorganic or organic base salt at an acidic group in the molecule i.e.

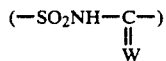

and an acidic group in the substituent such as sulfo or carboxyl, or an inorganic or organic acid addition salt at a basic nitrogen atom in the molecule and a basic group in the substituent such as amino.

Examples of the inorganic base salts of the compounds (I) include the salt with a conventional base such as alkali metal such as sodium or potassium, an alkaline earth metal such as calcium, or ammonia. Examples of the organic base salts of the compounds (I) include a conventional salt such as a salt with dimethylamine, triethylamine, piperazine, pyrrolidine, piperidine, 2-phenylethylbenzylamine, benzylamine, ethanolamine or diethanolamine.

Examples of the inorganic acid addition salts of the compounds (I) include a salt with a conventional acid such as the salt with hydrochloric acid, hydrobromic acid, sulfuric acid, nitric acid or phosphoric acid. Examples of the organic acid addition salts of the compounds (I) include a conventional salt with p-toluene sulfonic acid, methanesulfonic acid, formic acid or trifluoroacetic acid.

The compound (I) or their salts exhibit in an extremely low application amount an excellent herbicidal effect against a broad range of weeds, for example, paddy weeds such as *Echinochloa oryzicola, Cyperus difformis, Scirpus juncoides, Monochoria vaginalis, Sagittaria pygmaea, Eleocharis acicularis, Cyperus serotinus, Eleocharis kuroguwai, Alisma canaliculatum, Sagittaria trifolia, Scirpus wallichii, Lindernia procumbens, Rotala indica, Potamogeton distinctus, Ludwiga prostrata* or *Flatine triandra*, and field weeds, such as *Digitaria adscendens, Setaria viridis, Amaranthus viridis, Abutilon theophrasti, Chenopodium album, Polygonum longisetum, Portulaca oleracea, Sida spinosa, Datura stramonium, Ipomoea purpurea, Xanthium strumarium, Echinochloa crus-galli, Panicum dichotaomiflorum, Sorghum halepense, Cyperus rotundus, Avena fatua, Alopecurus mvosuroides, Bromus tectorum, Stellaria media, Brassica Sp., Cassia obtusifolia, Matricaria chamomilla* or *Commelina communis*. Moreover, they exhibit substantially no damage on crops such as rice, wheat, barley, corn, soybean, etc. and show a high grade of safety.

The compounds (I) or their salts exhibit an excellent herbicidal effect selectively on various weeds only, and not on crops, and are only slightly toxic to mammals, fishes and shellfishes. Therefore, they can be used as herbicides for paddy field, field (farm field), orchard or non-farming land, in extremely high safety, without polluting the environment.

The compounds (I) or their salts can be used as herbicide in any application form suited for general agricultural chemicals. That is, one, two, or more than two kinds of the compounds (I) or their salts are used in the form of preparation such as emulsifiable concentrates, oil solution, sprays, wettable powders, dusts, DL(Driftless)-type dusts, granules, fine granules, fine granules F, tablets or the like, according to the purpose of use, by dissolving or dispersing them in suitable liquid carriers or mixing them with or adsorbing them on suitable solid carriers. These preparations may contain, if necessary, emulsifying agent, suspending agent, spreading agent, penetrating agent, wetting agent, thickening agent, stabilizer, etc., and can be prepared by any conventional method known per se., e.g. mixing each ingredients.

Suitable examples of the liquid carriers (solvents), include solvents such as water, alcohols (for example, methanol, ethanol, n-propanol, isopropanol or ethylene gylcol), ketones (for example, acetone or methyl ethyl ketone), ethers (for example, dioxane, tetrahydrofuran, ethylene glycol monomethyl ether, diethylene glycol monomethyl ether or propylene glycol monomethyl ether), aliphatic hydrocarbons (for example, kerosine, kerosene oil, fuel oil or machine oil), aromatic hydrocarbons (for example, benzene, toluene, xylene, solvent naphtha or methylnaphthalene), halogenated hydrocarbons (for example, dichloromethane, chloroform or carbon tetrachloride), acid amides (for example, dimethylformamide or dimethylacetamide), esters (for example, ethyl acetate, butyl acetate or fatty acid glycerol ester) or nitriles (for example, acetonitrile or propionitrile). These solvents are used individually or as a suitable mixture of two, or more, of them.

Suitable examples of the solid carriers (diluents or dust carrier) include vegetable powder (for example, soybean meal, tobacco meal, wheat flour or wood flour, mineral powders (for example, clays such as kaolin, bentonite, or acid clay, talcs such as talc powder or pyrophyllite powder), silicas (for example, diatomaceous earth or mica powder), aluminas, sulfur powder or active carbon are suitably used. They are used individually or as a suitable mixture of two, more, of them.

As surface active agents used as the emulsifying agent, spreading agent, penetrating agent or dispersing agent, if necessary use can be made of nonionic or anionic surface active agents such as soaps; polyoxyethylene alkylaryl ethers (e.g. Noigen EA 142 ® from Dai-ichi Kogyo Seiyaku K.K., Japan); polyoxyethylene aryl esters (e.g. Nornal ® from Toho Chemical K.K., Japan); alkyl-sulfates (e.g. Emal 10 ® and Emal 40 ® from Kao Soap K.K., Japan); alkyl sulfonates (e.g. Neogen ® and Neogen T ® from Dai-ichi Kogyo Seiyaku Co. and Neopelex ® from Kao Soap K.K.); polyethylene glycol ethers (e.g. Nonipol 85®, Nonipol 100®, Nonipol 160® from Sanyo Kasei K.K., Japan); or polyhydric alcohol esters (e.g. Tween 20® and Tween 80® from Kao Soap K.K.).

The amount of the compound (I) or a salt thereof contained in the herbicidal preparation is suitably about 1 to 90% by weight in the case of emulsifiable concentrates or wettable powders, about 0.01 to 10% by weight in the case of oil solution, dusts or DL-type dusts and about 0.05 to 10% by weight in the case of fine granules F or granules. However, such concentration may be changed properly, depending on the purpose of use. Emulsifiable concentrates, wettable powders or the like are suitably diluted or extended (for example, to 100 to 100000 times) with water or the like, on the occasion of use, and then scattered.

When the compound (I) or its salt is used as herbicide, its amount may vary depending on the place, the season and the method of application, the kinds of target weeds, the kinds of culture crops, and so on. However, an active ingredient (the compound (I) or its salt) is used in general, in an amount of about 0.05 to 50 g, preferably about 0.1 to 5 g, per are of paddy field and in an amount of about 0.05 to 20 g, preferably about 0.1 to 5 g, per are of field.

For paddy field weeds, it is suitable to use the compound (I) or its salt in the soil treatment before germination or in the cormophyte and soil treatment.

For example, the herbicidal preparation of this invention can be used in safety just after the rice-planting or even 2 to 3 weeks after the planting without revealing any harmful effect on the rice, and its effect continues for a long period of time.

The herbicidal preparation of this invention can be used, as occasion demands, in combination with or as an admixture with other herbicidal agent, plant-growth regulating agent, fungicidal agent (for example, organochlorine series fungicide, organosulfur series fungicide or azole series fungicide, antibiotics), insecticidal agent (for example, pyrethroid series insecticide, organophosphorus series insecticide or carbamate series insecticide), and also with miticide, nematocide, synergist, attractant, repellent, dyestuff, fertilizer and the like.

The compound (I) or its salt can be prepared according to the processes known per se (for example, the process described in Japanese Unexamined Patent Publication No. 122384/1977). Further, the compound (I) or its salt can be prepared, for example, by reacting a compound (II) or its salt with a compound (III) or its salt.

More particularly, the compound (I) or its salt can be prepared according to the following reaction schemes 1 to 4: By the way, as salts of the compounds (II''), (II'''), (III'), the same salts as the above-mentioned salts of the compounds (I) are used.

Reaction scheme 1

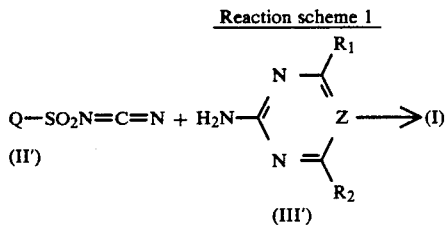

(wherein the symbols have the same meanings as described above)

In this reaction are usually used almost equimolar amount of the compound (II') and the compound (III') or its salt. The reaction is performed in a solvent which does not hamper the reaction. Suitable examples of the solvents include an aromatic hydrocarbon such as benzene or toluene; a halogenated hydrocarbon such as dichloromethane, chloroform or carbon tetrachloride; an ether such as ethyl ether, isopropyl ether, dioxane or tetrahydrofuran (hereafter, abbreviated as THF); a nitrile such as acetonitrile; a ketone such as acetone or methyl ethyl ketone; an ester such as ethyl acetate or butyl acetate; or dimethylformamide or dimethylsulfoxide. The reaction is generally accelerated by addition of a base. Examples of the bases include an organic base such as triethylamine, tri-n-propylamine, pyridine, 1,8-diazabicyclo[5,4,0]-7-undecene (hereafter, abbreviated as DBU), 1,4-diazabicyclo[2,2,2]octane (hereafter, abbreviated as DBO) or 1,5-diazabicyclo[4,3,0]non-5-ene (hereafter, abbreviated as DBN) or an inorganic base such as potassium hydroxide, sodium hydride, potassium carbonate, sodium carbonate or sodium hydroxide. The base may be usually used in an amount of about 0.01 to 3 moles per 1 mol of the compound (II'). The reaction temperature is usually about $-10°$ to $150°$ C., preferably about $10°$ to $80°$ C. The reaction is completed within about 30 minutes to 20 hours, and its completion can be confirmed by means of thin-layer chromatography or high performance liquid chromatography.

Reaction scheme 2

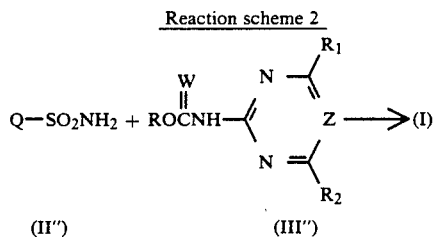

(wherein R is a hydrocarbon residue and other symbols have the same meanings as described above)

As the hydrocarbon residue denoted by R, the same hydrocarbon residues as defined for the group B are applicable and its preferred examples include an alkyl group (for example, methyl, ethyl, n-propyl or isopropyl), an aryl group (for example, phenyl, chlorophenyl, tolyl or biphenylyl). In the reaction, the compound (II'') or its salt is used in an amount almost equimolar to the compound (III'') or its salt, usually. The reaction is performed in a solvent which does not hamper the reaction. As the solvent, the same solvents as used in the reaction shown by the reaction scheme 1 may be used. Preferred examples of the solvents are chloroform, acetonitrile and dioxane. The reaction proceeds advantageously in the presence of a base. Examples of the bases include an organic base such as triethylamine, tri-n-propylamine, pyridine, DBU, DBO or DBN; or an inorganic base such as potassium hydroxide, sodium hydroxide, potassium carbonate, sodium carbonate or calcium carbonate. The base is used in an amount of usually about 0.8 to 5 moles, preferably about 1 to 3 moles, per 1 mol of the compound (III'') or its salt. The reaction temperature is usually about $-10°$ to $150°$ C., preferably about $20°$ to $100°$ C. The reaction is completed within about 30 minutes to several days, and its completion can be confirmed by means of thin layer chromatography or high performance liquid chromatography.

This reaction is especially suited for the preparation of the compound (I) wherein W is O.

Reaction scheme 3

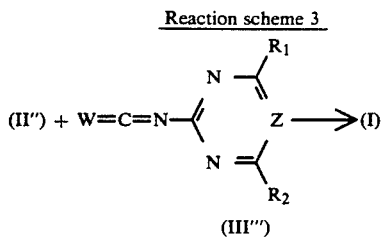

(wherein the symbols have the same meanings as described above)

This reaction is suited for the preparation of the compound (I) wherein X is S, i.e., sulfonylisothioureas. The reaction is usually performed using about equimolar amount of the compound (II') or its salt and the compound (III'''). The reaction is performed in a solvent which does not hamper the reaction, preferably in the presence of a base. The kinds and the amounts of the solvent and the base used in this reaction are the same as those in the reaction of the reaction scheme 1.

Reaction scheme 4

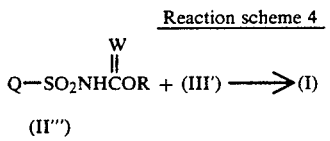

(wherein the symbols have the same meanings as described above)

In this reaction, the compound (II''') or its salt is usually used in about equimolar amount to the compound (III') or its salt. As the solvents, the same ones used for the reaction of Reaction scheme 1 are here applicable. The preferred examples of the solvents are chloroform, chlorobenzene, acetonitrile and acetone. The reaction temperature is usually about 0° to 150° C., preferably about 20° to 100° C. The reaction is completed within about 30 minutes to 10 days. Its completion can be observed by means of thin layer chromatography or high performance liquid chromatography.

In addition, the compound (I) wherein W is oxygen, i.e., the compound (I') or its salt for example can be prepared by reacting the compound (IV) or its salt with the compound (V). As the salt of the compound (I') the same one used for the compound (I) is applicable.

In the reaction the compound (IV) or its salt is used in about equimolar amount to the compound (V). The reaction is usually performed in a solvent which does not hamper the reaction. Suitable solvents are for example, a halogenated hydrocarbon such as dichloromethane, chloroform or carbon tetrachloride; an ether such as ethyl ether, isopropyl ether, THF or dioxane; or carbon disulfide or nitrobenzene. The reaction is generally accelerated by addition of an acid. Examples of the acids include a metal halide such as aluminum chloride, titanium tetrachloride, ferric chloride, zinc chloride or stannic chloride, or boron trifluoride ethyl etherate. The acid may be used in about 0.1 to 3 moles to one mole of the compound (IV). The reaction temperature is about 0° to 150° C., preferably about 10° to 60° C. The reaction time is within about 10 minutes to 5 hours.

The compound (I) obtained by the above mentioned reactions has an acidic group

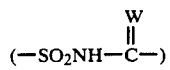

in its molecule, and therefore, when a base is used in the reaction, it may be present in the form of its salt with the base. Also, when the compound (I) has an acidic group such as sulfo or carboxyl in the molecule, it may be obtained as its salt with a base employed In such case, it can be converted, if necessary, to the free form by addition of, for example, an inorganic acid such as hydrochloric acid, sulfuric acid, phosphoric acid or nitric acid or an organic acid such as formic acid, acetic acid, trifluoroacetic acid or p-toluenesulfonic acid. When the compound (I) is obtained in the form of the free form, it can be converted into its base salt by addition of a base mentioned above. Also, since the compound has a basic nitrogen atom, it may form its acid addition salt with an inorganic or organic acid mentioned above. In addition, when the compound (I) has a substituent which is a basic group such as amino, it may form its acid addition salt.

The compound (I) when obtained in the free form may be converted into its acid addition salt by addition of an inorganic or organic acid mentioned above and also when obtained in the form of the acid addition salt, may be converted into its free form by addition of a base mentioned above.

The compound (I) or its salt thus obtained can be isolated and purified by a known procedure per se such as concentration, concentration under reduced pressure, extraction, phase transfer, crystallization, recrystallization or chromatography.

The compound (III'), (III'') or their salt and the compound (III'''), used as the starting material of the processes of this invention, are known or can be easily prepared from known compounds.

The compound (III') or its salt can be prepared, for example, by the processes described in the Chemistry of Heterocyclic Compounds (Interscience Publishers. New York & London), Vol. 16, 1962 and Journal of Organic Chemistry, Vol. 28, pages 1812 to 1821 (1963) or processes corresponding thereto.

The compound (III'') or its salt can be prepared, for example, by the processes as described in Japanese Unexamined Patent Publication Nos. 23676/1983, 219180/1983, 216167/1983 and 59671/1984 or processes corresponding thereto. Among the compounds (III'''), isocyanates (compounds of the formula (III''') wherein W is O) can be prepared, for example, by the process described in Angewandte Chemie, International Edition, Vol. 10, pages 402 to 403,(1971) or process corresponding thereto, and isothiocycnates (compounds of the formula (III''') wherein W is S) can be prepared for example, by the process described in Japanese Unexamined Patent Publication No. 143686/1976 or process corresponding thereto.

The compound (V) can be prepared, for example, by the process described in Japanese Unexamined Patent Publication No. 126859/1983 or process corresponding there to. The compound (V) may be without isolation, subjected to the reaction with the compound (IV) or its salt.

The compound (II') can be prepared by a process known per se. Among the compounds (II'), sulfonylisocyanates (compounds of the formula (II') wherein W is O) can be prepared according to the process described in Newer Methods of Preparative Organic Chemistry, Academic Press New York, Vol. 6, pages 223-241. Also, among the compounds (II'), sulfonylisothiocyanates (compounds of the formula (II') wherein W is S) can be prepared according to the process described in Angewandte Chemie, International Edition, Vol. 1, page 553 (1962) and Vol. 4, page 430 (1965).

The compounds (II") or its salts can be obtained easily by preparing the compound (VI) or its salt in accordance with any of the methods (1)-(4) shown by the following reaction scheme and subsequently reacting the same with ammonia.

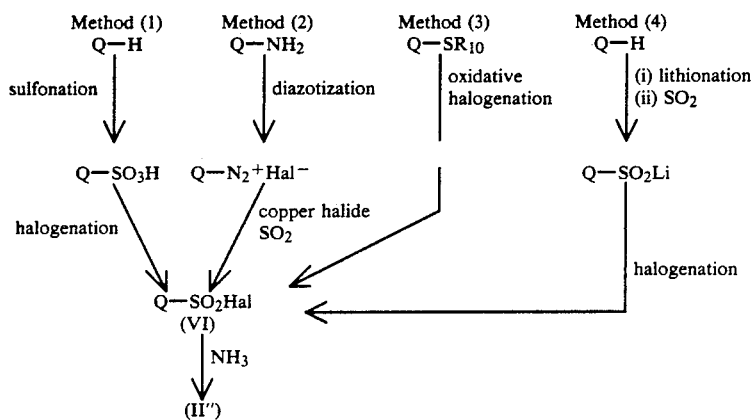

(wherein, Hal is a halogen, $R_{10}$ is hydrogen, benzyl or S-Q, and the other symbols have the same meanings as defined above).

As the halogen atom denoted by Hal, fluorine, chlorine or bromine may be used.

The compounds shown by the above formulas may be used in the form of base salt or acid addition salt thereof as mentioned above.

Specific examples of the above mentioned method (1) are:

(a)
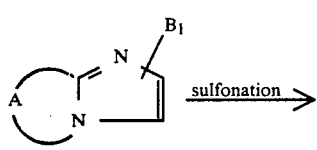

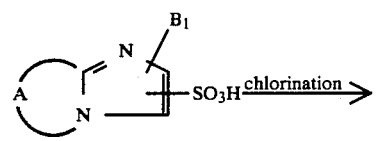

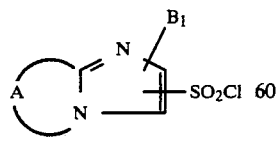

(b)
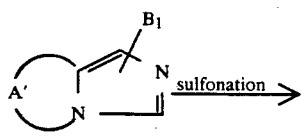

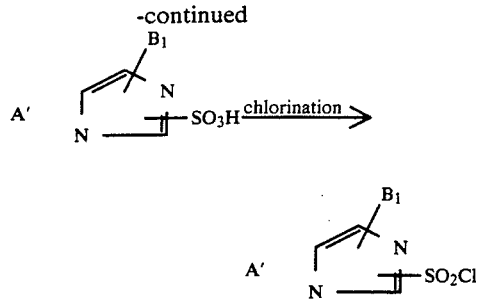

(c)

(d)

-continued

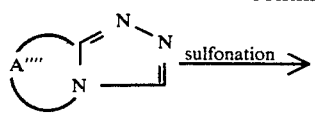
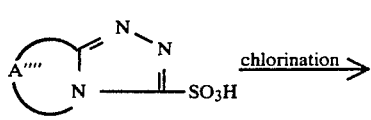
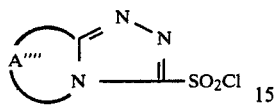

wherein the symbols have the same meanings as defined above.

Specific example of the above mentioned method (2) is:

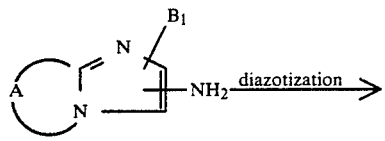
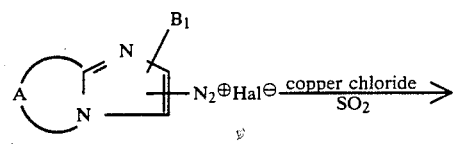
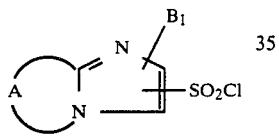

wherein the symbols have the same meanings as defined above.

Specific examples of the above mentioned method (3) are:

(a)
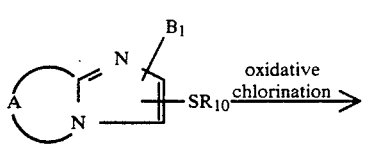
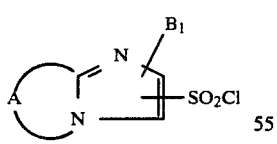

(b)
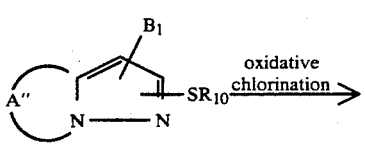
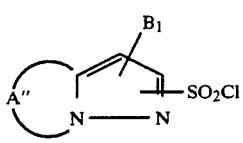

wherein the symbols have the same meanings as defined above.

Specific examples of the above mentioned method (4) are:

(a)
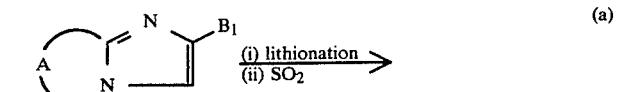
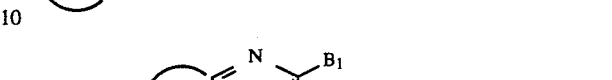
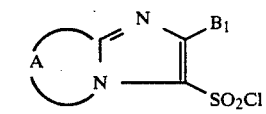

(b)
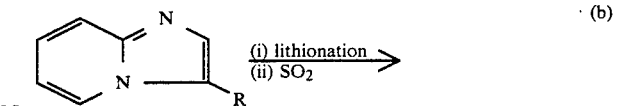
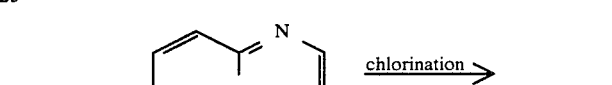
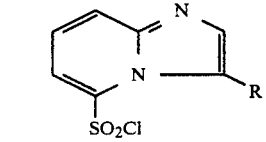

(c)
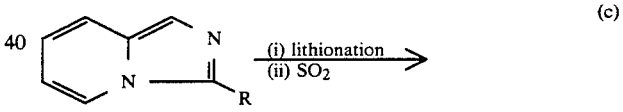
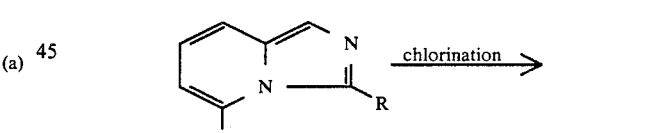
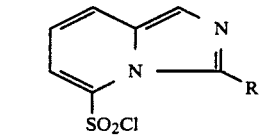

wherein the symbols have the same meanings as defined above.

All the reactions in the methods (1)–(4) for preparing the compound (VI) or its salt are known per se and can be performed, for example, by the processes described in Methoden der Organischen Chemie, Vol. 9, (1955), Sulfonation and Related Reactions (Interscience Publishers, New York) (1965), Synthesis 1969, pages 1 to 10, or Japanese Unexamined Patent Publication No. 208977/1985 or processes corresponding thereto. For example, the compound (VI) or its salt can be prepared by the method mentioned below.

METHOD (1)

In the sulfonation, examples of the sulfonating agent include sulfuric acid, fuming sulfuric acid or chlorosulfonic acid. The sulfonating agent is used in about 0.8 to 3 moles per one mole of the compound Q–H or its salt. This reaction may be carried out in an inert solvent such as carbon disulfide, chloroform, carbon tetrachloride, tetrachloroethane or chlorobenzene. Good results are often obtainable particularly when chlorosulfonic acid in chloroform is used. The reaction temperature is about 0° to 200° C., preferably about 20° to 120° C. The reaction time is about 20 minutes to several days.

In the halogenation of the compound Q–$SO_3H$ or its salt, examples of the halogenating agents are a chlorinating agent such as thionyl chloride or phosphorus oxychloride, or a brominating agent such as thionyl bromide or phosphorus oxybromide. The halogenating agent is used in about 0.8 to 10 moles per 1 mole of the compound Q–$SO_3H$. In some cases, the reaction yield is improved by carrying out the reaction in the presence of pyridine, triethylamine, tri-n-propylamine or N,N-dimethylaniline. The reaction is carried out at about 20° to 120° C. The reaction time is about 30 minutes to 20 hours.

METHOD (2)

In the diazotization of the compound Q–$NH_2$ or salt thereof, the starting material of the compound Q–$NH_2$ reacts with sodium nitrite under a conventional condition for diazotization, for example, in hydrochloric acid under cooling to about −20° to 10° C., to form the diazonium salt of Q–$N_2^+Hal^-$.

Subsequently, the diazonium salt is reacted with sulfur dioxide in the presence of copper halide such as cuprous chloride or cupric chloride, to yield the compound (VI) or salt thereof.

The copper halide is used in about 0.01 to 3 moles per 1 mole of the diazonium salt but may be in a large excess. The reaction is conducted under an acidic condition, at about −20° to 100° C. for about 30 minutes to 12 hours.

METHOD (3)

This method comprises oxidative halogenating (for example, chlorinating) the compound substituted by a group containing bivalent sulfur of Q–$SR_{10}$ or salt thereof in the presence of water, to form the compound (VI) or salt thereof. Examples of the halogenating agent are a chlorinating agent such as chlorine, sodium hypochlorite, potassium hypochlorite or N-chlorosuccinimide; or bromine. The halogenating agent is used in about 1 to 10 moles per 1 mole of the starting compound of Q–$SR_{10}$ or salt thereof. The reaction is preferably conducted under an acidic condition by addition of hydrochloric acid or acetic acid. The reaction temperature is in the range of about −10° to 30° C. and the reaction time is about 30 minutes to 5 hours.

METHOD (4)

This method comprises substituting a hydrogen atom on the heterocycle of the compound Q–H or salt thereof (for example a hydrogen atom on imidazole ring) by lithium, reacting the resultant with sulfur dioxide to form the lithium sulfinate compound Q–$SO_2Li$ and subsequently treating it with a halogenating agent, for example a chlorinating agent to yield the compound (VI) or salt thereof. Examples of the lithionating agent used for the preparation of the compound Q–$SO_2Li$ or salt thereof include an alkyl lithium such as methyl lithium, n-butyl lithium or t-butyl lithium, or lithium amide or lithium diisopropylamide. The lithionating agent is used in about 1 to 3 moles, per 1 mole of the starting compound Q–H or salt thereof and sulfur dioxide in about 1 to 5 moles. The reaction temperature is in the range of about −70° to 50° C. and the reaction time is about 1 to 20 hours.

Examples of the halogenating agents used for the halogenation of the compound Q–$SO_2Li$ or salt thereof include a chlorinating agent such as chlorine or N-chlorosuccinimide. The compound (VI) or salt thereof thus obtained can be converted into the compound (II″) or salt thereof, by the reaction with ammonia. In the reaction of the compound (VI) or salt thereof with ammonia, ammonia is usually used in about 0.8 to 10 moles, per 1 mole of the compound (VI) or salt thereof. The reaction is usually conducted in an inert solvent such as water, ether, THF, acetonitrile, alcohol (for example, methanol or ethanol), dichloromethane or chloroform. The reaction temperature is in the range of about −60° to 100° C. and the reaction time is about 30 minutes to 8 hours.

The compound (II″) or salt thereof also can be prepared by the following reaction scheme.

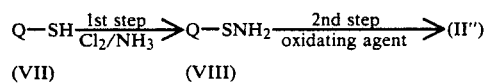

(wherein the symbol has the same meaning as defined above)

Examples of the compounds of the general formula Q–SH are:

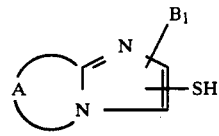

wherein the symbols have the same meanings as defined above.

The 1st step is conducted by reacting the compound (VII) or salt thereof with chlorine or sodium hypochlorite in aqueous ammonia. The reaction is conducted in accordance with the process described in Methoden der Organishen Chemie, 9, 227 to 278.

The 2nd step is conducted by oxidizing the resulting compound (VIII) or salt thereof with an oxidizing agent. Examples of the oxidizing agents are hydrogen peroxide, potassium permanganate or m-chloro-perbenzoic acid.

In this reaction, the oxidizing agent may be used suitably in an amount necessary for completing the reaction, which is theoretically the amount generating 2 equivalents of active oxygen per 1 mole of the compound (VI) or its salt used as the starting material.

The reaction is generally conducted in a solvent which does not hamper the reaction. Suitable examples of the solvent include an inert solvent such as water, an alcohol (for example, methanol, ethanol, n-propanol, isopropanol, n-butanol or tert-butanol), an aromatic hydrocarbon (for example, benzene, toluene, xylene, nitrobenzene or chlorobenzene) or a halogenated hydrocarbon (for example, dichloromethane, chloroform or carbon tetrachloride).

The reaction temperature may be so selected within the range of $-60°$ to $100°$ C. as to cause the reaction to proceed, but is suitably at about $-20°$ to $50°$ C. The reaction time is rather short and is about 5 minutes to 2 hours.

Further, the compound (II″) or salt thereof also can be prepared by the following methods.

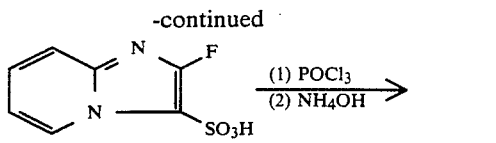

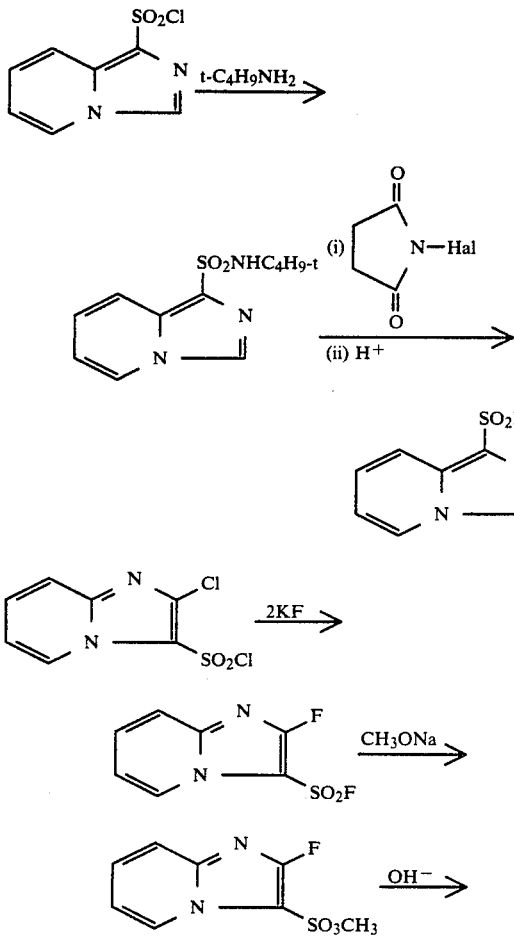

Also, the substituent in the compound (II″) or salt thereof can be easily converted into another one, as is shown by the following reaction schemes.

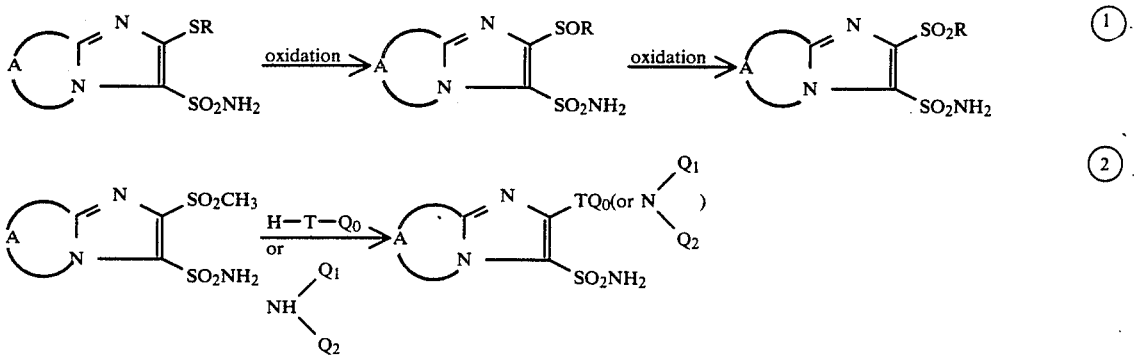

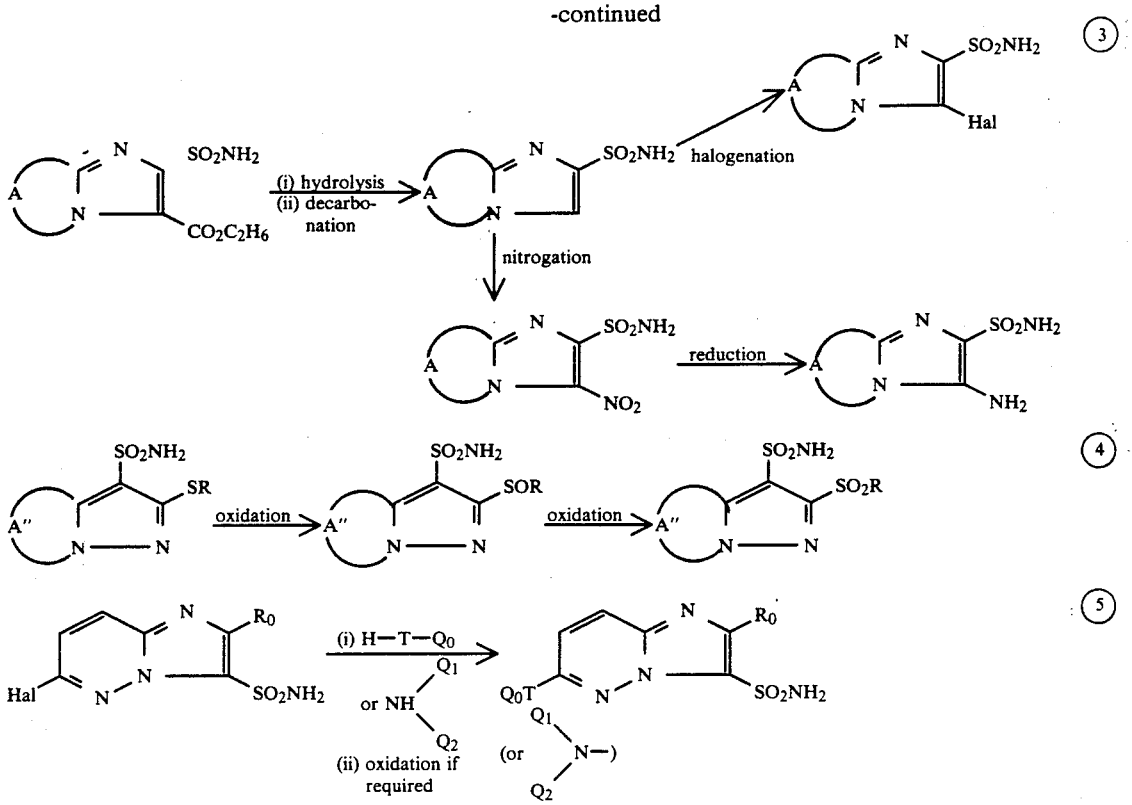

The compound (II''') or salt thereof can be prepared in accordance with the following reaction schemes.

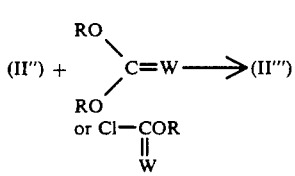

(a)

wherein the symbols have the same meanings as defined above.

In this reaction, the compound (II'') or salt thereof is usually used in about equimolar amount to the compound

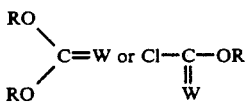

The reaction is usually conducted in a solvent. The solvent is not particularly limited as far as it does not hamper the reaction, but its preferred examples are chloroform, acetone, acetonitrile, dioxane, tetrahydrofuran, 1,2-dimethoxyethane and DMF. The reaction is usually conducted in the presence of a base. Examples of the base are an inorganic base such as sodium hydride, potassium hydroxide, sodium hydroxide, potassium carbonate or sodium carbonate, or an organic base such as triethylamine, tri-n-propylamine, DBU, DBO or DBU. The base is usually used in about 0.8 to 2 moles, per 1 mole of the compound (II'') in free form. The reaction temperature is usually in the range of about 0° to 120° C., preferably about 20° to 90° C. The reaction is completed in about 30 minutes to several days.

The compound (II''') or salt thereof can be prepared by the following reaction scheme, too.

(b)

The reaction is usually conducted by using about equimolar amount of the compound (VI) and the compound

in a solvent in the presence of a base. The base and solvent used in the reaction are the same as those in the above mentioned reaction (a). The reaction temperature is usually in the range of about 10° to 100° C. and the time for completing the reaction is about an hour to several days.

The starting compounds, Q—H, Q—NH$_2$ and Q—SR$_{10}$ and salt thereof can be prepared by methods described in The Chemistry of Heterocyclic Compounds (Interscience Publishers), Vol. 15, Parts 1 and 2; ibid Vol. 30; Comprehensive Heterocyclic Chemistry (Pergamon Press) Vols. 4 and 5; Liebigs Annalen der Chemie, 663, 113 to 117 (1963); ibid. 647, 138 (1961); Journal of Organic Chemistry 49, 3534 (1984); ibid. 38, 1955 (1973); ibid. 36, 11 (1971); ibid. 30, 4081 (1965); ibid. 30, 2403 (1965); Journal of Heterocyclic Chemistry, 2, 53 (1965); ibid. 5, 695 (1968); Journal of Medicinal Chemistry 12, 1031 (1969); ibid. 15, 415 & 982 (1972); ibid. 20, 387 (1977); ibid. 21, 235 (1978); Journal of the Chemical Society 1946, 1075; ibid., 1955, 2834; ibid. 1963, 3277; Chemical and Pharmacuetical Bulletin 11, 1564(1963); ibid. 12, 813(1964); ibid. 22, 482(1974);

Yakugaku-Zasshi, 91, 1154(1971); ibid. 94, 839(1974); ibid. 98, 631(1978); Gazzetta Chmica Italiana, 105, 777(1975); Chemical Abstracts 72, 216696(1970); ibid. 50, 313(1956); ibid. 73, 87855 & 120548p(1970); ibid. 88, 22752r(1978); U.S. Pat. No. 3,901,903; Japanese Patent Publication No. 32793/1979 and Farmaco Edizione Scientifica, 36, 994(1981), or methods corresponding to them.
The methods for the preparation of representative compounds among these starting compounds are given as follows.
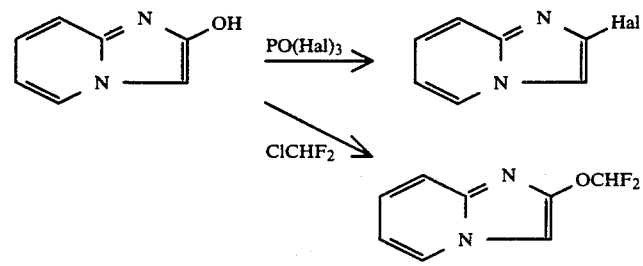
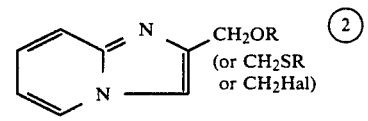
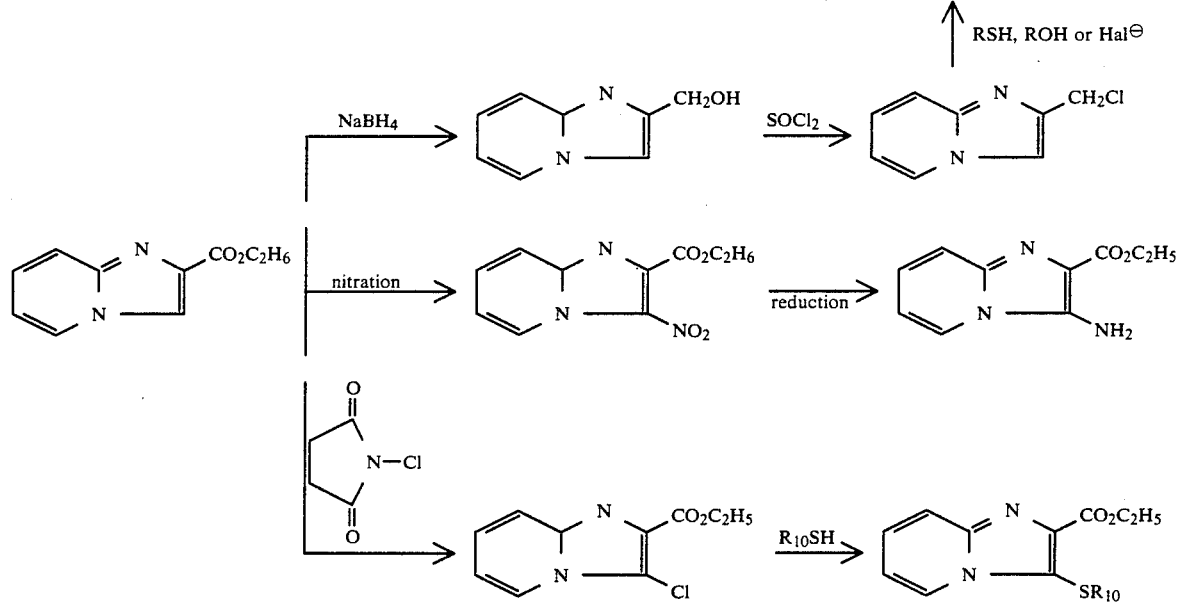
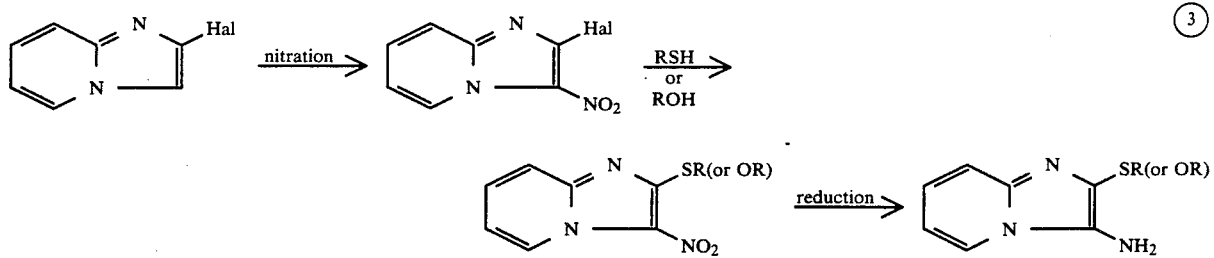
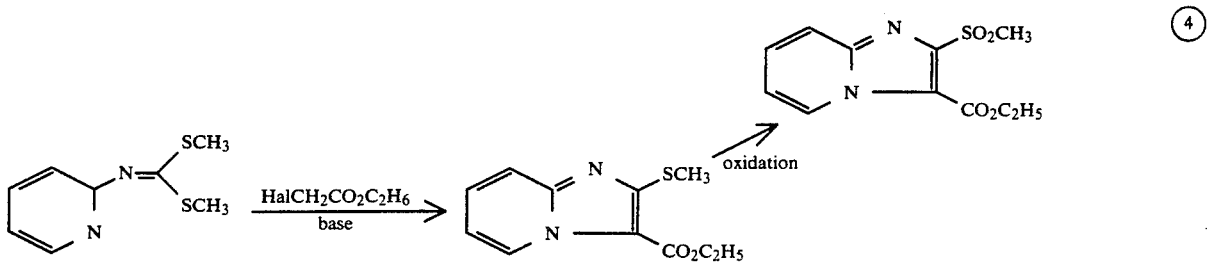

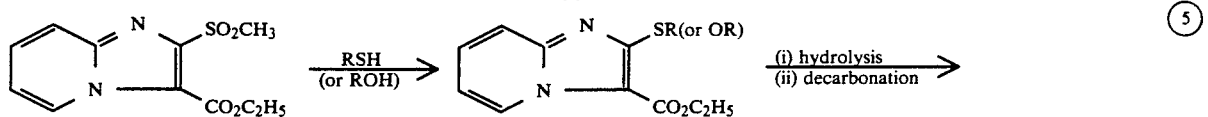
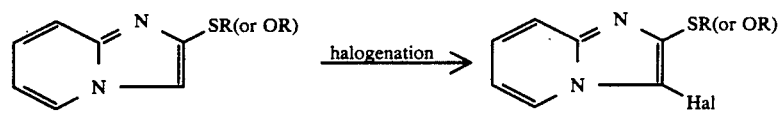
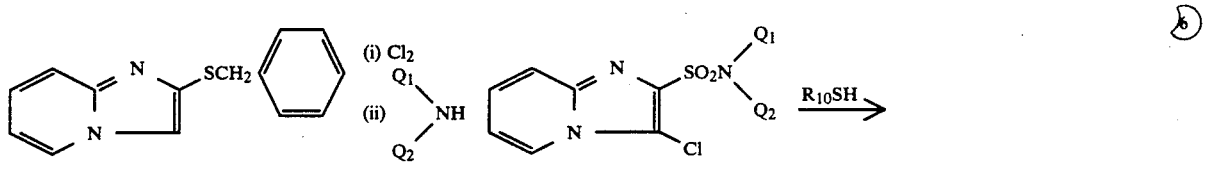
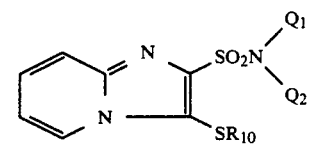
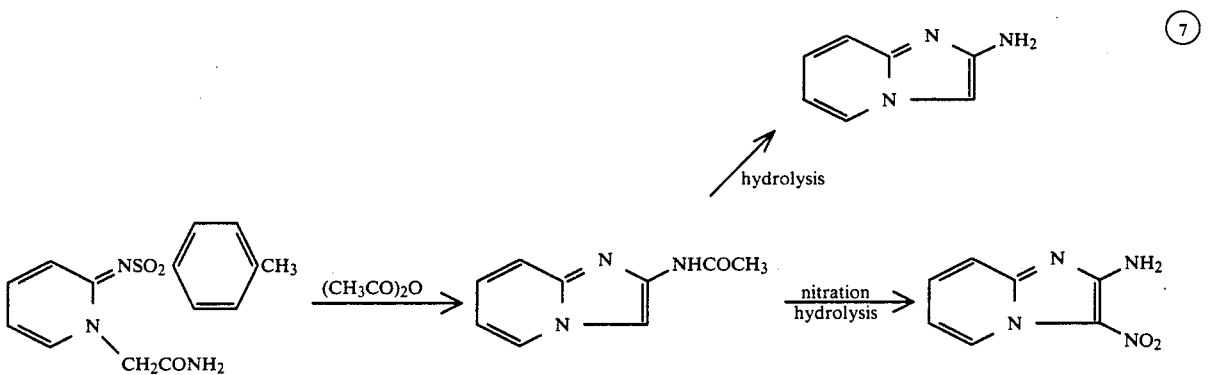
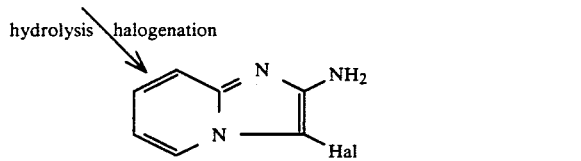
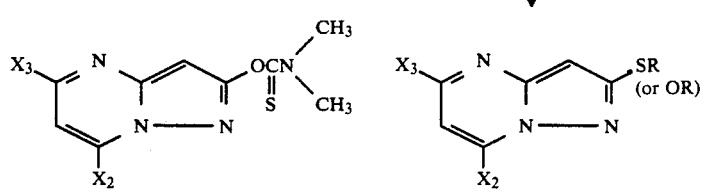

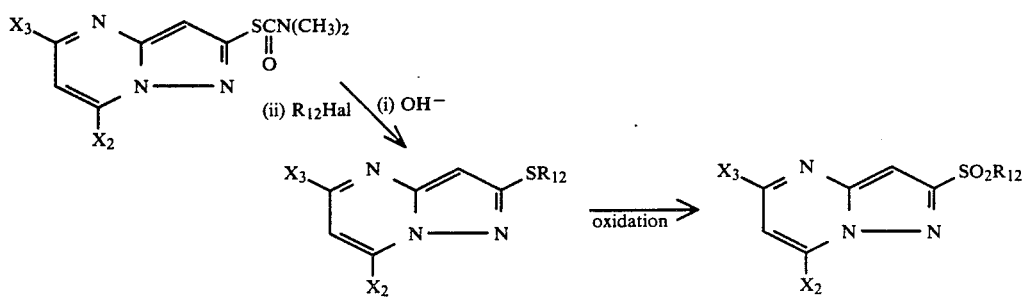
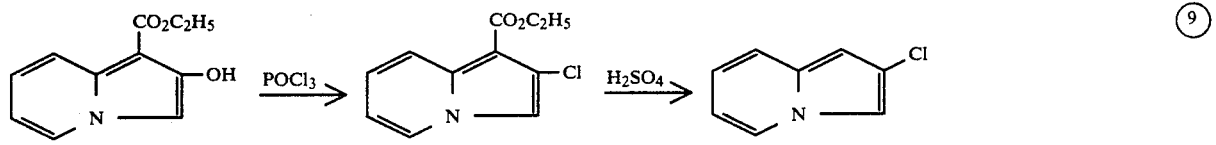
(9)
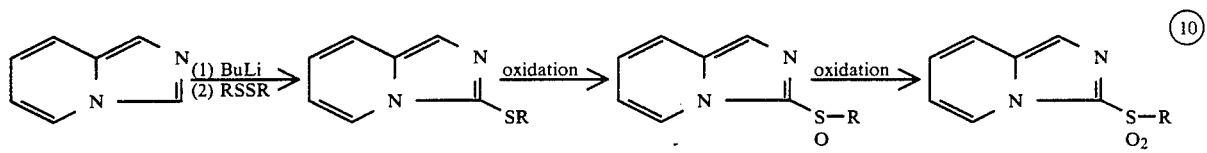
(10)
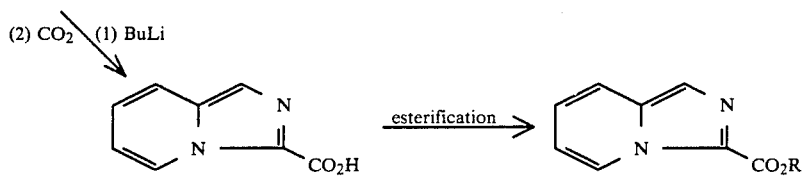
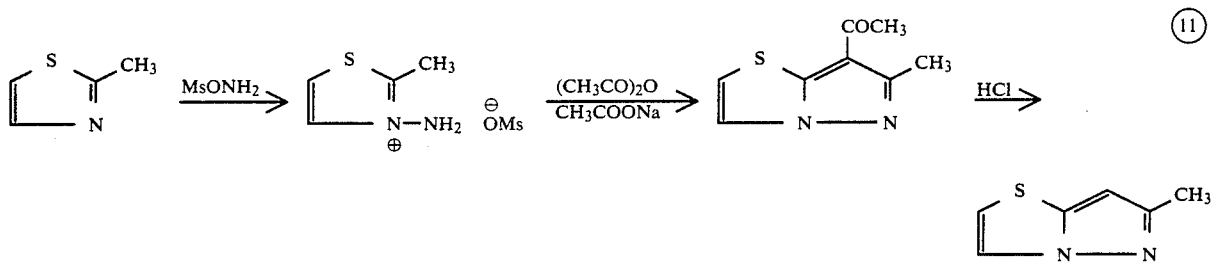
(11)
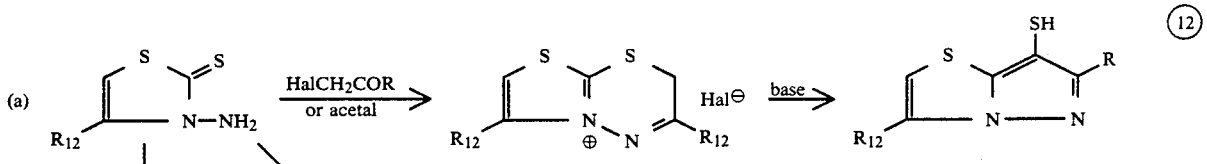
(12)
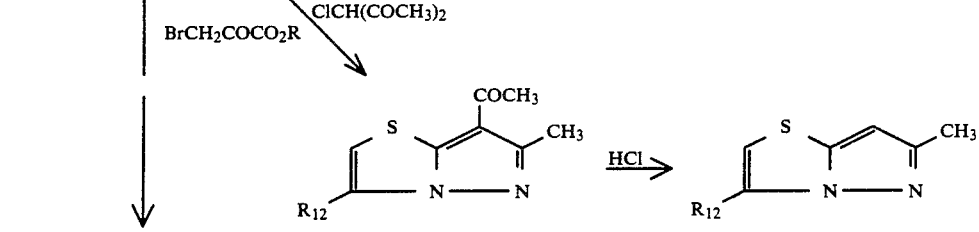
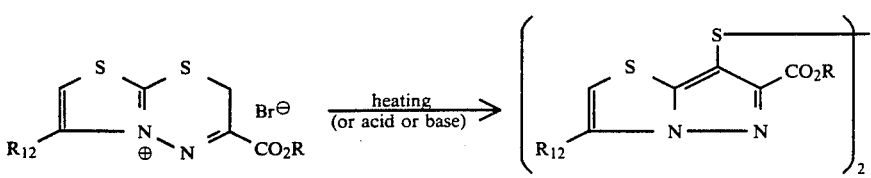

-continued

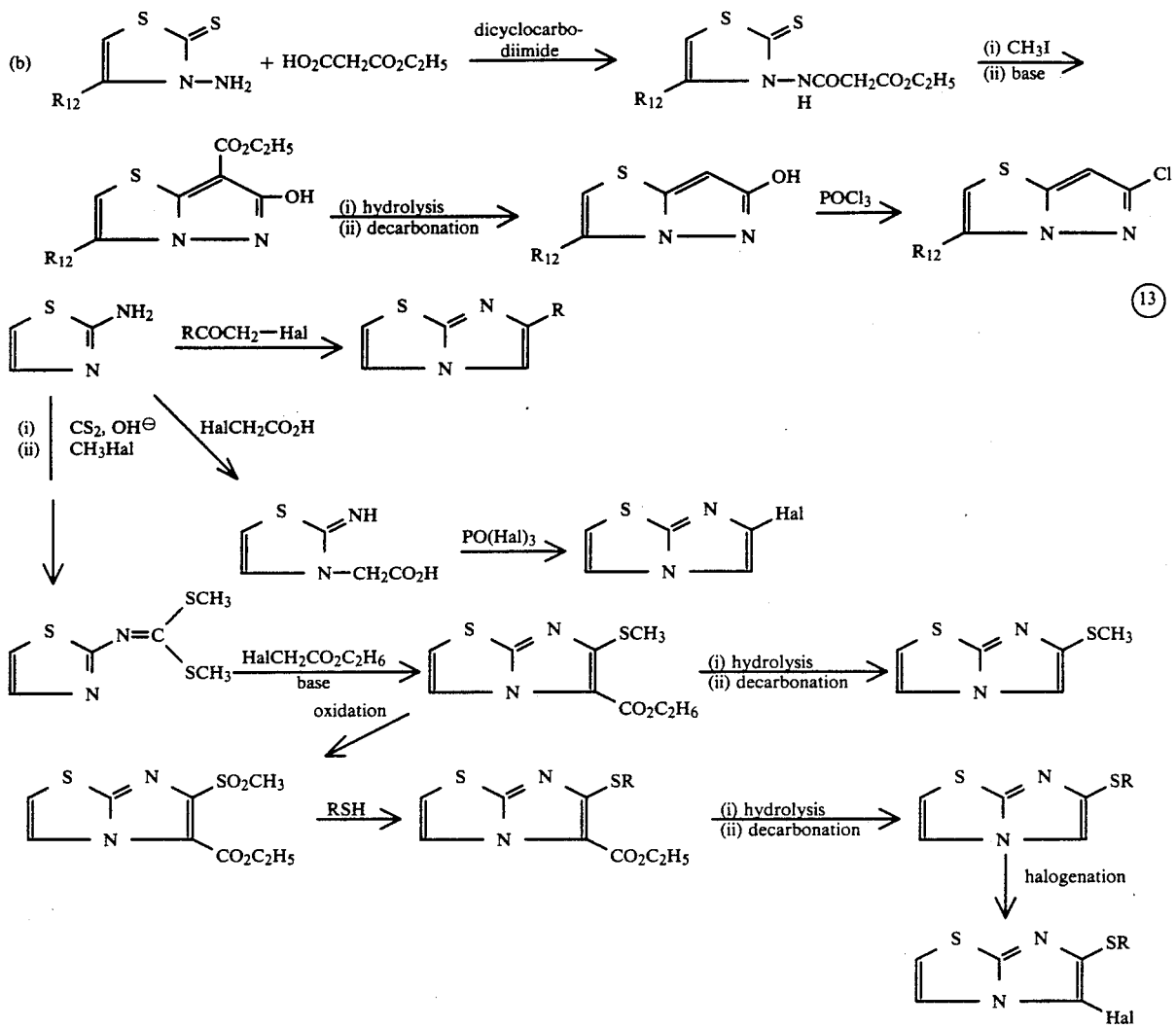

(wherein $R_{11}$ is an alkyl group containing 1 to 6 carbon atoms such as methyl, ethyl or propyl, hydrogen or hydroxy; and $R_{12}$ is an alkyl group containing 1 to 6 carbon atoms such as methyl, ethyl or propyl; $M_s$ is

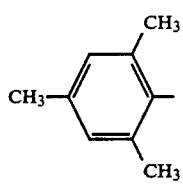

and the other symbols have the same meanings as defined above)

In the above mentioned reactions, those shown for imidazo[1,2-a]pyridine are similarly applicable to other condensed imidazoles such as imidazo[1,2-a]pyrimidine, imidazo [1,2-a]pyrazine, imidazo[1,2-b]pyridazine, imidazo[1,2-b](1,2,4) triazine, imidazo[1,2-a]imidazole, imidazo1,2-b]pyrazole, imidazo[2,1-b]thiazole or imidazo[2,1-b](1,3,4)thiadiazole (and also to other condensed heterocycles).

The compounds (I) or salt thereof in accordance with the present invention have an excellent herbicidal activity on a variety of weeds such as paddy weeds and field weeds in a very low application level, and show less damage on culture crops such as rice, wheat, barley, corn or soybean, and therefore exhibit an excellent selective herbicidal effect which is moreover long-lasting. They also can be very safely used as a herbicide for paddy, field, fruit garden or noncultivated field, showing substantially notoxicity on mammals or fishes and shell-fishes and withot causing environmental pollution.

This invention is illustrated in further detail in the Reference Examples, Examples and Formulation Examples.

The symbols in Reference Examples and Examples have the following meanings.

s: singlet, d: doublet, t: triplet, q: quartet, d,d: double doublet, m: multiplet, br: broad, J: coupling constant, DMSO: dimethylsulfoxide, ph: phenyl group The percentage (%) means % by weight, unless otherwise specified. Room temperature means usually about 10° to 30° C.

REFERENCE EXAMPLE 1

6-Chloro-2-methylimidazo [1,2-b]pyridazine

A solution of 13.0 g of 3-amino-6-chloropyridazine, 15.2 g of bromoacetone in 200 ml of propanol is heated under reflux for 3 hours. After cooling, the precipitated crystals are collected by filtration and dissolved in 100 ml of water. The solution is neutralized with potassium carbonate and the precipitated crystals are collected by filtration. Upon recrystallization from ethanol, it affords 8.2 g of the title compound having mp. 131° C.

6-Chloro-2-methylimidazo[1,2-a]pyridine having mp. 94°-96° C. is obtained in a similar way to Reference Example 1.

REFERENCE EXAMPLE 2

2-Ethylimidazo[2,1-b]thiazole

A solution of 3.0 g of 2-aminothiazole and 4.5 g of 1-bromo-2-butanone in 50 ml of acetone is heated under reflux for an hour and the precipitated crystals are collected by filtration. The crystals in 30 ml of aqueous HBr solution (1N) is heated at 80°-90° C. for an hour. After cooling, the reaction mixture is neutralized with 10% aqueous sodium hydroxide solution and extracted with dichloromethane. The extract is washed with water, dried over anhydrous sodium sulfate and distilled under reduced pressure to obtain 3.0 g of the title compound as an oil.

NMR(CDCl$_3$)δ: 1.27(t,3H), 2.72 (q,2H), 6.71(d,1H), 7.20(s,1H), 7.92(d,1H).

The below mentioned compounds are obtained in a similar way to Reference Example 2.

6-(n-propyl)imidazo[2,1-b]thiazole (oil):
NMR(CDCl$_3$)δ: 0.96(t,3H), 1.74(m,2H), 2.66(t,2H), 6.71(d,1H), 7.20(s,1H), 7.33(d,1H).

2-trifluoromethylimidazo[1,2-a]pyridine (crystalline solid):
NMR(CDCl$_3$)δ: 6.86(t,1H), 7.23(t,1H), 7.60(d,1H) 7.82(s,1H), 8.14(d,1H).

6-trifluoromethylimidazo[2,1-b]thiazole (crystals): mp. 67°-68° C.

REFERENCE EXAMPLE 3

2-Bromoimidazo[1,2-a]pyridine

To 44.0 g of melted phosphorus oxybromide, 12.0 g of 2-hydroxyimidazo[1,2-a]pyridine is added at 60°-85° C. and stirred for 3 hours at 90° C. The mixture is poured into 300 ml of ice water, neutralized with aqueous ammonia and then extracted with chloroform. The collected chloroform layer is dried over anhydrous sodium sulfate. Chloroform is distilled off and the residue is purified by silica gel chromatography (eluent: chloroform) to obtain 3.5 g of the title compound as a crystalline solid.

NMR(CDCl$_3$)δ: 6.74(t,1H), 7.13(t,1H), 7.43(d,1H), 8.05(d,1H).

REFERENCE EXAMPLE 4

6-Bromoimidazo[2,1-b]thiazole

A mixture of 10.0 g of 2-imino-4-thiazolin-3-yl-acetic acid hydrobromide and 30.0 g of phosphorus oxybromide is heated for 2 hours at 140° C. After cooling, the reaction mixture is poured into ice water, neutralized with 10% sodium hydroxide solution and filtered to collect the precipitated crystals. The crystals are recrystallized from toluene to afford the title compound of mp. 96°-98° C.

REFERENCE EXAMPLE 5

Ethyl 2-ethylthioimidazo[1,2-a]pyridine-3-carboxylate

60% oily sodium hydride (2.6 g) is suspended in 50 ml of dimethylformamide. A solution of 4.0 g of ethylmercaptan in 50 ml of dimethylformamide is dropwise added to the suspension under cooling and stirred for an hour at 10°-20° C. Then, 16.2 g of ethyl 2-methylsulfonylimidazo [1,2-a]pyridine-3-carboxylate are added to the mixture and stirred for 4 hours at room temperature. The reaction mixture is poured into 500 ml of ice water and extracted with chloroform. The separated chloroform layer is dried over anhydrous sodium sulfate and distilled to remove chloroform. The residue is purified by silica gel chromatography (eluent: ethyl acetate) to afford 9.7 g of the title compound of mp. 71°-73° C.

NMR(CDCl$_3$)δ: 1.41(t,6H), 3.25(q,2H), 4.40(q,2H), 6.88(t,1H), 7.30(t,1H), 7.55(d,1H), 9.20(d,1H).

REFERENCE EXAMPLE 6

Ethyl 2-n-propylthioimidazo[1,2-a]pyridine-3-carboxylate

The title compound is obtained from ethyl 2-methylsulfonylimidazo[1,2-a]pyridine-3-carboxylate and n-propyl-mercaptan in a similar way to Reference Example 5. mp. 50°-51° C.

NMR(CDCl$_3$)δ: 1.10(t,3H), 1.50(t,3H), 1.78-2.05 (m,2H), 3.31(t,2H), 4.48(q,2H), 6.95 (t,1H), 7.38(t,1H), 7.60(d,1H), 9.28 (d,1H).

REFERENCE EXAMPLE 7

Ethyl 2-ethylthioimidazo[1,2-a]pyridine-3-carboxylate

To a solution of 4.3 g of ethyl 2-ethylthioimidazo [1,2-a]pyridine-3-carboxylate in 20 ml of ethanol, 20 ml of 20% aqueous sodium hydroxide solution are added and stirred for 40 minutes at 80° C. The reaction mixture is concentrated under reduced pressure and the resulting residue is dissolved in 40 ml of water. The precipitated crystals upon neutralization with hydrochliric acid are collected by filtration, washed with water and dried to afford 3.8 g of the title compound

REFERENCE EXAMPLE 8

2-Ethylthioimidazo[1,2-a]pyridine

2-Ethylthioimidazo 1,2-a pyridine-3-carboxylic acid (3.8 g) is heated for 20 minutes at 130° C., during which violent foaming occurs and an oily substance appears. After cooling, the oily substance is dissolved in chloroform, and the chloroform layer is washed with water and dried over anhydrous sodium sulfate. Chloroform is removed under reduced pressure to give 3.0 g of the oily title compound.

NMR(CDCL$_3$)δ: 1.35(t,3H), 3.10(q,2H), 6.72(t,1H), 7.10(t,1H), 7.50(s,1H), 7.52(d,1H), 8.00(d,1H).

REFERENCE EXAMPLE 9

2-(n-Propylthio)imidazo[1,2-a]pyridine

The title compound is obtained as a brown oily substance from ethyl 2-(n-propylthio)imidazo[1,2-a]pyridin-3-carboxylate in a similar way to Reference Example 7 and 8.

NMR(CDCl$_3$)δ: 1.05(t,3H), 1.50-1.98(m,2H), 3.05(t,2H), 6.78(t,1H), 7.18(t,1H), 7.55(s,1H), 7.60(d,1H), 8.05(d,1H).

REFERENCE EXAMPLE 10

Ethyl 6-methylthioimidazo[2,1-b]thiazole-5-carboxylate (1) To a solution of 20.0 g of 2-aminothiazole and 15.2 g of carbon disulfide in 200 ml of dimethylformamide is added 35.0 g of powdery potassium hydroxide under cooling to 10-°15° C. during 30 minutes. The mixture is further stirred at the above temperature for 30 minutes and then at room temperature for an hour, followed by addition of 500 ml of ether. The precipitated crystals are collected by filtration and suspended in 250 ml of ethanol. To this suspension, 50.6 g of methyl iodide are added at 20-°45° C. and stirred for 2 hours at room temperature. The precipitate is filtered off and the filtrate is concentrated under reduced pressure. The residue is purified by silica gel chromatography (eluent: chloroform) to give 29.0 g of dimethyl N-(2-thiazolyl) dithiocarboimidate as an oil.

NMR(CDCl$_3$)δ: 2.55(s,6H), 7.02(d,1H), 7.51(d,1H).

(2) A solution of 29.0 g of dimethyl N-(2-thiazolyl)-dithiocarboimidate and 28.5 g of ethyl bromoacetate in 100 ml acetone is heated under reflux for 6 hours. The resulting crystals are collected by filtration and suspended in 400 ml of tetrahydrofuran. To the suspension is added 6.9 g of 60% oily sodium hydride under nitrogen gas atmosphere and the mixture is stirred for 30 minutes. After adding 40 ml of dimethyl formamide, the mixture is further stirred for 10 hours at room temperature and allowed to stand overnight. The mixture is filtered to remove insoluble substance. The filtrare is concentrated under reduced pressure and purified by silica gel chromatography (eluent: chloroform) to obtain 9.3 g of the title compound as colorless crystals, mp 133°-135° C.

NMR(CDCl$_3$)δ: 1.41(t,3H), 2.63 (s,3H), 4.42(q,2H), 6.90(d,1H), 8.02(d,1H).

REFERENCE EXAMPLE 11

6-Methylthioimidazo [2,1-b]thiazole

To a suspension of 5.4 g of ethyl 6-methylthioimidazo [2,1-b]thiazole-5-carboxylate in 20 ml of ethanol is added 20 ml of 30% aqueous sodium hydroxide solution and the mixture is heated under reflux for an hour. The reaction solution is concentrated, followed by addition of water and adjustment with hydrochloric acid to pH 1 - 2 to precipitate the crystals. The crystals are collected by filtration, washed with water, dried and heated on oil bath at 150°-160° C. for 30 minutes which violent foaming occurs and an oily substance appears. The oily substance is dissolved in chloroform, and the solution is washed with water and dried over anhydrous magnesium sulfate. Chloroform is distilled off to obtain 3.8 g of the title compound as a oil.

NMR(CDCl$_3$): 2.44(s,3H), 6.78(d,1H), 7.32(s,1H), 7.37(d,1H).

REFERENCE EXAMPLE 12

Ethyl 6-Methylsulfonylimidazo[2,1-b]thiazole-5-carboxylate

To a suspension of 10.0 g of ethyl 6-methylthioimidazo [2,1-b]thiazole-5-carboxylate in 100 ml of acetonitrile is gradually added 21.0 g of m-chloroperbenzoic acid at a temperature below 115° C. After stirring for 2 hours at room temperature., the reaction mixture is concentrated under reduced pressure to make about a half volume. The residue is poured into 5% aqueous potassium carbonate solution and extracted with ethyl acetate. Ethyl acetate is distilled off from the collected ethyl acetate layer and the residue is crystallized from ethanol to obtain 10.0 g of the title compound as colorless needlecrystals. mp. 158°-161° C.

REFERENCE EXAMPLE 13

Ethyl 6-benzylthioimidazo[2,1-b]thiazole-3-carboxylate

Ethyl 6-methylsulfonylimidazo[2,1-b]thiazole-5-carboxylate (5.9 g) is dissolved in 100 ml of tetrahydrofuran. A suspension of sodium benzylmercaptide in tetrahydrofuran (prepared from 1.0 g of 60% oily sodium hydride, 2.9 g of benzylmercaptan and 50 ml of tetrahydrofuran) is added to the above solution and stirred for 30 minutes at room temperature. The reaction solution is concentrated under reduced pressure, and the residue after addition of water is extracted with ethyl acetate. The extract is washed with water and dried over anhydrous magnesium sulfate. After distilling ethyl acetate off, the residue is purified by silica gel chromatography (eluent: dichloromethane-ethyl acetate) to give 6.4 g of the crystalline title compound, mp. 83°-84° C.

NMR(CDCl$_3$)δ: 1.37(t,3H), 4.37(q,2H), 4.49(s,2H), 6.88(d,1H), 7.20-7.60(m,5H), 8.02(d,1H).

REFERENCE EXAMPLE 14

6-Benzylthioimidazo[2,1-b]thiazole-5-carboxylic acid

To a solution of 3.5 g of ethyl 6-benzylthioimidazo [2,1-b]thiazole-5-carboxylate in 25 ml of ethanol is added sodium hydroxide solution (prepared by dissolving 1.5 g of sodium hydroxide in 7 ml of water) and the mixture is stirred for 30 minutes at 50°-60° C. and then under reflux for 20 minutes. The reaction solution is concentrated, added with 70 ml of water and adjusted to pH 3 by addition of hydrochloric acid. The precipitate is collected by filtration and dried to obtain 3.0 g of the title compound, mp. 147°-150° C. (decomp.).

REFERENCE EXAMPLE 15

6-Benzylthioimidazo[2,1-b]thiazole

6-Benzylthioimidazo[2,1-b]thiazole-5-carboxylic acid (3.0 g) is heated for 40 minutes at 140°-160° C. and the resulting oil is purified by silica gel chromatography (eluent: dichloromethane - diisopropylether) to obtain 2.55 g of the title compound, mp. 76°-77° C.

NMR(CDCl$_3$)δ: 4.14(s,2H), 6.77(d,1H), 7.2-7.4(m,7H).

REFERENCE EXAMPLE 16

6-Benzylthio-5-chloroimidazo[2,1-b]thiazole

6-Benzylthioimidazo[2,1-b]thiazole (2.0 g) is dissolved in a mixture of 8 ml of dichloromethane and 40 ml of carbon tetrachloride. N-Chlorosuccinimide (1.2 g) is added to the solution during 10 minutes and stirred for an hour at room temperature. The insoluble product is filtered off and the filtrate is purified by silica gel chromatography (eluent: ethylacetate) to give 2.0 g of the title compound as an oil.

NMR(CDCl$_3$)δ: 4.13(s,2H), 6.82(d,1H), 7.1-7.4(m,6H).

REFERENCE EXAMPLE 17

Ethyl 6-(p-methoxybenzylthio)imidazo[2,1-b]thiazole-5-carboxylate

The title compound is obtained from 6-methylsulfonyl imidazo[2,1-b]thiazole and p-methoxybenzylmercaptan in a similar way to Reference Example 13. mp. 103°-105° C.

NMR(CDCl$_3$)δ: 1.40(t,3H), 3.80(s,3H), 4.40(q,2H), 4.48(s,2H), 6.8-7.4(m,5H), 8.05(d,1H).

REFERENCE EXAMPLE 18

2-Fluoromethylimidazo[1,2-a]pyridine

To a solution of 3.7 g of 2-chloromethylimidazo [1,2-]pyridine in 6 ml of sulfolane is added 6.0 g of potassium fluoride and 0.5 g of 18-crown-6-ether and the mixture is stirred for 15 hours at 120° C. After cooling, the reaction solution is poured into 300 ml of water and extracted with chloroform. The extract is concentrated and the residue is purified by silica gel chromatography (eluent: chloroform) to give 0.5 g of the title compound as an oil.

NMR(CDCl$_3$)δ:5.53(d,2H), 6.78(t,1H), 7.18(t,1H), 7.4–7.8(m,2H), 8.12(d,1H).

REFERENCE EXAMPLE 19

2-Methoxymethylimidazo[1,2-a]pyridine

To a solution of 3.0 g of 2-chloromethylimidazo [1,2-a]pyridine in 50 ml of methanol is added 1.1 g of sodium methoxide, followed by heating under reflux for 3 hours. Methanol is distilled off under reduced pressure and chloroform is added to the residue. The resulting insoluble substance is filtered off, and the filtrate is washed with water and dried over anhydrous sodium sulfate. After distilling chloroform off, 2.9 g of the title compound is obtained as crystals.

NMR(CDCl$_3$)δ: 3.48(s,3H), 4.65(s,2H), 6.72(t,1H), 7.14(t,1H), 7.35–7.65(m,2H), 8.05 (d,1H).

REFERENCE EXAMPLE 20

2-Methylthiomethylimidazo[1,2-a]pyridine

The title compound as crystals is obtained from 2-chloromethylimidazo[1,2-a]pyridine and sodium thiomethoxide by a similar method to Reference Example 19.

NMR(CDCl$_3$)δ: 2.15(s,3H), 3.89(s,3H), 6.78(t,1H), 7.18(t,1H), 7.55(s,1H), 7.58(d,1H), 8.10(d,1H).

REFERENCE EXAMPLE 21

2,6-Dichloroimidazo[1,2-b]pyridazine (1) A solution of 13.0 g of 3-amino-6-chloropyridazine and 16.7 g of ethyl bromoacetate in 150 ml of acetonitrile is heated under reflux for 4 hours. After cooling, the precipitate is collected by filtration, added with 30% sodium hydroxide and stirred for 3 hours at 90° C. After cooling, the precipitate is collected by filtration to give 16.0 g of sodium salt of 6-chloro-2-hydroxyimidazo[1,2-b]pyridazine.

(2) Sodium salt of 6-chloro-2-hydroxyimidazo [1,2-b]pyridazine (16.0 g) is gradually added to 100 ml of phosphorus oxychloride and heated under reflux for 5 hours. The mixture is distilled under reduced pressure to remove about two-thirds amount of phosphorus oxychloride used, and the residue is poured into ice water, neutralized with aqueous ammonia and extracted with chloroform. The extract is dried over anydrous sodium sulfate and distilled to remove chloroform. The residue then is purified by silica gel chromatography (eluent: dichloromethane) to give 1.5 g of the title compound as crystals.

NMR(CDCl$_3$)δ: 7.15(d,1H), 7.75–7.95(m,2H).

REFERENCE EXAMPLE 22

2,5,7-Trimethylpyrazolo[1,5-a]pyrimidine

A mixture of 9.7 g of 3-amino-5-methylpyrazole, 13 ml of acetylacetone and 50 ml of isopropanol is heated under reflux for 3 hours. After distilling isopropanol off, the residue is dissolved in dichloromethane, washed with water and dried over anhydrous magnesium sulfate when chloroform is distilled off, 12.7 g of the title compound is obtained as crystals. mp. 70°–73° C.

REFERENCE EXAMPLE 23

2-Methylpyrazolo[1,5-a]pyrimidine

3-Amino-5-methylpyrazole is reacted with 1,1,3,3-tetramethoxypropane under an acidic condition of hydrochloric acid and treated in a similar way to Reference Example 22 to give the title compound as a crystal. mp. 54°–57° C.

NMR(CDCl$_3$)δ:2.52(s,3H), 6.47(s,1H), 6.6–6.8(m,1H), 8.4–8.65(m,2H).

REFERENCE EXAMPLE 24

2-Ethylthio-5,7-dimethylpyrazolo[1,5-a]pyrimidine

60% oily sodium hydride (2.0 g) is suspended in 20 ml of dimethylformamide. A solution of 3.7 ml of ethylmercaptan dissolved in 10 ml of dimethylformamide under ice cooling is added to the suspension below 10° C. and stirred for 30 minutes at room temperature. 2-Chloro-5,7-dimethylpyrazolo [1,5-a]pyrimidine (6.6 g) is added to the mixture and stirred for 5 hours at 80°–90° C. After cooling, the reaction solution is poured into ice water and extracted with toluene. The extract is washed with water and then distilled to remove the solvent. The residue is purified by silica gel chromatography (eluent: dichloromethane) to give 4.0 g of the title compound as an oil.

NMR(CDCl$_3$)δ:1.40(t,3H), 2.49(s,3H), 2.66(s,3H), 3.12(q,2H), 6.4–6.6(m,2H).

REFERENCE EXAMPLE 25

2-Methylthio-5,7-dimethylpyrazolo[1,5-a]pyrimidine (1) 60% oily sodium hydride (3.9 g) is suspended in 100 ml of dimethylformamide, to which 22.8 g of 2-hydroxy-5,7-dimethylpyrazolo[1,5-a]pyrimidine is added under cooling to maintain the reaction solution at 20°–30° C. and then stirred for 30 minutes at the above temperature. To the reaction solution, 22.5 g of dimethylthiocarbamoyl chloride is added during 1.5 hours and then stirred for 2 hours at 70°–80° C. After cooling, 800 ml of 1% aqueous potassium hydroxide solution is added to the reaction solution and stirred for 30 minutes at room temperature. The precipitate as collected by filtration is recrystallized from ethanol to give 18.5 g of 2-(N,N-dimethyl thiocarbamoyloxy)-5,7-dimethylpyrazolo[1,5-a]pyrimidine. mp. 216°–217° C.

NMR(CDCl$_3$)δ:2.50(s,3H), 2.65(s,3H), 3.36(s,3H), 3.42(s,3H), 6.30(s,1H), 6.50(s,1H).

(2) 2-(N,N-dimethylthiocarbamoyloxy)-5,7-dimethylpyrazolo[1,5-a]pyrimidine (10.0 g) is heated for 1.5 hours at 230°–250° C. (thermal rearrangement). After cooling, it is purified by silica gel chromatography (eluent: acetone-chloroform) to give 3.4 g of 2-(N,N-dimethylcarbamoylthio)-5,7-dimethylpyrazolo[1,5-a]pyrimidine. This compound is dissolved in 25 ml of methanol, to which a solution of 1.5 g of potassium hydroxide in 3 ml of water is added and refluxed for an hour. After cooling, 1 ml of methyl iodide is added to the reaction mixture and refluxed for 2 hours at room temperature. The reaction mixture then is concentrated. After adding water, the residue is extracted with chloroform, and the extract is washed with water and dried over anhydrous magnesium sulfate. Chloroform is distilled off to give 2.0 g of the oily title compound.

NMR(CDCl₃)δ: 2.50(s,3H), 2.61(s,3H), 2.69(s,3H), 6.41(s,1H), 6.45(s,1H).

REFERENCE EXAMPLE 26

7-Acetyl-3,6-dimethylprazolo[5,1-b]thiazole

A solution of 29.3 g of 3-amino-4-methylthiazolin2-thione and 28.0 g of 3-chloro-2,4-pentadione in 500 ml of ethyl acetate is refluxed for 5 hours. Resinous substance is removed by decantation from the hot reaction mixture. To the resulting supernatant, a small amount of ethanol is added and the precipitate formed is removed by filtration. The filtrate is concentrated under reduced pressure and the residual solid is recrystallized from diisopropyl ether to give 30.7 g of the title compound. mp. 124° C.

REFERENCE EXAMPLE 27

3,6-Dimethylpyrazolo[5,1-b]thiazole

A mixture of 25.0 g of 7-acetyl-3,6-dimethylpyrazolo [5,1-b]thiazole and 200 ml of concentrated hydrochloric acid is refluxed for 10 hours. The reaction solution is concentrated, and the residue is neutralized with 10% sodium hydroxide and then extracted with chloroform. The extract is washed with water, dried over anhydrous sodium sulfate and distilled to remove chloroform. The residue is purified by silica gel chromatography (eluent: dichloromethanemethanol) to give 16.3 g of the oily title compound.

NMR(CDCl₃)δ: 2.39(s,3H), 2.42(d,3H), 6.07(s,1H), 6.19-6.31(m,1H).

REFERENCE EXAMPLE 28

7-Mercapto-3 TM methylpyrazole[5,1-b]thiazole

A solution of 13.7 g of 3-amino-4-methylthiazolin-2-thione and 19.0 g of 2-bromo-1,1-dimethoxythane in 100 ml of dioxane is refluxed for 2 hours. After cooling, the precipitate is collected by filtration and dissolved in 300 ml of methanol. To the solution, 48.0 g of 28% sodium methylate solution is gradually added, stirred for 30 minutes at room temperature and then concentrated under reduced pressure. The residue is dissolved in 150 ml of water, acidified with hydrochloric acid and extracted with chloroform. After removing chloroform, the rsidue is purified by silica gel chromatography (eluent: chloroform-methanol) to give 4.5 g of the title compound.

NMR(CDCl₃)δ: 2.49(d,3H), 2.93(s,1H), 6.47-6.53 (m,1H), 7.80(s,1H).

REFERENCE EXAMPLE 29

Bis-(6-methoxycarbonyl-3-methylpyrazolo[5,1-b]thiazol-7-yl)disulfide

A solution of 16.0 g of 3-amino-4-methylthiazolin-2-thione and 19.5 g of methyl bromopyruvate in 400 ml of ethyl acetate is refluxed for 2 hours. After cooling, the precipitate is collected by filtration and dissolved in 200 ml of methanol. To this solution, a solution of 9.8 g of potassium acetate in 30 ml of water is added, and stirred for 10 hours at room temperature. The precipitate collected by filtration is purified by silica gel chromatography (eluent: chloroform-methanol) to give 2.0 g of the title compound. Upon recrystallization from ethyl acetate, it gives crystals of mp. 193°-194° C.

NMR(CDCl₃)δ: 2.53(s,6H), 3.96(s,6H), 6.65(s,2H).

REFERENCE EXAMPLE 30

Bis-(6-ethoxycarbonyl-3-methylpyrazolo[5,1-b]thiazol-7-yl)disulfide

The title compound is obtained form 3-amino-4-methylthiazolin-2-thione and ethyl bromopyruyate in a similar way to Reference Example 29.

NMR(CDCl₃)δ: 1.40(t,6H), 2.50(s,6H), 4.43(q,4H) 6.59(s,2H).

REFERENCE EXAMPLE 31

2,6-Dichloroimidazo[1,2-a]pyridine

Chloroacetic acid (9.5 g) is dissolved in 70 ml of acetonitrile, to which 10.1 g of triethylamine is portionwise added and further 12.9 g of 2-amino-5-chloropyridine is added. The mixture is refluxed for 3 hours. After cooling, the precipitated 2-imino-5-chloro-1,2-dihydropyridin-1-ylacetic acid as crystals is collected by filtration and dried. The crystals are added to 40 ml of phosphorus oxychoride and refluxed for 5 hours. After cooling, the reaction mixture is poured into ice water and neutralized with aqueous ammonia. The precipitate collected by filtration is purified by silica gel chromatography(eluent: ethyl acetate) to give 2.1 g of the title compound as crystals. mp. 155°-156° C.

NMR(CDCl₃)δ:7.19(d,2H), 7.48(d,1H), 7.50(s,1H), 8.15(s,1H).

REFERENCE EXAMPLE 32

3-Methylthioimidazo[1,5-a]pyridine

To a solution of 1.63 g of imidazo[1,5-a]pyridine in 20 ml of tetrahydrofuran, 11 ml of n-butyl lithium (1.6N-hexane solution) is added below 70° C. during 15 minutes under nitrogen gas atmosphere. After stirring the mixture for an hour at the same temperature, a solution of 1.7 g of dimethyldisulfide in 10 ml of tetrahydrofuran is dropwise added during 30 minutes and continued to stir for 30 minutes. The mixture added with water is extracted with ether. The extract is dried over anhydrous magnesium sulfate and distilled to remove ether. The residue is purified by silica gel chromatography (eluent: chlooform-ethylacetate) to give 2.37 g of the oily title compound.

NMR(CDCl₃)δ: 2.52(s,3H), 6.8-6.5(m,2H), 7.40(d,1H), 7.49(s,1H), 8.06(d,1H).

REFERENCE EXAMPLE 33

Ethyl 2-chloropyrrolo[1,2-a]pyridin-1-carboxylate

To a solution of 3.0 g of ethyl 2-hydroxypyrrolo [1,2-a]pyridine-1-carboxylate in 50 ml of acetonitrile, 2.7 g of phosphorus oxychloride is added at room temperature and stirred for 2 hours. The reaction mixture is concentrated under reduced pressure, added with water and then extracted with dichloromethane. The extract is dried on anhydrous sodium sulfate and distilled to remove dichloromethane. The residue is purified by silica gel chromatography (eluent: n-hexane-ethyl acetate) to give 2.0 g of the title compound as crystals.

NMR(CDCl₃)δ: 1.40(t,3H), 4.38(q,2H), 7.18-6.58 (m,2H), 7.23(s,1H), 7.87(d,1H), 8.13(d,1H).

REFERENCE EXAMPLE 34

2-Chloropyrrolo[1,2-a]pyridine

To a suspension of 0.20 g of ethyl 2-chloropyrolo [1,2-a]pyridin-1-carboxylate in 10 ml of water, 1.5 ml of sulfuric acid is added and refluxed for 3 hours. After cooling, the mixture is neutralized with an aqueous saturated sodium hydrogen carbonate solution and extracted with ethyl acetate. The extract is dried on anhydrous sodium sulfate and distilled to remove ethyl acetate. The residue is purified by silica gel chromatography (eluent: ethyl acetate-hexane) to give crystals of the title compound NMR(CDCl$_3$)δ: 6.33(s,1H), 6.42–6.80(m,2H), 7.21(s,1H), 7.25(d,1H), 7.76(d,1H)

The following shows new condensed heterocyclic compounds which may be prepared in a similar way to Reference Examples 1-34.

| Structural formula | NMR(CDCl$_3$, δ) or mp.(°C.) |
|---|---|
| (pyridine fused imidazole with SCH$_3$) | 2.59(s,3H),6.70(m,1H), 7.15(m,1H),7.45(S,2H) 8.0(d,1H) |
| (5-CH$_3$ pyridine fused with Cl) | 88–90 |
| (5-CF$_3$ pyridine fused with Cl) | 116–118 |
| (S,N bicyclic with CH$_2$Cl) | 4.66(s,2H),6.80(d,1H) 7.38(d,1H),7.50(s,1H) |
| (CH$_3$, CF$_3$ pyrazolo-pyrimidine) | * |
| (CH$_3$, CH$_3$ pyrazolo-pyrimidine with O–SO$_2$–C$_6$H$_4$–CH$_3$) | 2.43(s,3H),2.47(s,3H) 2.53(s,3H),6.14(s,1H) 6.8(s,1H),7.45(d,2H), 7.86(d,2H) |
| (CH$_3$, CH$_3$ pyrazolo-pyrimidine with SC$_3$H$_7$-n) | * |
| (CH$_3$, CH$_3$ pyrazolo-pyrimidine with SC$_4$H$_9$-n) | 0.93(t,3H),1.25–1.90 (m,4H),2.53(s,3H), 2.69(s,3H),3.13(t,2H) 6.48(s,2H), |
| (CH$_3$, CH$_3$ pyrazolo-pyrimidine with SCH$_2$CH=CH$_2$) | 2.51(s,3H),2.68(s,3H) 3.76(d,2H),5.11(d,1H) 5,26(d,1H),5.68–6.25 (m,1H),6.47(s,2H) |
| (CH$_3$, CH$_3$ with S, N–N, SH) | 217–218 |

(In the above table, the compound marked with * is subjected to the subsequent reaction without isolation and its structure is confirmed as sulfonamide compound.)

REFERENCE EXAMPLE 35

2-Chloroimidazo[1,2-a]pyridine-3-sulfonic acid

A solution of 4.6 ml of chlorosulfonic acid in 10 ml of chloroform is dropwise added to a solution of 3.5 g of 2-chloroimidazo[1,2-a]pyridine in 20 ml of chloroform during 30 minutes. The mixture is heated under reflux for 6 hours with stirring to afford the viscous oily substance. To the oily substance which is separated from the supernatant, ether and a small amount of ethanol are added to afford crystals, which are collected by filtration and dried to give 5.1 g of 1/2 hydrate of the title compound.

NMR(DMSO-$d_6$)$\delta$: 7.21–7.45(m,1H), 7.62–7.80(m,2H), 8.9(d,1H), 9.4(s,2H).

Tables 1–7 show the sulfonic acids prepared in a similar way to Reference Example 35. In the tables, the compound marked with ** is used to the subsequent reaction without isolation and its structure is confirmed as sulfonic acid compound or object compound.

TABLE 1

General formula (pyridine fused imidazole with $R_0$, $R_1$, $SO_3H$)

| $R_0$ | $R_1$ | NMR(DMSO-$d_6$)$\delta$ |
|---|---|---|
| H | H | 7.5~7.8(m,1H),8.0~8.1(m,2H), 8.30(s,1H),9.02(d,1H) |
| CH$_3$ | H | 2.78(s,3H),7.5~7.7(m,1H),7.9~8.1(m,2H),9.05(d,1H) |
| CH$_2$Cl | H | 5.15(s,2H),7.35~7.60(m,1H),7.7~8.0(m,2H),8.97(d,1H) |
| CH$_2$F | H | ** |
| CH$_2$OCH$_3$ | H | 3.45(s,3H),4.99(s,2H),7.60(t,1H), 7.83~8.14(m,2H),9.07(d,1H), |
| CH$_2$SCH$_3$ | H | ** |
| CH$_2$SC$_2$H$_5$ | H | ** |
| CF$_3$ | H | 7.1~7.3(m,1H),7.4~7.7(m,2H),8.92(d,1H) |
| Ph | H | ** |
| SCH$_3$ | H | 2.68(s,1H),7.4~7.6(m,1H),7.75~8.9(m,2H),8.98(d,1H) |
| SC$_2$H$_5$ | H | 1.30(t,3H),3.20(q,2H),7.4~7.6(m,1H),7.75~7.95(m,2H),9.01(d,1H), |
| SC$_3$H$_7$-n | H | 1.05(t,3H),1.5~1.9(m,2H),3.20 (t,2H),7.5~7.7(m,1H),7.85~8.05 (m,2H),9.05(d,1H) |
| CH$_3$ | Cl | 2.61(s,3H),8.01(s,2H),9.0(s,1H) |
| Cl | CH$_3$ | 2.40(s,3H),7.58(t,2H),8.67(s,2H) |
| Cl | Cl | 7.35~7.75(m,2H),8.89(s,1H) |
| Cl | CF$_3$ | 7.1~7.3(m,1H),7.4~7.7(m,2H), 8.92(d,1H) |
| Br | H | ** |

TABLE 2

General formula (thiazole-imidazole with $R_2$, $R_1$, $R_0$, $SO_3H$)

| $R_0$ | $R_1$ | $R_2$ | NMR(DMSO-$d_6$)$\delta$ |
|---|---|---|---|
| CH$_3$ | H | H | 2.51(s,3H),7.53(d,1H),7.95(d,1H) |
| CH$_3$ | CH$_3$ | H | 2.54(s,3H),2.83(s,3H),7.21(s,1H) |
| C$_2$H$_5$ | H | H | 1.22(t,3H),3.99(q,2H),7.70(d,1H), 8.12(d,1H) |
| n-C$_3$H$_7$ | H | H | 0.91(t,3H),1.43~1.90(m,2H), 2.91(t,2H),7.58(d,1H),7.98(d,1H) |
| CH$_2$Cl | H | H | 5.08(s,2H),7.63(d,2H),8.02(d,1H) |
| CF$_3$ | H | H | 7.49(d,1H),8.04(d,1H) |

TABLE 2-continued

General formula

| $R_0$ | $R_1$ | $R_2$ | NMR(DMSO-$d_6$)$\delta$ |
|---|---|---|---|
| H | CH$_3$ | H | 2.13(s,3H),7.13(s,1H),7.60(s,1H) |
| Cl | H | H | 7.33(d,1H),7.96(d,1H) |
| Cl | CH$_3$ | H | 2.50(s,3H),7.83(s,1H) |
| Br | H | H | 7.38(d,1H),7.93(d,1H) |
| SCH$_3$ | H | H | 2.48(s,3H),7.48(d,1H),7.95(d,1H) |
| Cl | CH=CH-CH=CH (fused) | | 7.3~7.65(m,1H),7.9~8.1(m,2H), 8.75~8.92(m,1H) |

TABLE 3

General formula (pyridazine-imidazole with $R_1$, $R_0$, $SO_3H$)

| $R_0$ | $R_1$ | NMR(DMSO-$d_6$)$\delta$ |
|---|---|---|
| H | H | |
| CH$_3$ | H | ** |
| Cl | H | |
| CO$_2$C$_2$H$_5$ | H | |
| H | Cl | |
| CH$_3$ | Cl | ** |
| Cl | Cl | 7.46(d,1H),8.16(d,1H) |
| CO$_2$C$_2$H$_5$ | Cl | |
| CH$_3$ | CH$_3$ | |
| Cl | CH$_3$ | |

TABLE 4

General formula (triazine-imidazole with $R_1$, $R_2$, $R_0$, $SO_3H$)

| $R_0$ | $R_1$ | $R_2$ | NMR(DMSO-$d_6$)$\delta$ |
|---|---|---|---|
| H | H | H | ** |
| H | H | CH$_3$ | ** |
| H | CH$_3$ | CH$_3$ | ** |
| H | CH$_3$ | CF$_3$ | ** |
| CH$_3$ | H | H | 2.55(s,3H),7.0~7.2(m,1H), 8.62(d,d,1H),9,10(d,d,1H) |
| CH$_3$ | CH$_3$ | CH$_3$ | 2.7(s,3H),2.8(s,3H) 2.9(s,3H),7.1(s,1H) |
| Cl | CH$_3$ | CH$_3$ | 2.59(s,3H),2.67(s,3H), 7.07(s,1H) |
| SCH$_3$ | CH$_3$ | CH$_3$ | ** |
| SC$_2$H$_5$ | CH$_3$ | CH$_3$ | 1.36(t,3H),2.63(s,3H),2.73 (s,3H),3.16(q,2H), 7.00(s,1H) |
| SC$_3$H$_7$-n | CH$_3$ | CH$_3$ | ** |
| SC$_4$H$_9$-n | CH$_3$ | CH$_3$ | ** |
| S—CH$_2$—CH=CH$_2$ | CH$_3$ | CH$_3$ | ** |
| O—SO$_2$—C$_6$H$_4$—CH$_3$ | CH$_3$ | CH$_3$ | 2.45(s,3H),2.54(s,6H),6.92 (s,1H),7.41(d,2H), 7.94(d,2H) |

TABLE 5

General formula $R_1-\overset{N-N}{\underset{S}{\underset{|}{\|}}}\underset{SO_3H}{=}R_0$

| $R_0$ | $R_1$ | NMR(D$_2$O)δ |
|---|---|---|
| H | CH$_3$ | ** |
| CH$_3$ | CH$_3$ | 2.21(s,3H),2,48(s,3H),6.57(s,3H) |
| CONH$_2$ | CH$_3$ | ** |

TABLE 6

General formula (pyridine-imidazole with $R_0$ at 2-position and SO$_3$H)

| $R_0$ | NMR(DMSO-d$_6$)δ |
|---|---|
| H | 7.1~7.4(m,2H),7.98(d,d,1H), 8.50(d,d,1H),954(s,1H) |
| CH$_3$ | 2.81(s,3H),7.0~7.3(m,2H), 7.88(d,d,1H),8.33(d,d,1H) |
| SCH$_3$ | 2.69(s,3H),7.15~7.43(m,2H), 8.09(d,1H),8.49(d,1H) |

TABLE 7

General formula
R—SO$_3$H

| R | NMR(DMSO-d$_6$)δ |
|---|---|
| (dihydrothiazole-imidazole with Cl) | 3.7~4.1(m,1H),4.15~4.45(m,1H) |
| (imidazo[1,2-a]pyridine with CH$_3$) | 2.61(s,3H),7.45~7.60(m,1H),8.7~8.85(m,1H),9.1~9.2(m,1H) |
| (thiazole-imidazole with CH$_3$) | 2.58(s,3H),9,47(s,1H) |
| (N-CH$_3$ imidazo with CH$_3$) | 2.43(s,3H),4.78(s,3H),7.35~7.62(m,2H) |

REFERENCE EXAMPLE 36

2-Chloroimidazo[1,2-a]pyridine-3-sulfonylchloride

2-Chloroimidazo[1,2-a]pyridine-3-sulfonic acid (5.0 g) is suspended in 30 ml of phosphorus oxychloride and refluxed for 5 hours. After cooling, the reaction solution is poured into 250 ml of ice water and extracted with dichloromethane. The dichloromethane layer is collected, dried on anydrous sodium sulfate and then concentrated to dryness under reduced pressure to afford 4.6 g of the title compound as pale yellowish crystals.

NMR(CDCl$_3$)δ: 7.2-7.4(m,1H), 7.6-7.9(m,2H), 8.85(d,1H).

REFERENCE EXAMPLE 37

2-Chloroimidazo[1,2-a]pyridine-3-sulfonamide

A solution of 4.6 g of 2-chloroimidazo[1,2-a]pyridine-3-sulfonylchloride in 60 ml of acetonitrile is added to 60 ml of aqueous ammonia under cooling and stirred for 2 hours at room temperature. The reaction solution is distilled under reduced pressure to remove acetonitrile, and the precipitated crystals are collected by filtration and washed with water to give 3.8 g of the title compound. Upon recrystalization from diluted ethanol, it gives colorless needles mp. 175°-177° C.

NMR(DMSO-d$_6$)δ: 7.2-7 45(m 1H) 7.5-7.9(m 2H) 8.15(s,2H), 8.80(d,1H).

REFERENCE EXAMPLE 38

3,6-Dimethylimidazo[2,1-b]thiazole-5-sulfonamide

To a suspension of 2.8 g of 3,6-dimethylimidazo [2,1-b]thiazole-5-sulfonic acid in 3.4 ml of phophorus oxychloride, 1.8 g of tri-n-propylamine is added under cooling and stirred for 30 minutes at 60° C. The reaction solution after cooling is poured into ice water and extracted with dichloromethane. The dichloromethane layer is collected, dried and then distilled to remove dichloromethane. The residue is dissolved in 35 ml of acetonitrile, to which 3.8 ml of aqueous ammonia is added under cooling and stirred for 30 minutes at room temperature. The acetonitrile is distilled off under reduced pressure, and to the residue is added water. The precipitated crystalline solid is collected by filtration and washed with tetrachloromethane to give 1.5 g of the title compound as colorless crystals. mp. 177°-178° C.

NMR(DMSO-d$_6$)δ: 2.45(s,3H), 2.66(s,3H), 6.95(s,1H), 7.62(s,2H).

REFERENCE EXAMPLE 39

2-Methylsulfonylimidazo[1,2-a]pyridine-3-sulfonamide

To a solution of 1.7 g of 2-methylthioimidazo[1,2-a]pyridine-3-sulfonamide in 15 ml of dimethylformamide is added 3.3 g of m-chloroperbenzoic acid under ice cooling, followed by stirring for 4 hours at room temperature. To the reaction solution is added 20 ml of 10% sodium sulfite and 1.2 g of sodium hydrogen carbonate, followed by stirring for 2 hours at room temperature. The crystals are collected by filtration and washed with hot ethanol to give 1.4 g of the title compound as colorless crystals. mp. 214°-216° C.

NMR(DMSO-d$_6$)δ: 3.45(s,3H), 7.45(t,1H), 7.58-7.9 (m,2H), 7.92(s,2H), 8.96(d,1H);

REFERENCE EXAMPLE 40

6-Chloro-2,3-dihydro-imidazo[2,1-b]thiazole-5-sulfonamide-1-oxide

To a suspension of 2.0 g of 6-chloro-2,3-dihydroimidazo[2,1-b]thiazole-5-sulfonamide in 20 ml of acetic acid is add 2.2 g of 30% aqueous hydrogen peroxide, followed by stirring for 30 minutes at room temperature and further for 4 hours at 35°-45° C. Stirring is further maintained for 8 hours at room temperature, and the precipitated crystals are collected by filtration, washed with water and then dried to give 1.7 g of the title compound as colorless crystals. mp. 215°-217° C. (decomp.)

NMR(DMSO-d$_6$)δ: 3.7-4.2(m,2H), 4.5-4.9(m,2H), 8.1(s,2H).

REFERENCE EXAMPLE 41

6-Chloro-2,3-dihydro-imidazo[2,1-b]thiazole-5-sulfonamide-1,1-dioxide

To a suspension of 0.80 g of 6-chloro-2,3-dihydroimidazo[2,1-b]thiazole-5-sulfonamide-1-oxide in 10 ml of acetic acid is added 4 ml of 30% aqueous hydrogen peroxide solution followed by stirring for hour 100° C. After cooling, ice water is added to the reaction mixture to precipitate crystals. The crystals are collected by filtration, washed with water and dried to give 0.30 g of the title compound as colorless crystals. mp. 246°-247° C.

NMR(DMSO-$d_6$)$\delta$: 4.15–4.45(m,2H), 4.65–4.85(m,2H), 8.16(s,2H).

REFERENCE EXAMPLE 42

2-Ethoxycarbonylimidazo[1,2-a]pyridine-3-sulfonamide

Lithium diisopropylamide (2.2 g) is dissolved in 50 ml of anhydrous ether and cooled to −60° C. To this solution, 3.8 g of ethyl imidazo[1,2-a]pyridine-2-carboxylate is added and stirred for 2 hours at −60° C., followed by blowing sulfurous acid gas for 20 minutes. The mixture is stirred for an hour at −60° C., which is gradually raised to 0° C. The precipitated crystals are collected by filtration and dried to give 4.7 g of lithium salt of 2-ethoxycarbonylimidazo[1,2-a]pyridine-3-sulfinic acid. This product then is dissolved in 20 ml of water and 20 ml of dichloromethane, to which 2.4 g of N-chlorosuccinimide is added at −3°∼8° C. stirred for an hour at room temperature. The separated dichloromethane layer is dried on anhydrous sodium sulfate and distilled under reduced pressure to remove dichloromethane. The residue (crude 2-ethoxycarbonylimidazo-[1,2-a]pyridine-3-sulfonylchloride) is dissolved in 30 ml of acetonitrile and cooled to 0° C. After adding 20 ml of aqueous ammonia, the mixture is stirred for 30 minutes and evaporated to dryness under reduced pressure. The residue is purified by silica gel chromatography (eluent: ethyl acetate) to give 0.6 g of the title compound as colorless crystals. mp. 166°-168° C.

NMR(CDCl$_3$)$\delta$: 1.48(t,3H), 4.55(q,2H), 6.48(s,2H), 7.05(t,1H), 7.45(t,1H), 7.78(d,1H), 9,10(d,1H).

REFERENCE EXAMPLE 43

Imidazo[1,5-a]pyridine-3-sulfonamide (1) To a solution of 2.0 g of imidazo[1,5-a]pyridine in 60 ml of tetrahydrofuran is added 6.4 ml of n-butyl lithium (1.6N-hexane solution) at −78° C. during 20 minutes under nitrogen gas atmosphere. After stirring for an hour at the same temperature, sulfur dioxide gas is blowed into the mixture at −78°∼−55° C. for 30 minutes. After further stirring for 30 minutes, the temperature of the mixture is gradually raised and then the mixture is concentrated (below room temperature) under reduced pressure. The resulting yellowish crystals are washed with ether and dried. Then the crystals are added to a mixture of 3.6 g of N-chlorosuccinimide in 60 ml of dichloromethane and 60 ml of water at 3°-8° C. and stirred for 1.5 hours at the same temperature. The organic layer is separated and the aqueous layer is extracted with dichloromethane. The combined organic layers are dried an anhydrous magnesium sulfate and distilled to remove dichloromethane, and the residue is dissolved in 40 ml of acetonitrile. t-Butylamine (20 ml) is added to the solution under ice cooling, and stirred for an hour at the same temperature and for 2 hours at room temperature. After concentrating under reduced pressure, the residue is dissolved in dichloromethane, washed with 10% sodium carbonate solution and then with water and dried on anhydrous magnesium sulfate. Dichloromethane is distilled off and the residue is subjected to silica gel chromatography (eluent: chloroform-acetone) to give 1.2 g N-(t-butyl)imidazo[1,5-a]pyridine-3-sulfonamide and 0.46 g of N-(t-butyl)imidazo[1,5-a]pyridine-5-sulfonamide. 3-sulfonamide compound: mp. 180°-181° C.

NMR(CDCl$_3$)$\delta$: 1.20(s,9H), 5.84(s,1H), 6.76-7.10 (m,2H), 7.57-7.64(m,2H), 8.82(d,1H). 5-sulfonamide compound: mp. 203°-204° C.

NMR(CDCl$_3$)$\delta$: 1.19(s,9H), 7.25(s,1H), 6.86(d,d,1H), 7.47(d,1H), 7.71-7.73(m,2H), 8.80(s,1H).

(2) N-(t-Butyl)imidazo[1,5-a]pyridine-3-sulfonamide (1.0 g) is dissolved in 20 ml of trifluoroacetic acid and stirred for 14 days at room temperature. The mixture is concentrated under reduced pressure, and ether is added to the residue to precipitate crystals. The crystals are collected by filtration and dried to give 0.60 g of the title compound. mp. 179°-180° C.

NMR(CDCl$_3$)$\delta$: 1.43(t,3H), 2.50(s,3H), 4.50(q,2H), 6.12(s,2H), 6.83(s,1H).

REFERENCE EXAMPLE 44

Imidazo[1,5-a]pyridine-5-sulfonamide

The title compound is prepared from N-(t-butyl) imidazo[1,5-a]pyridine-5-sulfornamide by a similar way to Reference Example 43. mp. 148°-151° C.

NMR(DMSO-$d_6$)$\delta$: 7.16(d,d,1H), 7.48(d,d,1H), 7.89(s,1H), 7.97(d,1H), 8.26 (s,2H), 8.93(s,1H).

REFERENCE EXAMPLE 45

5-Ethoxycarbonylimidazo[2,1-b]thiazole-6-sulfonamide

Ethyl 6-(p-methoxybenzylthio)imidazo[2,1-b]thiazole-5-carboxylate (7.0 g) is dissolved in 60 ml of dichloromethane, to which 40 ml of water and 6 ml of concentrated hydrochloric acid are added and cooled. 5% Aqueous hypochlorous acid (98 ml) is gradually and dropwise added to the mixture at −15°∼−10° C. and stirred for 30 minutes at room temperature. The dichloromethane layer is separated and dried on anhydrous magnesium sulfate. Dichloromethane is distilled off, and the residue is dissolved in 30 ml of acetonitrile, to which 50 ml of aqueous ammonia is added and stirred for an hour. The reaction solution is concentrated under reduced pressure, and the residue after adding water is neutralized with hydrochloric acid (to pH 5) and extracted with ethyl acetate. The ethyl acetate layer is dried on anhydrous magnesium sulfate and distilled water reduced pressure to remove ethyl acetate. The residue is recrystallized from acetonitrile to give 0.91 g of the title compound. mp. 164°-166° C.

NMR(DMSO-$d_6$)$\delta$: 1.45(t,3H), 4.49(q,2H), 7.06 (s,2H), 7.48(d,1H), 8.10(d,1H).

REFERENCE EXAMPLE 46

6-Ethoxycarbonyl-3-methylpyrazolo[5,1-b]thiazole-7-sulfonamide

Bis-(6-ethoxycarbonyl-3-methylpyrazolo[5,1-b]thiazol-7-yl)disulfide (3.0 g) is suspended in 50 ml of 30% acetic acid, followed by blowing chlorine gas for an hour at −10°∼−8° C. After stirring for an hour at −10°∼5° C., the precipitated crystals are dissolved in 20 ml of dichloromethane, to which 50 ml of aqueous ammonia and 100 ml of ethanol are added under ice cooling and stirred for an hour below 10° C. The solution is concentrated under reduced pressure, and the residue is purified by silica gel chromatography (eluent: chloroform-ethanol) to yield 1.5 g of the title compound.

NMR(CDCl$_3$)δ: 1.43(t,3H), 2.50(s,3H), 4.50 (q,2H), 6.12(s,2H), 6.83(s,1H).

REFERENCE EXAMPLE 47

6-Carbamoyl-3-methylpyrazolo[5,1-b]thiazole-7-sulfonamide

Bis-(6-methoxycarbonyl-3-methylpyrazolo[5,1-b]thiazol-7-yl)disulfide (3.2 g) is suspended in 50 ml of 30% acetic acid, to which chlorine gas is blowed at −10°–0° C. The collected precipitate is dissolved in 20 ml of dichloromethane, to which 30 ml of aqueous ammonia and the 70 ml of ethanol are added and stirred for an hour at room temperature. The mixture is allowed to stand overnight, and the precipitate is collected by filtration, washed with water and dried to obtain 2.0 g of the title compound. mp. over 270° C.

NMR(DMSO-d$_6$) δ: 2.44(s,3H), 6.88(s,1H), 7.13 (s,2H), 7.73(s,2H).

REFERENCE EXAMPLE 48

2-Ethylthiomethylimidazo[1,2-a]pyridine-3-sulfonamide (1) 2-Chloromethylimidazo[1,2-a]pyridine-3-sulfonic acid (5.9 g) is suspended in 50 ml of chloroform, to which 5.1 g of tri-n-propylamine is added and stirred for 30 minutes at room temperature. Chloroform is distilled off and to the residue is added 40 ml of phosphorus oxychloride, followed by stirring for an hour at 60° C. After cooling, the mixture is poured into ice water and extracted with dichloromethane. Dichloromethane is distilled off, and the residue is dissolved in 30 ml of acetonitrile to which 3.1 g of t-butylamine is added and stirred for an hour. The reaction solution is concentrated under reduced pressure, and water is added to the residue to precipitate crystals. The crystals are collected by filtration and dried to yield 5,8 g of N-(t-butyl)-2-chloromethylimidazo[1,2-a]pyridine-3-sulfonamide. mp. 180°–182° C.

(2) N-(t-Butyl)-2-chloromethylimidazo[1,2-a]pyridine-3-sulfonamide (3.2 g) is added to a suspension of 0.40 g of 60% oily sodium hydride in 30 ml of tetrahydrofuran and stirred for 30 minutes at room temperature. The precipitate is collected by filtration and suspended in 30 ml of ethanol. Sodium thioethoxide (prepared from ethanethiol and sodium ethoxide) (1.0 g) is added to the suspension and stirred for 30 minutes at room temperature and further for 2 hours under refluxing. After removing ethanol under reduced pressure, to the residue is added water, which is then neutralized by hydrochloric acid. The solution is extracted with dichloromethane and the dichloromethane layer is subjected to silica gel chromatography (eluent: ethyl acetate) to give 2.9 g of N-(t-butyl)-2-ethylthiomethylimidazo[1,2-a]pyridine-3-sulfonamide as colorless needles. The product is dissolved in 35 ml of trifluoroacetic acid and stirred for 27 hours at room temperature. After trifluoroacetic acid is distilled off under reduced pressure, the resulting residue is purified by silica gel chromatography (eluent: ethyl acetate) to give 1.2 g of crystals (dihydrate) of the title compound.

NMR(DMSO-D$_6$) δ: 1.20(t,3H), 2.62(q,2H), 4.09 (s,2H), 5.05(s,4H), 7.17(t,1H), 7.35–7.67(m,2H), 7.75(s,2H), 8.75 (d,1H).

REFERENCE EXAMPLE 49

3-Chloroimidazo[1,5-a]pyridine-1-sulfonamide (1) 3-Chloroimidazo[1,5-a]pyridine-1-sulfonic acid (2.3 g) is suspended in 20 ml of dichloromethane, to which 2.3 ml of tri-n-propylamine is added and stirred for an hour at room temperature. The mixture is distilled to remove dichloromethane, and 10 ml of phosphorus oxychloride is added to the residue and stirred for 3 hours at 50°–55° C. and for 2 hours at 75° C. The reaction solution is poured into ice water and extracted with dichloromethane. The extract is purified by silica gel chromatography (eluent: dichloromethane) to give 1.4 g of crystals of imidazo[1,5-a]pyridine-1-sulfonylchloride. This crystals are dissolved in 10 ml of acetonitrile, to which 5 ml of t-butylamine is added under ice cooling and stirred for 15 hours at room temperature. Acetonitrile is distilled off under reduced pressure and to the resulting residue is added water. The precipitate is collected by filtration, washed with water and dried to obtain 1.3 g of crystals of N-(t-butyl) imidazo[1,5-a]pyridine-1-sulfonamide.

NMR(DMSO-d$_6$) δ: 1.20(s,9H), 5.20(s,1H), 6.76 (t,1H), 7.05(d,d,1H), 7.97–8.11 (m,2H), 8.22(s,1H).

(2) To a solution of 1.2 g of N-(t-butyl)imidazo [1,5-a]pyridine-1-sulfonamide in 30 ml of chloroform is added 1.0 g of N-chlorosuccinimide under ice cooling, followed by stirring for 30 minutes at 5°–10° C. and then for 17 hours at room temperature. Fruther, 0.40 g of N-chlorosuccinimide is added to the mixture and stirred for 6 hours at room temperature, followed by addition of 50 ml of water. The chloroform layer is collected and the aqueous layer is extracted with chloroform. The combined chloroform layers are dried on anhydrous magnesium sulfate and concentrated under reduced pressure. The residue is purified by silica gel chromatography (eluent: chloroform-ethyl acetate) to yield 0.30 g of crystals of N-(t-butyl)-3-chloroimidazo[1,5-a]pyridine-1-sulfonamide. The crystals are dissolved in 30 ml of trifluoroacetic acid and stirred for 2 hours at room temperature. After concentrating under reduced pressure, the precipitated crystals are collected by filtration and washed with chloroform to give 0.25 g of crystals of the title compound.

NMR(DMSO-d$_6$) δ: 6.96–7.35(m,2H), 7.43(s,2H), 7.92(d,d,1H), 8.28(d,1H).

REFERENCE EXAMPLE 50

2-Fluoroimidazo[1,2-a]pyridine-3-sulfonamide (1) To a solution of 20.0 g of 2-chloroimidazo[1,2-a]pyridine-3-sulfonylchloride in 100 ml of sulfolane are added 2.0 g of potassium fluoride and 1.0 g of 18-crown-6-ether, and stirred for 14 hours at 150° C. After cooling, the reaction solution is poured into ice water and the precipitate collected by filtration is dissolved in dichloromethane. The solution is decolored with charcoal, dried on anhydrous magnesium sulfate and then distilled to remove dichloromethane, by which 14.0 g of 2-fluoroimidazo[1,2-a]pyridine-3-sulfonylfluoride is obtained mp. 108°–110° C.

NMR(CDCl$_3$) δ: 8.69(d,1H), 7.2–7.9(m,3H).

(2) To a solution of 2.0 g of 2-fluoroimidazo[1,2-a]pyridine-3-sulfonylfluoride in 30 ml of methanol is added to 0.50 g of sodium methylate, followed by stirring for an hour at room temperature. The mixture is distilled under reduced pressure to remove methanol and the residue is extracted with chloroform. After chloroform is distilled off, the resulting residue is dissolved in 20 ml of dichloromethane, to which 2 ml of aqueous ammonia is added and stirred for 30 minutes at room temperature. The precipitate is collected by filtration and dried, to which 10 ml of phosphorus oxychloride is added and refluxed for 4 hours. After cooling, the mixture is poured into ice water and the precipitate collected by filtration is dissolved in 10 ml of acetonitrile. To this solution is added 5 ml of aqueous ammonia under cooling, followed by stirring for 30 minutes at room temperature. The mixture is distilled under reduced pressure to remove acetonitrile, and the precipitated crystals are collected by filtration, washed with water and dired to obtain 0.31 g of the title compound.

NMR(DMSO-$d_6$) $\delta$: 7.25(t,1H), 7.53–7.76(m,2H), 7.90(s,2H), 8.72(d,1H).

REFERENCE EXAMPLE 51

6-Methoxy-2-methylimidazo[1,2-b]pyridazine-3-sulfonamide

To a solution of 4.9 g of 6-chloro-2-methylimidazo[1,2-b]pyridazine-3-sulfonamide in 50 ml of methanol is added 2.2 g of sodium methylate, followed by refluxing for 4 hours. Methanol is distilled off and the residue after addition of water is neutralized with hydrochloric acid. The precipitated crystals are collected by filtration and dried to give 4.8 g of the title compound. mp. 251° C.

NMR(DMSO-d6)$\delta$: 2.52(s,3H), 4.03(s,3H), 7.00 (d,1H), 7.40(s,2H), 7.98(d,1H).

REFERENCE EXAMPLE 52

6-Dimethylamino-2-methylimidazo[1,2-b]pyridazine-3-sulfonamide

To a solution of 4.9 g of 6-chloro-2-methylimidazo[1,2-b]pyridazine in 50 ml of acetonitrile is added 20 ml of 50% aqueous dimethylamine solution, followed by refluxing for 5 hours. The mixture is treated in a similar way to Reference Example 51 to give 3.6 g of the title compound. mp. 227° C.

MR(DMSO-$d_6$) $\delta$: 2.50(s,3H), 3.10(s,6H), 7.13 (d,1H), 7.20(s,2H), 7.79(d,1H).

The sulfonamides which may be prepared by a similar method to Reference Examples 36–52 are shown in Tables 8-16. (In the table, the compound marked with *** is subjected to the subsequent reaction without isolation thereof and its structure is confirmed as object compound thereof.

TABLE 8

General formula

| $R_0$ | $R_1$ | NMR (DMSO-$d_6$, $\delta$) or | mp. (°C.) |
|---|---|---|---|
| H | H | | 212–214 |
| $CH_3$ | H | | 103 |
| $CH_2Cl$ | H | | over 270 |
| $CH_2F$ | H | 5.72(d,2H),7.20(t,1H),7.40– 7.84(m,2H),7.90(s,2H),8.79 (d,1H) | |
| $CH_2OCH_3$ | H | 3.41(s,3H),4.82(s,2H),7.27 (t,1H),7.49–7.89(m,2H),8.76 (d,1H) | |

TABLE 8-continued

General formula

| $R_0$ | $R_1$ | NMR (DMSO-$d_6$, $\delta$) or | mp. (°C.) |
|---|---|---|---|
| $CH_2SC_2H_5$ | H | 1.22(t,3H),2.65(q,2H),4.08 (s,2H),7.15(t,1H),7.35–7.65 (m,2H),7.75(s,2H),8.75(d,1H) | |
| $CF_3$ | H | | 187–188 |
| Ph | H | | 183–184 |
| Br | H | 7.27(t,1H),7.43–7.80(m,2H), 8.01(s,2H),8.80(d,1H) | |
| $SCH_3$ | H | | 185–187 |
| $SC_2H_5$ | H | | 169–171 |
| $SC_3H_7$-n | H | | 153–155 |
| CN | H | | 233–235 |
| $CH_3$ | Cl | | 208–210 |
| Cl | $CH_3$ | | 197–200 |
| Cl | Cl | | 220–221 |
| Cl | $CF_3$ | | 200–202 |

TABLE 9

General formula

| $R_0$ | $R_1$ | $R_2$ | NMR (DMSO-$d_6$, $\delta$) or | mp. (°C.) |
|---|---|---|---|---|
| $CH_3$ | H | H | | 192–193 |
| $C_2H_5$ | H | H | | 188–189 |
| $C_3H_7$-n | H | H | | 154–155 |
| $CH_2Cl$ | H | H | | 250–260 |
| $CF_3$ | H | H | | 230–232 |
| H | $CH_3$ | H | | 177–178 (½ hydrate) |
| F | H | H | 7.53(d,1H),7.85–8.23 (m,3H) | |
| Cl | H | H | | 187–189 |
| Br | H | H | 7.57(d,1H),7.94(d,1H) | |
| $SCH_3$ | H | H | | 172–174 |
| $SOCH_3$ | H | H | | 243–244 |
| $SO_2CH_3$ | H | H | | 248–249 |
| Cl | CH=CH–CH=CH | | 7.4–7.75(m,2H),8.05– 8.25(m,1H),8.30(s,2H), 8.4–8.6(m,1H) | |
| $CH_3$ | $CH_3$ | H | | 177–178 |
| Cl | $CH_3$ | H | | 239–241 (decomp.) |

TABLE 10

General formula

| $R_0$ | $R_1$ | NMR(DMSO-$d_6$, $\delta$) or | mp. (°C.) |
|---|---|---|---|
| $CH_3$ | H | | 201–203 |
| $CH_3$ | Cl | | 227 |
| $CH_3$ | $CH_3S$ | | 224 |
| $CH_3$ | $CH_3SO$ | *** | |
| $CH_3$ | $CH_3SO_2$ | | |
| $CH_3$ | $C_2H_5O$ | | |
| Cl | n-$C_3H_7O$ | 1.05(t,3H),1.60–2.20(m,2H) 4.41(t,2H),7.19(d,1H), 7.72(s,2H),8.13(d,1H) | |

TABLE 10-continued

General formula:

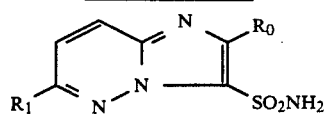

| R₀ | R₁ | NMR(DMSO-d₆, δ) or mp. (°C.) |
|---|---|---|
| Cl | i-C₃H₇O | |
| Cl | CH₂=CHCH₂O | |
| CH₃ | morpholino (O\_\_N—) | |
| H | H | |
| H | Cl | |
| H | CH₃O | |
| Cl | CH₃ | |
| Cl | H | |
| Cl | Cl | 7.70(d,1H), 7.99(s,2H), 8.35(d,1H) |
| Cl | (CH₃)₂N | 3.13(s,6H), 7.23(d,1H), 7.45(s,2H), 7.86(d,1H) |
| Cl | morpholino (O\_\_N—) | |

TABLE 10-continued

General formula:

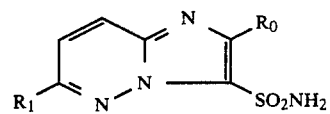

| R₀ | R₁ | NMR(DMSO-d₆, δ) or mp. (°C.) |
|---|---|---|
| Cl | CH₃O | 4.05(s,3H), 7.16(d,1H), 7.75(s,2H), 8.11(d,1H) |
| Cl | C₂H₅O | 1.41(t,3H), 4.52(q,2H), 7.11(d,1H), 7.65(s,2H), 8.08(d,1H) |
| Cl | CH₃S | 2.68(s,3H), 7.47(d,1H), 7.70(s,2H), 8.07(d,1H) |
| Cl | C₂H₅S | 1.53(t,3H), 3.25(q,2H), 7.30(t,1H), 7.46(s,2H), 8.00(d,1H) |
| Cl | n-C₃H₇S | 1.06(t,3H), 1.49~2.07(m,2H), 3.33(t,2H), 7.40(d,1H), 7.71(s,2H), 8.05(d,1H) |
| Cl | i-C₃H₄S | |
| Cl | CH₂=CHCH₂S | |
| Cl | CH₃SO₂ | 3.63(s,3H), 8.04(d,1H), 8.10(s,2H), 8.60(d,1H) |
| CO₂C₂H₅ | H | |
| CO₂C₂H₅ | Cl | 1.29(t,3H), 4.34(s,2H), 7.67(d,1H), 7.94(s,2H), 8.40(d,1H) |
| CO₂C₂H₅ | (CH₃)₂N | |
| CO₂C₂H₅ | CH₃O | |
| CO₂C₂H₅ | CH₃S | |
| CO₂C₂H₅ | CH₃SO₂ | |

TABLE 11

General formula:

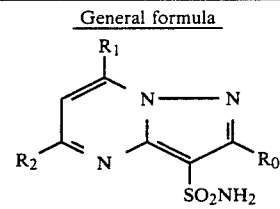

| R₀ | R₁ | R₂ | NMR(DMSO-d₆, δ) or mp. (°C.) |
|---|---|---|---|
| H | H | H | 181~182 |
| H | H | CH₃ | 152~154 |
| H | CH₃ | CH₃ | 214~217 |
| H | CH₃ | CF₃ | 2.72(s,3H),7.45(s,1H), 8.33(s,1H) |
| CH₃ | H | H | 215~220 |
| CH₃ | CH₃ | CH₃ | 2.57(s,6H),2.68(s,3H), 7.0(s,1H),7.06(s,2H) |
| Cl | CH₃ | CH₃ | 242~243 |
| SCH₃ | CH₃ | CH₃ | 2.55(s,3H),2.67(s,3H), 2.85(s,3H),6.90(s,2H), 6.98(s,1H) |
| SC₂H₅ | CH₃ | CH₃ | 209~210 |
| SC₃H₇-n | CH₃ | CH₃ | 1.03(t,3H),1.66~2.03 (m,2H),2.60(s,3H),2.70 (s,3H),3.20(t,2H),6.96 (s,2H),7.03(s,1H) |
| SC₄H₉-n | CH₃ | CH₃ | *** |
| —S—CH₂—CH=CH₂ | CH₃ | CH₃ | 2.59(s,3H),2.70(s,3H), 3.87(d,2H),5.10~5.50 (m,2H),5.85~6.30(m,1H), 6.97(s,1H),7.10(s,2H) |
| SO₂CH₃ | CH₃ | CH₃ | 2.67(s,3H),2.80(s,3H), 3.48(s,3H),7.20(s,2H), 7.29(s,1H) |
| SO₂C₂H₅ | CH₃ | CH₃ | 258~260 |
| SO₂C₃H₇-n | CH₃ | CH₃ | 1.08(t,3H),1.67~2.06 (m,2H),2.71(s,3H),2.83 (s,3H),3.60(t,2H),6.99 (s,2H),7.15(s,1H) |
| SO₂C₄H₉-n | CH₃ | CH₃ | |
| SO₂—CH₂—CH=CH₂ | CH₃ | CH₃ | |

TABLE 11-continued

General formula

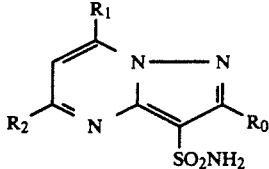

| $R_0$ | $R_1$ | $R_2$ | NMR(DMSO-$d_6$, δ) or mp. (°C.) |
|---|---|---|---|
|  | CH$_3$ | CH$_3$ | 210~212 |

TABLE 12

General formula

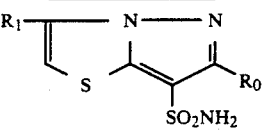

| $R_0$ | $R_1$ | NMR(DMSO-$d_6$, δ) or mp. (°C.) |
|---|---|---|
| H | CH$_3$ | 2.50(s,3H),7.10~7.20(m,1H), 7.36(s,2H),8.06(s,1H) |
| CH$_3$ | CH$_3$ | 200~201 |

TABLE 13

General formula

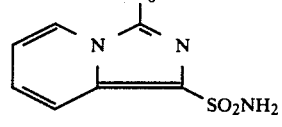

| $R_0$ | mp. (°C.) |
|---|---|
| H | 209~212 |
| CH$_3$ | 232 (decomp.) |
| Cl | 229~231 |
| SCH$_3$ | 198~200 |
| SO$_2$CH$_3$ | 244~247 |

TABLE 14

General formula

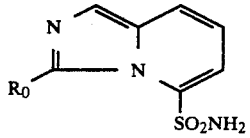

| $R_0$ | mp. (°C.) |
|---|---|
| CH$_3$ | 168~170 |
| SCH$_3$ | 200~202 |
| SO$_2$CH$_3$ | |

TABLE 15

General formula

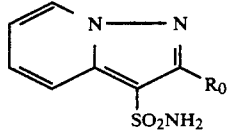

| $R_0$ | mp. (°C.) |
|---|---|
| CH$_3$ | 183~184 |
| Cl | |
| CO$_2$C$_2$H$_5$ | |

TABLE 16

General formula
$R_0$—SO$_2$NH$_2$

| $R_0$ | NMR(DMSO-$d_6$, δ) or mp. (°C.) |
|---|---|
| 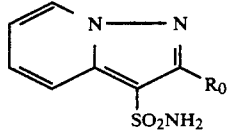 | 262~266 |
| 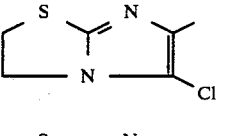 | 3.8~4.1(m,2H), 4.25~4.5(m,2H), 7.77(m,2H) |
| 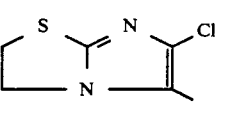 | 200~204 |
| 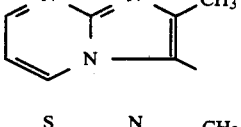 | 2.50(s,3H),7.66(s,2H), 9.33(s,1H) |
| 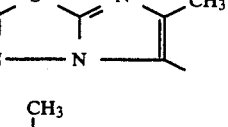 | 207 (decomp.) |
| 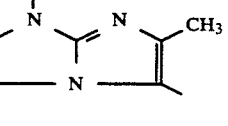 | 242~244 |

REFERENCE EXAMPLES 53

Phenyl N-(4,6-dimethoxypyrimidin-2-yl)carbamate

To a solution of 8.0 g of 2-amino-4,6-dimethoxypyrimidine in 50 ml of tetrahydrofuran are added 4.0 g of phenyl chlorocarbonate and 0.1 g of 4-dimethylaminopyridine, followed by stirring for 17 hours at room temperature. The mixture is allowed to stand overnight and filtered to remove insoluble product and the filtrate is purified by silica gel chromatography (eluent: dichloromethane) to give 4.4 g of the title compound. mp. 118°–119° C.

REFERENCE EXAMPLE 54

Phenyl N-(4-methoxy-6-methylpyridin-2-yl)carbamate

The title compound as colorless crystals is obtained from 2-amino-4-methoxy-6-methylpyrimidine and phenyl chlorocarbonate by a similar method to Reference Example 53. mp. 90°–92° C.

REFERENCE EXAMPLE 55

Phenyl N-(4,6-dimethylpyrimidin-2-yl)carbamate

The title compound as colorless crystals is obtained from 2-amino-4,6-dimethylpyrimidine by a similar method to Reference Example 53. mp. 124°–128° C.

REFERENCE EXAMPLE 56

Phenyl N-(4-chloro-6-emthoxypyrimidin-2-yl)carbamate

The title compound as colorless crystals is obtained from 2-amino-4-chloro-6-methoxypyrimidine by a similar method to Reference Example 53. mp. 98°–100° C.

REFERENCE EXAMPLES 57

Phenyl N-(4-methoxy-6-methyl-1,3,5-triazin-2-yl)carbamate (1) 2-Amino-4-methoxy-6-methyl -1,3,5-triazine (28.0 g) (see Journal of Organic Chemistry 28, 1816(1963), mp. 258° C.) is suspended in 100 ml of acetonitrile, to which 58.6 g of bis-(trimethylsilyl)acetamide is added and refluxed for 10 hours. After cooling, insoluble product is filtered off and the filtrate is concentrated. The residue is distilled under reduced pressure to give 29.0 g of 2-(trimethylsilyl) amino-4-methoxy-6-methyl-1,3,5-triazine. bp. 110°–111° C./3 mmHg.

(2) 2-(Trimethylsilyl)amino-4-methoxy-6-methyl-1,3,5-triazine (8.4 g) is dissolved in 50 ml of toluene, to which 9.4 g of phenyl chlorocarbonate is added and stirred for an hour at 80° C. After cooling, insoluble product is filtered off and the filtrate is concentrated under reduced pressure. The residue is purified by silica gel chromatography (eluent: toluene-ethyl acetate) to give 4.7 g of the title compound. mp. 105°–106° C.

REFERENCE EXAMPLE 58

4,6-Dimethoxy-2-isothiocyanatopyridine

To 300 ml of acetonitrile are added 45.0 g of 4,6-dimethoxy-2trimethylsilylaminopyridine and 35.0 g of phenylchlorothiocarbonate, followed by refluxing for 10 hours. The reaction solution is concentrated under reduced pressure to remove acetonitrile, and to the residue is added 300 ml of toluene. Insoluble product is filtered off, and the filtrate is concentrated under reduced pressure. The residue is purified by silica gel chromatography (eluent: ethyl acetate-hexane) to give 17.0 g of the title Compound. mp. 85°–86° C.
IR (liquid film)cm$^{-1}$: 1995

REFERENCE EXAMPLE 59

Phenyl N-(2-chloroimidazo[1,2-a]pyridin-3-ylsulfonyl)carbamate

2-Chloroimidazo[1,2-a]pyridine-3-sulfonamide (5.0 g) is dissolved in 200 ml of dioxane, to which 0.90 g of 60% oily sodium hydride is added at 10°–25° C. with stirring under nitrogen gas atmosphere. After stirring for an hour at 20°–30° C., to the mixture is added 4.9 of phenyl carbonate at 20°–30° C., followed by stirring for 2 hours. The reaction solution is poured into ice water and neutralized with hydrochloric acid (pH 4–7). The precipitated crystals are collected by filtration and dried to give 6.2 g of the title compound, which then is recrystallized from chloroform to yield colorless crystals. mp. 111°–113° C.
NMR(CDCl$_3$) δ: 6.68–7.80(m,8H), 9.02(d,1H), 12.30(s,1H).

REFERENCE EXAMPLE 60

Methyl N-(2-chloroimidazo[1,2-a]pyridin-3-ylsulfonyl)carbamate

Methyl carbamate (1.6 g) is dissolved in 50 ml of tetrahydrofuran, to which 2.1 g of 60% oily sodium hydride is added at 18°–20° C. under nitrogen gas atmosphere. After stirring for an hour at room temperature, a solution of 5.0 g of 2-chloroimidazo[1,2-a]pyridine-3-sulfonylchloride in 20 ml of tetrahydrofuran is added to the reaction mixture at 20°–30° C. within 30 minutes. The mixture is stirred for 24 hours at room temperature, and the precipitate collected by filtration is dissolved in ice water and adjusted to pH 4–5 by addition of hydrochloric acid. The precipitated crystals are collected by filtration and dried to give 2.8 g of the title compound.
NMR(DMSO-d$_6$) δ: 3.60(s,3H), 7.26–7.83(m,3H), 8.89(m,1H), 10.5(s,1H).

REFERENCE EXAMPLE 61

Ethyl N-(2-chloroimidazo[1,2-a]pyridin-3-ylsulfonyl)carbamate

The title compound is obtained by a similar method to Reference Example 60.
NMR(DMSO-d$_6$) δ: 1.09(t,3H), 4.05(q,2H), 7.20–7.83 (m,3H), 8.90(d,1H), 10.5(s,1H).

EXAMPLE 1

N-(2-Chloroimidazo[1,2-a]pyridin-3-ylsulfonyl)-N'-(4,6-dimethoxy-2-pyrimidinyl)urea (Compound No. 1)

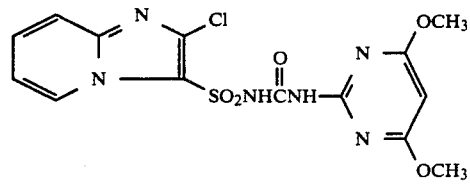

To a suspension of 0.50 g of 2-chloroimidazo[1,2-a]pyridine-3-sulfonamide in 10 ml of acetonitrile are added 0.60 g of phenyl N-(4,6-dimethoxypyridin-2-yl)carbamate and then 0.34 g of DBU, followed by stirring for 2 hours at room temperature. After 50 ml of ice water is added to the reaction solution, it is neutralized (to pH 4) with hydrochloric acid and the precipitated crystals are filtered. The crystals are washed with water and then ethanol, and dried to give 0.65 g of the title compound as colorless crystals. mp. 180°–183 °C. (dec.).

NMR(DMSO-d$_6$) δ: 3.95(s,6H), 6.0(s,1H), 7.3–7.5 (m,1H), 7.5–7.9(m,2H), 8.97(d,1H), 10.65(s,1H), 12.8(s,1H).

EXAMPLE 2

N-(2-Chloroimidazo[1,2-a]pyridin-3-ylsulfonyl)-N'-(4-methoxy-6-methyl-2-pyrimidinyl)urea (Compound No. 2)

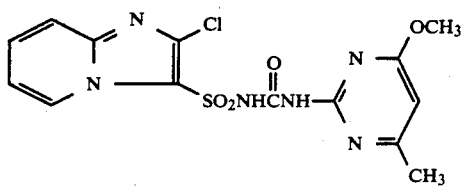

To a suspension of 0.50 g of 2-chloroimidazo[1,2-a]pyridine-3-sulfonamide in 10 ml of acetonitrile are added 0.57 g of phenyl N-(4-methoxy-6-methylpyrimidin-2-yl)carbamate and then 0.34 g of DBU, followed by stirring for 1.5 hours at room temperature. The reaction solution is poured into 50 ml of ice water, adjusted to pH 4 by addition of hydrochloric acid and extracted with ethyl acetate. The ethyl acetate layer separated is dried on anhydrous sodium sulfate and concentrated under reduced pressure to remove ethyl acetate. The residue is washed with ether and dried to give 0.64 g of the title compound as colorless needle crystals. mp. 164°–168° C.

NMR(DMSO-d$_6$) δ: 2.50(s,3H), 4.05(s,3H), 6.65(s,1H), 7.3–7.5(m,1H), 7.6–7.9(m,2H), 9.10 (d,1H), 10.85(s,1H), 13.0–14.0 (br. s,1H).

EXAMPLE 3

N-(6-Methylimidazo[2,1-b]thiazol-5-ylsulfonyl)-N'-(4,6-dimethoxy-2-pyrimidinyl)urea (Compound No. 3).

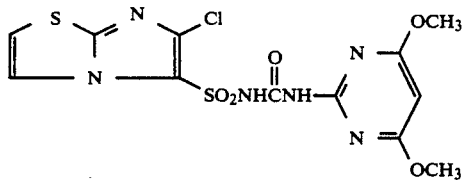

6-Methylimidazo(2,1-b]thiazole-5-sulfonamide (0.44 g) and phenyl N-(4,6-dimethoxypyridimin-2-yl)carbamate (0.60 g) are dissolved in 20 ml of acetonitrile, to which 0.35 g of DBU is added and stirred for 2 hours at room temperature. After addition of 50 ml of ice water, the mixture is adjusted to pH 3–4 by addition of hydrochloric acid. The precipitated crystals are filtered washed with water and then ethanol, and dried to give 0.76 g of the title compound as colorless crystals. mp. 181°–183° C.

NMR(DMSO-d$_6$) δ: 2.50(s,3H), 3.93 (s,6H), 5.97 (s,1H) 7.47 (d,1H), 7.94 (d,1H), 10.54 (s,1H), 12.75 (s,1H).

EXAMPLE 4

N-(2-Chloroimidazo[1,2-a]pyridin-3-ylsulfonyl)-N'-(4,6-dimethoxy-2-pyrimdinyl)thiourea (Compound No. 4)

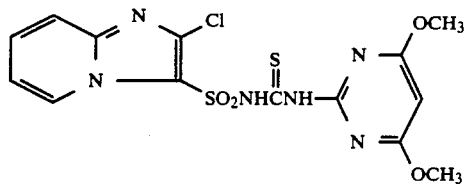

2-Chloroimidazo[1,2-a]pyridine-3-sulfonamide (2.3 g) and 4,6-di thoxypyridin-2-ylisothiocyanate (2.0 g) are dissolved in 100 ml of acetone, to which 1.4 g of potassium carbonate is added and stirred for 3 hours at room temperature. The precipitate is collected by filtration and suspended in 200 ml of ice water. The mixture is acidified (pH 2) by addition of hydrochloric acid, and the resulting crystals are collected by filtration, washed with water and dried to give 3.0 g of monohydrate of the title compound. mp. 190°–192° C.

Elemental Analysis for C$_{14}$H$_{13}$N$_6$O$_4$S$_2$Cl.H$_2$O: Calculated (%) C,37.63; H,3.33; N,18.81 Found (%) C,37.96; H,3.01; N,18.86

EXAMPLE 5

N-(2-Methylpyrrolo[1,2-a]pyridin-1-ylsulfonyl)-N'-(4,6-dimethoxy-2-pyrimidinyl)urea (Compound No. 5)

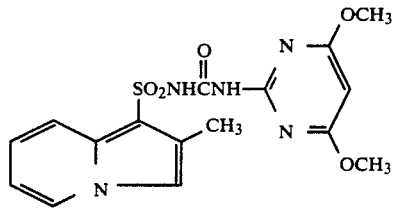

and N-(2-methylpyrrolo[1,2-a]pyridin-3-ylsulfonyl-N'-(4,6-dimethoxy-2-pyrimidinyl)urea (Compound No. 6)

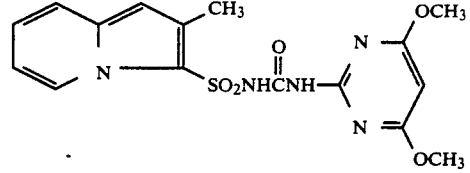

A solution of 4.8 g of chlorosulfonyl isocyanate in 10 ml of tetrahydrofuran (THF) is added to a solution of 4.7 g of 2-amino-4,6-dimethoxypyrimidine in 80 ml of THF under ice cooling and stirred for 30 minutes to yield N-chlorosulfonyl-N'-(4,6-dimethoxy-2-pyrimidinyl)urea. A solution of 1.0 g of 2-methylpyrrolo[1,2-a]pyridine in 10 ml of THF and 1.0 g of aluminum chloride are added to the above mixture and stirred for an hour at room temperature. THF is distilled off. The residue after addition of water is extracted with ethyl acetate. The extract is dried and distilled to remove ethyl acetate. The residue is purified by silica gel chromatography (eluent: n-hexane-ethyl acetate) to give 0.71 g of the title compound (Compound No. 5)

having mp. 197°-199° C. and 0.88 g of the title compound (Compound No. 6) having mp. 168°-169° C.

NMR(DMSO-$d_6$) δ: (Compound No. 5) 2.40(s,3H), 3.91(s,6H), 5.85(s,1H), 6.70-7.26(m,2H), 7.42(s,1H), 7.93 (d,1H), 8.35(d,1H), 10.22(s,1H), 12.43(s,1H).

(Compound No. 6) 2.50(s,3H), 3.92(s,6H), 5.93(s,1H), 6.50(s,1H), 6.70-7.26(m,2H), 7.40-7.70(m,1H), 8.80(m,1H), 10.46(s,1H), 12.68(s,1H).

EXAMPLE 6

N-(2-Chloroimidazo[1,2-a]pyridin-3-ylsulfonyl)-N'-(4,6-dimethoxy-2-pyrimidinyl)urea (Compound No. 1)

Phenyl N-(2-chloroimidazo[1,2-a]pyridin-3-ylsulfonyl) carbamate (2.0 g) and 2-amino-4,6-dimethoxypyrimidine (0.90 g) are dissolved in 50 ml of acetonitrile and refluxed for 20 minutes. After cooling, the precipitated crystals are collected by filtration and dired to obtain 1.6 g of the title compound. mp. 183°-184° C. (dec.). The NMR spectrum of the product coincides completely with that of the product obtained by Example 1.

EXAMPLE 7

N-(2-Chloroimidazo[1,2-a]pyridin-3-ylsulfonyl)-N'-(4,6-dimethoxy-2-pyrimidinyl)urea (Compound No. 1)

Ethyl N-(2-chloroimidazo[1,2-a]pyridin-3-ylsulfonyl) carbamate (3.1 g) and 2-amino-4,6-dimethoxypyrimidine (1.6 g) are dissolved in 180 ml of chlorobenzene, to which 10 g of molecular sieves (4A) is added and stirred at 80° C. for 17 hours. After colling, insoluble product is filtered off and the filtrate is concentrated under reduced pressure. The residue is purified by silica gel chromatography (eluent: chloroformethyl acetate) to yield 1.3 g of the title compound. The NMR spectrum of the product coincides completely with that of the product obtained by Example 1.

The compounds obtained by a similar way to Examples 1-7 are shown in Tables 17-42.

TABLE 17

General formula

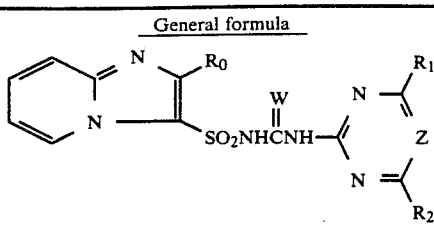

| Compound No. | $R_0$ | W | $R_1$ | $R_2$ | Z | mp (°C.) |
|---|---|---|---|---|---|---|
| 7 | H | O | $CH_3$ | $OCH_3$ | CH | 188-192 |
| 8 | H | O | $OCH_3$ | $OCH_3$ | CH | 197-201 |
| 9 | $CH_3$ | O | $CH_3$ | $OCH_3$ | CH | |
| 10 | $CH_3$ | O | $OCH_3$ | $OCH_3$ | CH | 178-181 |
| 11 | $CH_3$ | O | $CH_3$ | $OCH_3$ | N | 145-153 |
| 12 | $CH_3$ | S | $OCH_3$ | $OCH_3$ | CH | |
| 13 | $C_2H_5$ | O | $OCH_3$ | $OCH_3$ | CH | |
| 14 | n-$C_3H_7$ | O | $OCH_3$ | $OCH_3$ | CH | |
| 15 | i-$C_3H_7$ | O | $OCH_3$ | $OCH_3$ | CH | |
| 16 | $CH_2F$ | O | $OCH_3$ | $OCH_3$ | CH | 191-192 |
| 17 | $CH_2Cl$ | O | $OCH_3$ | $OCH_3$ | CH | 173-175 |
| 18 | $CH_2OCH_3$ | O | $OCH_3$ | $OCH_3$ | CH | 182-183 |
| 19 | $CH_2OC_2H_5$ | O | $OCH_3$ | $OCH_3$ | CH | |
| 20 | $CH_2N(CH_3)_2$ | O | $OCH_3$ | $OCH_3$ | CH | |
| 21 | $CH_2SCH_3$ | O | $OCH_3$ | $OCH_3$ | CH | |
| 22 | $CH_2SC_2H_5$ | O | $OCH_3$ | $OCH_3$ | CH | 144-146 |
| 23 | $CH_2CO_2C_2H_5$ | O | $OCH_3$ | $OCH_3$ | CH | |
| 24 | $CH(OCH_3)_2$ | O | $OCH_3$ | $OCH_3$ | CH | |
| 25 | $CH(OC_2H_5)_2$ | O | $OCH_3$ | $OCH_3$ | CH | |
| 26 | 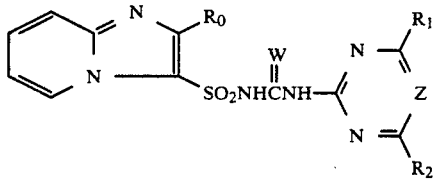 | O | $OCH_3$ | $OCH_3$ | CH | |
| 27 | (S-CH-S ring) | O | $OCH_3$ | $OCH_3$ | CH | |
| 28 | $CCl_3$ | O | $OCH_3$ | $OCH_3$ | CH | |
| 29 | $CF_3$ | O | $OCH_3$ | $OCH_3$ | CH | 187-189 |
| 30 | $CF_3$ | O | Cl | $OCH_3$ | CH | 185-187 |
| 31 | $CH=CH_2$ | O | $OCH_3$ | $OCH_3$ | CH | |
| 32 | $CH=CHCO_2C_2H_5$ | O | $OCH_3$ | $OCH_3$ | CH | |
| 33 | Ph | O | $OCH_3$ | $OCH_3$ | CH | 129-132 |
| 34 | Ph | O | Cl | $OCH_3$ | CH | 143-145 |
| 35 | OH | O | $OCH_3$ | $OCH_3$ | CH | |
| 36 | $OCH_3$ | O | $OCH_3$ | $OCH_3$ | CH | |
| 37 | $OC_2H_5$ | O | $OCH_3$ | $OCH_3$ | CH | |
| 38 | $OC_3H_7$-i | O | $OCH_3$ | $OCH_3$ | CH | |
| 39 | $OCH_2-CH=CH_2$ | O | $OCH_3$ | $OCH_3$ | CH | |
| 40 | $OCHF_2$ | O | $OCH_3$ | $OCH_3$ | CH | |
| 41 | $SCH_3$ | O | $CH_3$ | $OCH_3$ | CH | 174-178 |
| 42 | $SCH_3$ | O | $OCH_3$ | $OCH_3$ | CH | 183-187 |
| 43 | $SC_2H_5$ | O | $OCH_3$ | $OCH_3$ | CH | 171-174 |
| 44 | $SC_3H_7$-n | O | $OCH_3$ | $OCH_3$ | CH | 171-173 |
| 45 | $SC_3H_7$-i | O | $OCH_3$ | $OCH_3$ | CH | |
| 46 | $SCH_2-CH=CH_2$ | O | $OCH_3$ | $OCH_3$ | CH | |
| 47 | SPh | O | $OCH_3$ | $OCH_3$ | CH | |
| 48 | $SOCH_3$ | O | $OCH_3$ | $OCH_3$ | CH | |
| 49 | $SOC_2H_5$ | O | $OCH_3$ | $OCH_3$ | CH | |
| 50 | $SO_2CH_3$ | O | $CH_3$ | $OCH_3$ | CH | 186-190 |
| 51 | $SO_2CH_3$ | O | Cl | $OCH_3$ | CH | 212-214 |
| 52 | $SO_2CH_3$ | O | $OCH_3$ | $OCH_3$ | CH | 199-203 |
| 53 | $SO_2C_2H_5$ | O | $OCH_3$ | $OCH_3$ | CH | |
| 54 | $SO_2C_3H_7$-n | O | $OCH_3$ | $OCH_3$ | CH | |
| 55 | $SO_2Ph$ | O | $OCH_3$ | $OCH_3$ | CH | |
| 56 | $SO_2N(CH_3)_2$ | O | $OCH_3$ | $OCH_3$ | CH | |
| 57 | $SO_2N(C_2H_5)_2$ | O | $OCH_3$ | $OCH_3$ | CH | |
| 58 | $CO_2H$ | O | $OCH_3$ | $OCH_3$ | CH | |
| 59 | $CO_2CH_3$ | O | $CH_3$ | $CH_3$ | CH | |
| 60 | $CO_2CH_3$ | O | $CH_3$ | $OCH_3$ | CH | |
| 61 | $CO_2CH_3$ | O | $OCH_3$ | $OCH_3$ | CH | |
| 62 | $CO_2CH_3$ | O | Cl | $OCH_3$ | CH | |

TABLE 17-continued

General formula:

[Structure: pyridine-N=C(R0)-C(SO2NHC(=W)NH-pyrimidine with R1, R2, Z)]

| Compound No. | R0 | W | R1 | R2 | Z | mp (°C.) |
|---|---|---|---|---|---|---|
| 63 | CO2CH3 | O | CH3 | OCH3 | N | |
| 64 | CO2CH3 | S | OCH3 | OCH3 | CH | |
| 65 | CO2C2H5 | O | CH3 | CH3 | CH | |
| 66 | CO2C2H5 | O | CH3 | OCH3 | CH | 165~167 |
| 67 | CO2C2H5 | O | OCH3 | OCH3 | CH | 161~163 |
| 68 | CO2C2H5 | O | Cl | OCH3 | CH | |
| 69 | CO2C2H5 | O | CH3 | OCH3 | N | |
| 70 | CO2C2H5 | S | OCH3 | OCH3 | CH | |
| 71 | CO2C3H7-n | O | CH3 | OCH3 | CH | |
| 72 | CO2C3H7-n | O | OCH3 | OCH3 | CH | |
| 73 | CO2C3H7-n | S | OCH3 | OCH3 | CH | |
| 74 | CO2C3H7-i | O | CH3 | OCH3 | CH | |
| 75 | CO2C3H7-i | O | OCH3 | OCH3 | CH | |
| 76 | CO2C3H7-i | S | OCH3 | OCH3 | CH | |
| 77 | CO2C4H9-n | O | CH3 | OCH3 | CH | |
| 78 | CO2C4H9-n | O | OCH3 | OCH3 | CH | |
| 79 | CO2C4H9-n | S | OCH3 | OCH3 | CH | |
| 80 | CO2C4H9-t | O | CH3 | OCH3 | CH | |
| 81 | CO2C4H9-t | O | OCH3 | OCH3 | CH | |
| 82 | CO2C4H9-t | S | OCH3 | OCH3 | CH | |
| 83 | CON(CH3)2 | O | CH3 | OCH3 | CH | |
| 84 | CON(CH3)2 | O | OCH3 | OCH3 | CH | |
| 85 | CON(CH3)2 | S | OCH3 | OCH3 | CH | |
| 86 | CHO | O | OCH3 | OCH3 | CH | |
| 87 | COCH3 | O | OCH3 | OCH3 | CH | |
| 88 | CN | O | OCH3 | OCH3 | CH | 205~210 |
| 89 | F | O | CH3 | CH3 | CH | |
| 90 | F | O | CH3 | OCH3 | CH | 166~168 |
| 91 | F | O | Cl | OCH3 | CH | 169~170 |
| 92 | F | O | OCH3 | OCH3 | CH | 175~177 |
| 93 | F | O | CH3 | OCH3 | N | |
| 94 | F | S | OCH3 | OCH3 | CH | |
| 95 | Cl | O | CH3 | CH3 | CH | |
| 96 | Cl | O | Cl | OCH3 | CH | 157~160 |
| 97 | Cl | O | CH3 | OCH3 | N | |
| 98 | Br | O | OCH3 | OCH3 | CH | 195~196 |

TABLE 18

General formula:

[Structure: bicyclic pyridine (positions 1,4,5,6,7,8) with R1, R2 substituents, connected via N=C(R0)-C(SO2NHCONH-pyrimidine with R3, OCH3)]

| Compound No. | R0 | R1 | R2 | R3 | mp(°C.) |
|---|---|---|---|---|---|
| 99 | CH3 | 6-CH3 | H | OCH3 | |
| 100 | CH3 | 6-Cl | H | CH3 | 168~172 |
| 101 | CH3 | 6-Cl | H | OCH3 | 204~208 |
| 102 | Cl | 5-CH3 | H | OCH3 | |
| 103 | Cl | 6-CH3 | H | CH3 | 151~155 |

TABLE 18-continued

General formula:

[Same as TABLE 18]

| Compound No. | R0 | R1 | R2 | R3 | mp(°C.) |
|---|---|---|---|---|---|
| 104 | Cl | 6-CH3 | H | OCH3 | 178~182 |
| 105 | Cl | 7-CH3 | H | OCH3 | |
| 106 | Cl | 8-CH3 | H | OCH3 | |
| 107 | Cl | 6-Cl | H | OCH3 | 172~174 |
| 108 | Cl | 6-Cl | H | Cl | 211~213 |
| 109 | Cl | 6-Br | H | OCH3 | |
| 110 | Cl | 6-CF3 | H | OCH3 | 193~195 |
| 111 | Cl | 8-NO2 | H | OCH3 | |
| 112 | Cl | 5-CH3 | 7-CH3 | OCH3 | |
| 113 | Cl | 6-Cl | 8-Cl | OCH3 | |
| 114 | CO2CH3 | 5-CH3 | H | OCH3 | |
| 115 | CO2CH3 | 6-CH3 | H | OCH3 | |
| 116 | CO2CH3 | 6-Cl | H | OCH3 | |
| 117 | CO2C2H5 | 6-CH3 | H | OCH3 | |
| 118 | CO2C2H5 | 6-Cl | H | OCH3 | |

TABLE 19

General formula:

[Structure: partially hydrogenated pyridine-N=C(R0)-C(SO2NHCONH-pyrimidine with R1, R2)]

| Compound No. | R0 | R1 | R2 | mp(°C.) |
|---|---|---|---|---|
| 119 | H | CH3 | OCH3 | |
| 120 | H | OCH3 | OCH3 | |
| 121 | CH3 | CH3 | OCH3 | |
| 122 | CH3 | OCH3 | OCH3 | |
| 123 | Cl | CH3 | OCH3 | |
| 124 | Cl | OCH3 | OCH3 | |
| 125 | CO2CH3 | CH3 | OCH3 | |
| 126 | CO2CH3 | OCH3 | OCH3 | |
| 127 | CO2C2H5 | CH3 | OCH3 | |
| 128 | CO2C2H5 | OCH3 | OCH3 | |

TABLE 20

General formula:

[Structure: piperidine-N=C(R0)-C(SO2NHCONH-pyrimidine with R1, R2)]

| Compound No. | R0 | R1 | R2 | mp(°C.) |
|---|---|---|---|---|
| 129 | H | OCH3 | OCH3 | |
| 130 | CH3 | CH3 | CH3 | |
| 131 | CH3 | OCH3 | OCH3 | |
| 132 | Cl | CH3 | CH3 | |
| 133 | Cl | CH3 | OCH3 | |
| 134 | Cl | OCH3 | OCH3 | |
| 135 | CO2CH3 | CH3 | OCH3 | |
| 136 | CO2CH3 | OCH3 | OCH3 | |

TABLE 20-continued

General formula

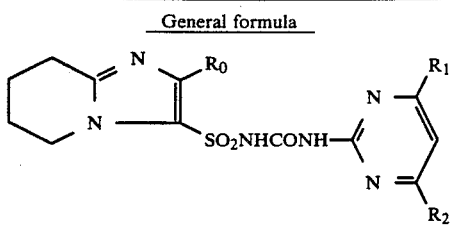

| Compound No. | $R_0$ | $R_1$ | $R_2$ | mp(°C.) |
|---|---|---|---|---|
| 137 | $CO_2C_2H_5$ | $CH_3$ | $OCH_3$ | |
| 138 | $CO_2C_2H_5$ | $OCH_3$ | $OCH_3$ | |

TABLE 21

General formula

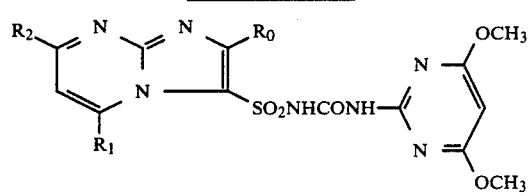

| Compound No. | $R_0$ | $R_1$ | $R_2$ | mp(°C.) |
|---|---|---|---|---|
| 139 | H | H | H | |
| 140 | H | $CH_3$ | $CH_3$ | |
| 141 | $CH_3$ | H | H | 210~212 |
| 142 | $CH_3$ | $CH_3$ | $CH_3$ | |
| 143 | Cl | H | H | |
| 144 | Cl | $CH_3$ | $CH_3$ | |
| 145 | $CO_2CH_3$ | H | H | |
| 146 | $CO_2CH_3$ | $CH_3$ | $CH_3$ | |
| 147 | $CO_2C_2H_5$ | H | H | |
| 148 | $CO_2C_2H_5$ | $CH_3$ | $CH_3$ | |

TABLE 22

General formula

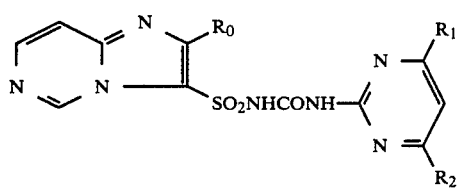

| Compound No. | $R_0$ | $R_1$ | $R_2$ | mp(°C.) |
|---|---|---|---|---|
| 149 | H | $CH_3$ | $OCH_3$ | |
| 150 | H | $OCH_3$ | $OCH_3$ | |
| 151 | $CH_3$ | $CH_3$ | $OCH_3$ | |
| 152 | $CH_3$ | $OCH_3$ | $OCH_3$ | |
| 153 | Cl | $CH_3$ | $OCH_3$ | |
| 154 | Cl | $OCH_3$ | $OCH_3$ | |
| 155 | $CO_2CH_3$ | $CH_3$ | $OCH_3$ | |
| 156 | $CO_2CH_3$ | $OCH_3$ | $OCH_3$ | |
| 157 | $CO_2C_2H_5$ | $CH_3$ | $OCH_3$ | |
| 158 | $CO_2C_2H_5$ | $OCH_3$ | $OCH_3$ | |

TABLE 23

General formula

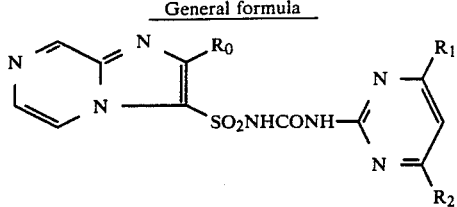

| Compound No. | $R_0$ | $R_1$ | $R_2$ | mp(°C.) |
|---|---|---|---|---|
| 159 | H | $CH_3$ | $OCH_3$ | |
| 160 | H | $OCH_3$ | $OCH_3$ | |
| 161 | $CH_3$ | $CH_3$ | $OCH_3$ | |
| 162 | $CH_3$ | $OCH_3$ | $OCH_3$ | |
| 163 | Cl | $CH_3$ | $OCH_3$ | |
| 164 | Cl | $OCH_3$ | $OCH_3$ | |
| 165 | $CO_2CH_3$ | $CH_3$ | $OCH_3$ | |
| 166 | $CO_2CH_3$ | $OCH_3$ | $OCH_3$ | |
| 167 | $CO_2C_2H_5$ | $CH_3$ | $OCH_3$ | |
| 168 | $CO_2C_2H_5$ | $OCH_3$ | $OCH_3$ | |

TABLE 24

General formula

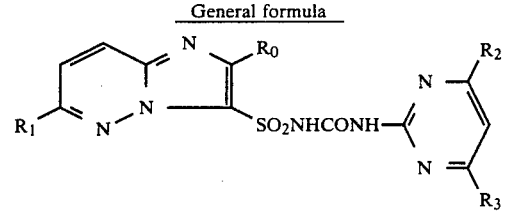

| Compound No. | $R_0$ | $R_1$ | $R_2$ | $R_3$ | mp. (°C.) |
|---|---|---|---|---|---|
| 169 | H | H | $OCH_3$ | $OCH_3$ | |
| 170 | H | Cl | $OCH_3$ | $OCH_3$ | |
| 171 | $CH_3$ | $CH_3$ | $OCH_3$ | $OCH_3$ | |
| 172 | $CH_3$ | H | $CH_3$ | $OCH_3$ | 168~170 (decomp.) |
| 173 | $CH_3$ | H | $OCH_3$ | $OCH_3$ | 173~175 (decomp.) |
| 174 | $CH_3$ | $CH_3$ | $OCH_3$ | $OCH_3$ | |
| 175 | $CH_3$ | Cl | $CH_3$ | $OCH_3$ | 201~204 (decomp.) |
| 176 | $CH_3$ | Cl | $OCH_3$ | $OCH_3$ | 187~189 (decomp.) |
| 177 | $CH_3$ | Cl | Cl | $OCH_3$ | 177~179 (decomp.) |
| 178 | $CH_3$ | Cl | $CH_3$ | $CH_3$ | 208~210 (decomp.) |
| 179 | $CH_3$ | $(CH_3)_2N$ | $CH_3$ | $OCH_3$ | 220 |
| 180 | $CH_3$ | $(CH_3)_2N$ | Cl | $OCH_3$ | 165~167 |
| 181 | $CH_3$ | $(CH_3)_2N$ | $OCH_3$ | $OCH_3$ | 183~185 (decomp.) |
| 182 | $CH_3$ | morpholino | $CH_3$ | $OCH_3$ | |
| 183 | $CH_3$ | morpholino | $OCH_3$ | $OCH_3$ | |
| 184 | $CH_3$ | $CH_3O$ | $CH_3$ | $OCH_3$ | 239~241 |
| 185 | $CH_3$ | $CH_3O$ | Cl | $OCH_3$ | 251 |
| 186 | $CH_3$ | $CH_3O$ | $OCH_3$ | $OCH_3$ | 241 |
| 187 | $CH_3$ | $C_2H_5O$ | $OCH_3$ | $OCH_3$ | |
| 188 | $CH_3$ | $i-C_3H_7O$ | $OCH_3$ | $OCH_3$ | |
| 189 | $CH_3$ | $CH_3S$ | $CH_3$ | $OCH_3$ | |
| 190 | $CH_3$ | $CH_3S$ | $OCH_3$ | $OCH_3$ | 178~180 |

TABLE 24-continued

General formula

[Structure: pyridazine fused ring with $R_1$, $R_0$, SO$_2$NHCONH-pyrimidine with $R_2$, $R_3$]

| Compound No. | $R_0$ | $R_1$ | $R_2$ | $R_3$ | mp. (°C.) |
|---|---|---|---|---|---|
| 191 | CH$_3$ | CH$_3$SO | OCH$_3$ | OCH$_3$ | (decomp.) 180~182 |
| 192 | CH$_3$ | CH$_3$SO$_2$ | OCH$_3$ | OCH$_3$ | (decomp.) |
| 193 | Cl | H | OCH$_3$ | OCH$_3$ | |
| 194 | Cl | CH$_3$ | OCH$_3$ | OCH$_3$ | |
| 195 | Cl | Cl | CH$_3$ | CH$_3$ | |
| 196 | Cl | Cl | CH$_3$ | OCH$_3$ | |
| 197 | Cl | Cl | Cl | OCH$_3$ | |
| 198 | Cl | Cl | OCH$_3$ | OCH$_3$ | 201~203 |
| 199 | Cl | CH$_3$O | CH$_3$ | OCH$_3$ | 164~166 |
| 200 | Cl | CH$_3$O | Cl | OCH$_3$ | |
| 201 | Cl | CH$_3$O | OCH$_3$ | OCH$_3$ | 190~193 |
| 202 | Cl | (CH$_3$)$_2$N | CH$_3$ | OCH$_3$ | |
| 203 | Cl | (CH$_3$)$_2$N | OCH$_3$ | OCH$_3$ | 193~195 |
| 204 | Cl | morpholino (O-N ring) | OCH$_3$ | OCH$_3$ | |
| 205 | Cl | CH$_3$S | CH$_3$ | OCH$_3$ | 172~174 |
| 206 | Cl | CH$_3$S | Cl | OCH$_3$ | |
| 207 | Cl | CH$_3$S | OCH$_3$ | OCH$_3$ | 163~165 |
| 208 | Cl | C$_2$H$_5$S | CH$_3$ | OCH$_3$ | |
| 209 | Cl | C$_2$H$_5$S | OCH$_3$ | OCH$_3$ | 180~182 |
| 210 | Cl | CH$_3$SO$_2$ | OCH$_3$ | OCH$_3$ | 180~182 |
| 211 | Cl | C$_2$H$_5$SO$_2$ | OCH$_3$ | OCH$_3$ | |
| 212 | CO$_2$C$_2$H$_5$ | H | OCH$_3$ | OCH$_3$ | |
| 213 | CO$_2$C$_2$H$_5$ | H | CH$_3$ | OCH$_3$ | |
| 214 | CO$_2$C$_2$H$_5$ | CH$_3$ | OCH$_3$ | OCH$_3$ | |
| 215 | CO$_2$C$_2$H$_5$ | Cl | CH$_3$ | OCH$_3$ | |
| 216 | CO$_2$C$_2$H$_5$ | Cl | Cl | OCH$_3$ | |
| 217 | CO$_2$C$_2$H$_5$ | Cl | OCH$_3$ | OCH$_3$ | 171~173 |
| 218 | CO$_2$C$_2$H$_5$ | CH$_3$O | OCH$_3$ | OCH$_3$ | |
| 219 | CO$_2$C$_2$H$_5$ | C$_2$H$_5$O | OCH$_3$ | CH$_3$ | |
| 220 | CO$_2$C$_2$H$_5$ | (CH$_3$)$_2$N | OCH$_3$ | OCH$_3$ | |
| 221 | CO$_2$C$_2$H$_5$ | CH$_3$S | OCH$_3$ | OCH$_3$ | |
| 222 | CO$_2$C$_2$H$_5$ | CH$_3$SO$_2$ | OCH$_3$ | OCH$_3$ | |
| 223 | CO$_2$C$_2$H$_5$ | C$_2$H$_5$S | OCH$_3$ | OCH$_3$ | |
| 224 | CO$_2$C$_2$H$_5$ | C$_2$H$_5$SO$_2$ | OCH$_3$ | OCH$_3$ | |

TABLE 25

General formula

[Structure: triazine fused ring with $R_0$, SO$_2$NHCONH-pyrimidine with $R_1$, $R_2$]

| Compound No. | $R_0$ | $R_1$ | $R_2$ | mp (°C.) |
|---|---|---|---|---|
| 225 | H | CH$_3$ | OCH$_3$ | |
| 226 | H | OCH$_3$ | OCH$_3$ | |
| 227 | CH$_3$ | CH$_3$ | OCH$_3$ | |
| 228 | CH$_3$ | OCH$_3$ | OCH$_3$ | |
| 229 | Cl | CH$_3$ | OCH$_3$ | |
| 230 | Cl | OCH$_3$ | OCH$_3$ | |
| 231 | CO$_2$CH$_3$ | CH$_3$ | OCH$_3$ | |
| 232 | CO$_2$CH$_3$ | OCH$_3$ | OCH$_3$ | |

TABLE 25-continued

General formula

[Structure: triazine fused ring with $R_0$, SO$_2$NHCONH-pyrimidine with $R_1$, $R_2$]

| Compound No. | $R_0$ | $R_1$ | $R_2$ | mp (°C.) |
|---|---|---|---|---|
| 233 | CO$_2$C$_2$H$_5$ | CH$_3$ | OCH$_3$ | |
| 234 | CO$_2$C$_2$H$_5$ | OCH$_3$ | OCH$_3$ | |

TABLE 26

General formula

[Structure: imidazo fused ring with $R_1$, $R_0$, SO$_2$NHCONH-pyrimidine with $R_2$, OCH$_3$]

| Compound No. | $R_0$ | $R_1$ | $R_2$ | mp (°C.) |
|---|---|---|---|---|
| 235 | H | CH$_3$ | OCH$_3$ | |
| 236 | CH$_3$ | H | OCH$_3$ | |
| 237 | CH$_3$ | CH$_3$ | CH$_3$ | 128~130 (decomp.) |
| 238 | CH$_3$ | CH$_3$ | OCH$_3$ | 130~132 (decomp.) |
| 239 | Cl | H | OCH$_3$ | |
| 240 | Cl | CH$_3$ | CH$_3$ | |
| 241 | Cl | CH$_3$ | OCH$_3$ | |
| 242 | CO$_2$CH$_3$ | H | OCH$_3$ | |
| 243 | CO$_2$CH$_3$ | CH$_3$ | CH$_3$ | |
| 244 | CO$_2$CH$_3$ | CH$_3$ | OCH$_3$ | |
| 245 | CO$_2$C$_2$H$_5$ | H | OCH$_3$ | |
| 246 | CO$_2$C$_2$H$_5$ | CH$_3$ | CH$_3$ | |
| 247 | CO$_2$C$_2$H$_5$ | CH$_3$ | OCH$_3$ | |

TABLE 27

General formula

[Structure: triazine fused ring with $R_1$-N, $R_0$, SO$_2$NHCONH-pyrimidine with $R_3$, OCH$_3$]

| Compound No. | $R_0$ | $R_1$ | $R_3$ | mp (°C.) |
|---|---|---|---|---|
| 248 | H | CH$_3$ | OCH$_3$ | |
| 249 | CH$_3$ | H | OCH$_3$ | |
| 250 | CH$_3$ | CH$_3$ | OCH$_3$ | |
| 251 | Cl | H | OCH$_3$ | |
| 252 | Cl | CH$_3$ | CH$_3$ | |
| 253 | Cl | CH$_3$ | OCH$_3$ | |
| 254 | Cl | CH$_3$ | OCH$_3$ | |
| 255 | Cl | CH$_3$ | OCH$_3$ | |
| 256 | CO$_2$CH$_3$ | H | OCH$_3$ | |
| 257 | CO$_2$CH$_3$ | CH$_3$ | CH$_3$ | |
| 258 | CO$_2$CH$_3$ | CH$_3$ | OCH$_3$ | |
| 259 | CO$_2$C$_2$H$_5$ | H | OCH$_3$ | |
| 260 | CO$_2$C$_2$H$_5$ | CH$_3$ | CH$_3$ | |
| 261 | CO$_2$C$_2$H$_5$ | CH$_3$ | OCH$_3$ | |

TABLE 28

General formula

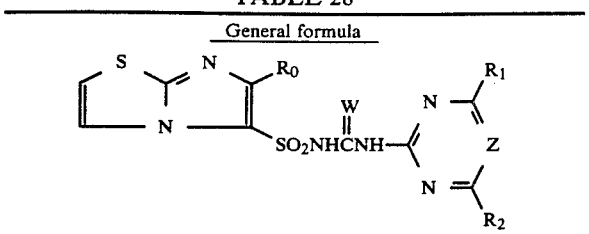

| Compound No. | $R_0$ | W | $R_1$ | $R_2$ | Z | mp (°C.) |
|---|---|---|---|---|---|---|
| 262 | H | O | $CH_3$ | $CH_3$ | CH | |
| 263 | H | O | $CH_3$ | $OCH_3$ | CH | |
| 264 | H | O | $OCH_3$ | $OCH_3$ | CH | |
| 265 | $CH_3$ | O | $CH_3$ | $CH_3$ | CH | |
| 266 | $CH_3$ | O | $CH_3$ | $OCH_3$ | CH | |
| 267 | $CH_3$ | S | $CH_3$ | $OCH_3$ | CH | |
| 268 | $C_2H_5$ | O | $CH_3$ | $OCH_3$ | CH | 190~192 |
| 269 | $C_2H_5$ | O | Cl | $OCH_3$ | CH | 182~184 |
| 270 | $C_2H_5$ | O | $OCH_3$ | $OCH_3$ | CH | 173~175 |
| 271 | $C_2H_5$ | O | $CH_3$ | $CH_3$ | CH | 182~184 |
| 272 | n-$C_3H_7$ | O | $CH_3$ | $OCH_3$ | CH | 166~167 |
| 273 | n-$C_3H_7$ | O | Cl | $OCH_3$ | CH | 164~165 |
| 274 | n-$C_3H_7$ | O | $OCH_3$ | $OCH_3$ | CH | 158~160 |
| 275 | $CH_2Cl$ | O | $OCH_3$ | $OCH_3$ | CH | 290 |
| 276 | $CH_2Cl$ | O | $CH_3$ | $OCH_3$ | CH | 194~195 |
| 277 | $CH_2OCH_3$ | O | $OCH_3$ | $OCH_3$ | CH | |
| 278 | $CH_2OC_2H_5$ | O | $OCH_3$ | $OCH_3$ | CH | |
| 279 | $CH_2N(CH_3)_2$ | O | $OCH_3$ | $OCH_3$ | CH | |
| 280 | $CH_2SCH_3$ | O | $OCH_3$ | $OCH_3$ | H | |
| 281 | $CH_2SC_2H_5$ | O | $OCH_3$ | $OCH_3$ | CH | |
| 282 | $CCl_3$ | O | $OCH_3$ | $OCH_3$ | CH | |
| 283 | $CF_3$ | O | $CH_3$ | $OCH_3$ | CH | 210~212 |
| 284 | $CF_3$ | O | Cl | $OCH_3$ | CH | |
| 285 | $CF_3$ | O | $OCH_3$ | $OCH_3$ | CH | 213~215 |
| 286 | $CH=CH_2$ | O | $OCH_3$ | $OCH_3$ | CH | |
| 287 | $CH=CHCH_3$ | O | $OCH_3$ | $OCH_3$ | CH | |
| 288 | Ph | O | $OCH_3$ | $OCH_3$ | CH | |
| 289 | OH | O | $OCH_3$ | $OCH_3$ | CH | |
| 290 | $OCH_3$ | O | $OCH_3$ | $OCH_3$ | CH | |
| 291 | $OC_2H_5$ | O | $OCH_3$ | $OCH_3$ | CH | |
| 292 | $OCHF_2$ | O | $OCH_3$ | $OCH_3$ | CH | |
| 293 | $SCH_3$ | O | $CH_3$ | $OCH_3$ | CH | |
| 294 | $SCH_3$ | O | $OCH_3$ | $OCH_3$ | CH | 183~185 |
| 295 | $SC_2H_5$ | O | $CH_3$ | $OCH_3$ | CH | |
| 296 | $SC_2H_5$ | O | $OCH_3$ | $OCH_3$ | CH | |
| 297 | $SC_3H_7$-n | O | $CH_3$ | $OCH_3$ | CH | |
| 298 | $SC_3H_7$-n | O | $OCH_3$ | $OCH_3$ | CH | |
| 299 | $SC_3H_7$-i | O | $CH_3$ | $OCH_3$ | CH | |
| 300 | $SC_3H_7$-i | O | $OCH_3$ | $OCH_3$ | CH | |
| 301 | $SCH_2-CH=CH_2$ | O | $OCH_3$ | $OCH_3$ | CH | |
| 302 | SPh | O | $CH_3$ | $OCH_3$ | CH | |
| 303 | SPh | O | $OCH_3$ | $OCH_3$ | CH | |
| 304 | $SOCH_3$ | O | $CH_3$ | $OCH_3$ | CH | 204~206 |
| 305 | $SOCH_3$ | O | $OCH_3$ | $OCH_3$ | CH | 189~190 |
| 306 | $SOCH_3$ | O | Cl | $OCH_3$ | CH | 220~223 |
| 307 | $SOC_2H_5$ | O | $CH_3$ | $OCH_3$ | CH | |
| 308 | $SOC_2H_5$ | O | $OCH_3$ | $OCH_3$ | CH | |
| 309 | $SO_2CH_3$ | O | Cl | $OCH_3$ | CH | 209~212 |
| 310 | $SO_2CH_3$ | O | $OCH_3$ | $OCH_3$ | CH | 192~194 |
| 311 | $SO_2C_2H_5$ | O | $CH_3$ | $OCH_3$ | CH | |
| 312 | $SO_2C_2H_5$ | O | $OCH_3$ | $OCH_3$ | CH | |
| 313 | $SO_2N(CH_3)_2$ | O | $CH_3$ | $OCH_3$ | CH | |
| 314 | $SO_2N(CH_3)_2$ | O | $OCH_3$ | $OCH_3$ | CH | |
| 315 | $SO_2N(C_2H_5)_2$ | O | $CH_3$ | $OCH_3$ | CH | |
| 316 | $SO_2N(C_2H_5)_2$ | O | $OCH_3$ | $OCH_3$ | CH | |
| 317 | $CO_2H$ | O | $OCH_3$ | $OCH_3$ | CH | |
| 318 | $CO_2CH_3$ | O | $CH_3$ | $CH_3$ | CH | |
| 319 | $CO_2CH_3$ | O | $CH_3$ | $OCH_3$ | CH | |
| 320 | $CO_2CH_3$ | O | Cl | $OCH_3$ | CH | |
| 321 | $CO_2CH_3$ | O | $OCH_3$ | $OCH_3$ | CH | |
| 322 | $CO_2CH_3$ | O | $CH_3$ | $OCH_3$ | N | |
| 323 | $CO_2CH_3$ | S | $OCH_3$ | $OCH_3$ | CH | |
| 324 | $CO_2C_2H_5$ | O | $CH_3$ | $CH_3$ | CH | |
| 325 | $CO_2C_2H_5$ | O | $CH_3$ | $OCH_3$ | CH | |
| 326 | $CO_2C_2H_5$ | O | Cl | $OCH_3$ | CH | |
| 327 | $CO_2C_2H_5$ | O | $OCH_3$ | $OCH_3$ | CH | |
| 328 | $CO_2C_2H_5$ | O | $CH_3$ | $OCH_3$ | N | |
| 329 | $CO_2C_2H_5$ | S | $OCH_3$ | $OCH_3$ | CH | |
| 330 | $CO_2C_3H_7$-n | O | $CH_3$ | $OCH_3$ | CH | |
| 331 | $CO_2C_3H_7$-n | O | $OCH_3$ | $OCH_3$ | CH | |
| 332 | $CO_2C_3H_7$-n | S | $OCH_3$ | $OCH_3$ | CH | |
| 333 | $CO_2C_3H_7$-i | O | $CH_3$ | $CH_3$ | CH | |
| 334 | $CO_2C_3H_7$-i | O | $OCH_3$ | $OCH_3$ | CH | |
| 335 | $CO_2C_3H_7$-i | S | $OCH_3$ | $OCH_3$ | CH | |
| 336 | $CO_2C_4H_9$-n | O | $CH_3$ | $OCH_3$ | CH | |
| 337 | $CO_2C_4H_9$-n | O | $OCH_3$ | $OCH_3$ | CH | |
| 338 | $CO_2C_4H_9$-n | S | $OCH_3$ | $OCH_3$ | CH | |
| 339 | $CO_2C_4H_9$-t | O | $CH_3$ | $OCH_3$ | CH | |
| 340 | $CO_2C_4H_9$-t | O | $OCH_3$ | $OCH_3$ | CH | |
| 341 | $CO_2C_4H_9$-t | S | $OCH_3$ | $OCH_3$ | CH | |
| 342 | $CON(CH_3)_2$ | O | $CH_3$ | $OCH_3$ | CH | |
| 343 | $CON(CH_3)_2$ | O | $OCH_3$ | $OCH_3$ | CH | |
| 344 | $CON(CH_3)_2$ | S | $OCH_3$ | $OCH_3$ | CH | |
| 345 | CN | O | $OCH_3$ | $OCH_3$ | CH | |
| 346 | F | O | $CH_3$ | $OCH_3$ | CH | |
| 347 | F | O | $OCH_3$ | $OCH_3$ | CH | 200~201 |
| 348 | Cl | O | $CH_3$ | $CH_3$ | CH | 201~203 |
| 349 | Cl | O | $CH_3$ | $OCH_3$ | CH | 198~200 |
| 350 | Cl | O | $OCH_3$ | $OCH_3$ | CH | 202~204 |
| 351 | Cl | S | $OCH_3$ | $OCH_3$ | CH | |
| 352 | Br | O | $CH_3$ | $OCH_3$ | CH | |
| 353 | Br | O | $OCH_3$ | $OCH_3$ | CH | 204~206 |

TABLE 29

General formula

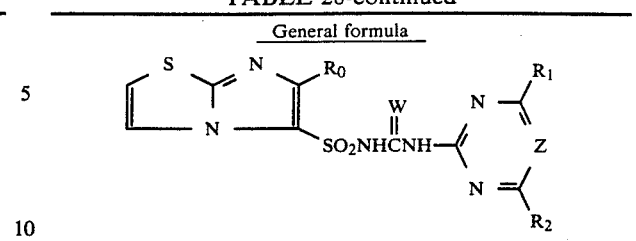

| Compound No. | $R_0$ | $R_1$ | $R_2$ | $R_3$ | mp (°C.) |
|---|---|---|---|---|---|
| 354 | $CH_3$ | $CH_3$ | H | $CH_3$ | 171~173 |
| 355 | $CH_3$ | $CH_3$ | H | $OCH_3$ | 182~184 |
| 356 | Cl | $CH_3$ | H | $CH_3$ | 188~190 |
| 357 | Cl | $CH_3$ | H | $OCH_3$ | 185~187 |

TABLE 29-continued

General formula $R_2, R_1$ substituted thiazole fused with imidazole bearing $R_0$ and $SO_2NHCONH$-pyrimidine with $R_3$ and $OCH_3$

| Compound No. | $R_0$ | $R_1$ | $R_2$ | $R_3$ | mp (°C.) |
|---|---|---|---|---|---|
| 358 | Cl | CH$_3$ | CH$_3$ | CH$_3$ | |
| 359 | Cl | CH$_3$ | CH$_3$ | OCH$_3$ | |
| 360 | Cl | –CH=CH–CH=CH– | | CH$_3$ | 187~188 |
| 361 | Cl | –CH=CH–CH=CH– | | OCH$_3$ | 183~185 |
| 362 | CH$_3$ | CO$_2$C$_2$H$_5$ | H | CH$_3$ | |
| 363 | CH$_3$ | CO$_2$C$_2$H$_5$ | H | OCH$_3$ | |
| 364 | CO$_2$CH$_3$ | CH$_3$ | H | CH$_3$ | |
| 365 | CO$_2$CH$_3$ | CH$_3$ | H | OCH$_3$ | |
| 366 | CO$_2$C$_2$H$_5$ | CH$_3$ | H | CH$_3$ | |
| 367 | CO$_2$C$_2$H$_5$ | CH$_3$ | H | OCH$_3$ | |
| 368 | H | CH$_3$ | H | CH$_3$ | 118~119 |
| 369 | H | CH$_3$ | H | OCH$_3$ | 173~175 |

TABLE 30

General formula

| Compound No. | $R_0$ | $R_1$ | $R_2$ | mp (°C.) |
|---|---|---|---|---|
| 370 | H | CH$_3$ | OCH$_3$ | |
| 371 | H | OCH$_3$ | OCH$_3$ | |
| 372 | CH$_3$ | CH$_3$ | OCH$_3$ | |
| 373 | CH$_3$ | OCH$_3$ | OCH$_3$ | |
| 374 | Cl | CH$_3$ | OCH$_3$ | |
| 375 | Cl | OCH$_3$ | OCH$_3$ | 109~111 |
| 376 | CO$_2$CH$_3$ | CH$_3$ | OCH$_3$ | |
| 377 | CO$_2$CH$_3$ | OCH$_3$ | OCH$_3$ | |
| 378 | CO$_2$C$_2$H$_5$ | CH$_3$ | OCH$_3$ | 165~167 |
| 379 | CO$_2$C$_2$H$_5$ | OCH$_3$ | OCH$_3$ | 175~177 |
| 380 | CO$_2$C$_2$H$_5$ | Cl | OCH$_3$ | 128~130 |

TABLE 31

General formula

| Compound No. | $R_0$ | n | $R_1$ | $R_2$ | mp (°C.) |
|---|---|---|---|---|---|
| 381 | H | 0 | OCH$_3$ | OCH$_3$ | |
| 382 | H | 1 | OCH$_3$ | OCH$_3$ | |
| 383 | H | 1 | OCH$_3$ | OCH$_3$ | |
| 384 | H | 2 | OCH$_3$ | OCH$_3$ | |
| 385 | CH$_3$ | 0 | CH$_3$ | OCH$_3$ | |
| 386 | CH$_3$ | 0 | OCH$_3$ | OCH$_3$ | |
| 387 | CH$_3$ | 1 | OCH$_3$ | OCH$_3$ | |
| 388 | CH$_3$ | 2 | OCH$_3$ | OCH$_3$ | |
| 389 | Cl | 0 | CH$_3$ | CH$_3$ | 195~197 (decomp.) |
| 390 | Cl | 0 | CH$_3$ | OCH$_3$ | 192~195 (decomp.) |
| 391 | Cl | 0 | OCH$_3$ | OCH$_3$ | 210~212 |
| 392 | Cl | 1 | CH$_3$ | OCH$_3$ | |
| 393 | Cl | 1 | OCH$_3$ | OCH$_3$ | 210~212 (decomp.) |
| 394 | Cl | 2 | CH$_3$ | OCH$_3$ | |
| 395 | Cl | 2 | OCH$_3$ | OCH$_3$ | 222~225 (decomp.) |
| 396 | CO$_2$CH$_3$ | 0 | CH$_3$ | OCH$_3$ | |
| 397 | CO$_2$CH$_3$ | 0 | OCH$_3$ | OCH$_3$ | |
| 398 | CO$_2$CH$_3$ | 1 | OCH$_3$ | OCH$_3$ | |
| 399 | CO$_2$CH$_3$ | 2 | CH$_3$ | OCH$_3$ | |
| 400 | CO$_2$CH$_3$ | 2 | OCH$_3$ | OCH$_3$ | |
| 401 | CO$_2$C$_2$H$_5$ | 0 | CH$_3$ | OCH$_3$ | |
| 402 | CO$_2$C$_2$H$_5$ | 0 | OCH$_3$ | OCH$_3$ | |
| 403 | CO$_2$C$_2$H$_5$ | 1 | OCH$_3$ | OCH$_3$ | |
| 404 | CO$_2$C$_2$H$_5$ | 2 | CH$_3$ | OCH$_3$ | |
| 405 | CO$_2$C$_2$H$_5$ | 2 | OCH$_3$ | OCH$_3$ | |

TABLE 32

General formula

| Compound No. | $R_0$ | $R_1$ | $R_2$ | $R_3$ | mp (°C.) |
|---|---|---|---|---|---|
| 406 | H | H | OCH$_3$ | OCH$_3$ | |
| 407 | CH$_3$ | H | CH$_3$ | OCH$_3$ | |
| 408 | CH$_3$ | H | OCH$_3$ | OCH$_3$ | 201~204 |
| 409 | CH$_3$ | SCH$_3$ | OCH$_3$ | OCH$_3$ | |
| 410 | Cl | H | CH$_3$ | OCH$_3$ | |
| 411 | Cl | H | OCH$_3$ | OCH$_3$ | |
| 412 | Cl | CH$_3$ | OCH$_3$ | OCH$_3$ | |
| 413 | Cl | SCH$_3$ | OCH$_3$ | OCH$_3$ | |
| 414 | CO$_2$CH$_3$ | H | CH$_3$ | OCH$_3$ | |
| 415 | CO$_2$CH$_3$ | H | OCH$_3$ | OCH$_3$ | |
| 416 | CO$_2$CH$_3$ | CH$_3$ | OCH$_3$ | OCH$_3$ | |
| 417 | CO$_2$CH$_3$ | SCH$_3$ | OCH$_3$ | OCH$_3$ | |
| 418 | CO$_2$C$_2$H$_5$ | H | CH$_3$ | CH$_3$ | |
| 419 | CO$_2$C$_2$H$_5$ | H | CH$_3$ | OCH$_3$ | |
| 420 | CO$_2$C$_2$H$_5$ | H | OCH$_3$ | OCH$_3$ | |
| 421 | CO$_2$C$_2$H$_5$ | CH$_3$ | OCH$_3$ | OCH$_3$ | |
| 422 | CO$_2$C$_2$H$_5$ | SCH$_3$ | OCH$_3$ | OCH$_3$ | |

TABLE 33

General formula

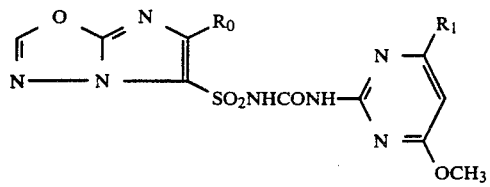

| Compound No. | R₀ | R₁ | mp (°C.) |
|---|---|---|---|
| 423 | H | OCH₃ | |
| 424 | CH₃ | CH₃ | |
| 425 | CH₃ | OCH₃ | |
| 426 | Cl | CH₃ | |
| 427 | Cl | OCH₃ | |
| 428 | CO₂CH₃ | OCH₃ | |
| 429 | CO₂C₂H₅ | OCH₃ | |

TABLE 34

General formula

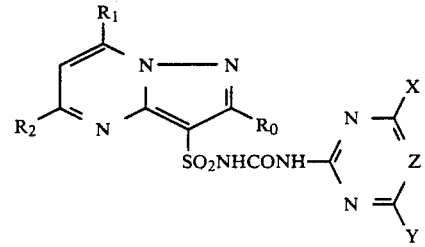

| Compound No. | R₀ | R₁ | R₂ | X | Y | Z | mp. (°C.) |
|---|---|---|---|---|---|---|---|
| 430 | H | H | H | CH₃ | CH₃ | CH | 190~194 |
| 431 | H | H | H | OCH₃ | OCH₃ | CH | 202~205 |
| 432 | H | H | H | CH₃ | OCH₃ | N | 187~188 |
| 433 | H | H | CH₃ | CH₃ | CH₃ | CH | 205~212 |
| 434 | H | H | CH₃ | OCH₃ | OCH₃ | CH | 183~186 |
| 435 | H | CH₃ | CH₃ | CH₃ | CH₃ | CH | 197~200 |
| 436 | H | CH₃ | CH₃ | OCH₃ | OCH₃ | CH | 172~176 |
| 437 | H | CH₃ | CH₃ | Cl | OCH₃ | CH | 170~172 |
| 438 | H | CH₃ | CF₃ | CH₃ | CH₃ | CH | 215~217 |
| 439 | H | CH₃ | CF₃ | CH₃ | OCH₃ | CH | 204~206 |
| 440 | H | CH₃ | CF₃ | OCH₃ | OCH₃ | CH | 187~189 |
| 441 | CH₃ | H | H | CH₃ | CH₃ | CH | |
| 442 | CH₃ | H | H | OCH₃ | OCH₃ | CH | 190~200 |
| 443 | CH₃ | H | H | Cl | OCH₃ | CH | |
| 444 | CH₃ | CH₃ | CH₃ | CH₃ | OCH₃ | CH | |
| 445 | CH₃ | CH₃ | CH₃ | Cl | OCH₃ | CH | |
| 446 | CH₃ | CH₃ | CH₃ | OCH₃ | OCH₃ | CH | 213~215 |
| 447 | Cl | H | H | CH₃ | OCH₃ | CH | |
| 448 | Cl | H | H | OCH₃ | OCH₃ | CH | |
| 449 | Cl | CH₃ | CH₃ | CH₃ | CH₃ | CH | 203~206 |
| 450 | Cl | CH₃ | CH₃ | OCH₃ | OCH₃ | CH | 191~194 |
| 451 | Cl | CH₃ | CH₃ | CH₃ | OCH₃ | N | 235~237 |
| 452 | —OSO₂—C₆H₄—CH₃ | CH₃ | CH₃ | OCH₃ | OCH₃ | CH | 161~165 |
| 453 | OCH₃ | CH₃ | CH₃ | OCH₃ | OCH₃ | CH | |
| 454 | SCH₃ | H | H | OCH₃ | OCH₃ | CH | |
| 455 | SCH₃ | CH₃ | CH₃ | CH₃ | OCH₃ | CH | 215~218 |
| 456 | SCH₃ | CH₃ | CH₃ | OCH₃ | OCH₃ | CH | 228~230 |
| 457 | SC₂H₅ | H | H | OCH₃ | OCH₃ | CH | |
| 458 | SC₂H₅ | CH₃ | CH₃ | CH₃ | OCH₃ | CH | 179~182 |
| 459 | SC₂H₅ | CH₃ | CH₃ | OCH₃ | OCH₃ | CH | 176~179 |
| 460 | SC₃H₇-n | H | H | OCH₃ | OCH₃ | CH | |
| 461 | SC₃H₇-n | CH₃ | CH₃ | CH₃ | CH₃ | CH | 170 |
| 462 | SC₃H₇-n | CH₃ | CH₃ | CH₃ | OCH₃ | CH | 173~174 |
| 463 | SC₄H₉-n | CH₃ | CH₃ | CH₃ | OCH₃ | CH | 155 |
| 464 | SC₄H₉-n | CH₃ | CH₃ | OCH₃ | OCH₃ | CH | 170 |
| 465 | SCH₂CH=CH₂ | CH₃ | CH₃ | OCH₃ | OCH₃ | CH | 173~175 |
| 466 | SO₂CH₃ | H | H | OCH₃ | OCH₃ | CH | |
| 467 | SO₂CH₃ | CH₃ | CH₃ | CH₃ | OCH₃ | CH | 280~283 |
| 468 | SO₂CH₃ | CH₃ | CH₃ | OCH₃ | OCH₃ | CH | 278~281 |
| 469 | SO₂C₂H₅ | H | H | OCH₃ | OCH₃ | CH | |
| 470 | SO₂C₂H₅ | CH₃ | CH₃ | CH₃ | OCH₃ | CH | 250~252 |
| 471 | SO₂C₂H₅ | CH₃ | CH₃ | OCH₃ | OCH₃ | CH | 248~250 |
| 472 | SO₂C₃H₇-n | H | H | OCH₃ | OCH₃ | CH | |
| 473 | SO₂C₃H₇-n | CH₃ | CH₃ | CH₃ | OCH₃ | CH | 176 |
| 474 | SO₂C₃H₇-n | CH₃ | CH₃ | OCH₃ | OCH₃ | CH | 206 |

TABLE 34-continued

General formula

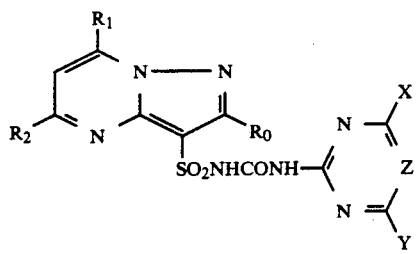

| Compound No. | R₀ | R₁ | R₂ | X | Y | Z | mp. (°C.) |
|---|---|---|---|---|---|---|---|
| 475 | SO₂C₄H₉-n | CH₃ | CH₃ | OCH₃ | OCH₃ | CH | |
| 476 | SO₂—CH₂CH=CH₂ | CH₃ | CH₃ | OCH₃ | OCH₃ | CH | 184~185 |
| 477 | CO₂CH₃ | H | H | OCH₃ | OCH₃ | CH | |
| 478 | CO₂CH₃ | CH₃ | CH₃ | OCH₃ | OCH₃ | CH | |
| 479 | CO₂C₂H₅ | H | H | OCH₃ | OCH₃ | CH | |
| 480 | CO₂C₂H₅ | CH₃ | CH₃ | OCH₃ | OCH₃ | CH | |

TABLE 35

General formula

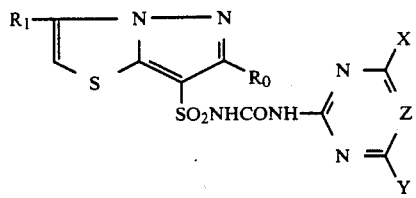

| Compound No. | R₀ | R₁ | X | Y | Z | mp. (°C.) |
|---|---|---|---|---|---|---|
| 481 | H | H | OCH₃ | OCH₃ | CH | |
| 482 | H | CH₃ | CH₃ | CH₃ | CH | 183~184 |
| 483 | H | CH₃ | OCH₃ | OCH₃ | CH | 202~204 |
| 494 | CH₃ | H | OCH₃ | OCH₃ | CH | |
| 485 | CH₃ | CH₃ | CH₃ | CH₃ | CH | 215~217 |
| 486 | CH₃ | CH₃ | OCH₃ | OCH₃ | CH | 203~205 |
| 487 | CH₃ | CH₃ | OCH₃ | OCH₃ | CH | 181~183 |
| 488 | CH₃ | CH₃ | CH₃ | OCH₃ | N | 214~215 |
| 489 | CO₂C₂H₅ | H | OCH₃ | OCH₃ | CH | |
| 490 | CO₂C₂H₅ | CH₃ | OCH₃ | OCH₃ | CH | 112~113 |
| 491 | CO₂C₂H₅ | CH₃ | CH₃ | OCH₃ | N | 200~201 |
| 492 | CONH₂ | H | OCH₃ | OCH₃ | CH | |
| 493 | CONH₂ | CH₃ | OCH₃ | OCH₃ | CH | 204~205 |
| 494 | CON(CH₃)₂ | H | OCH₃ | OCH₃ | CH | |
| 495 | CON(CH₃)₂ | CH₃ | OCH₃ | OCH₃ | CH | |
| 496 | Cl | H | OCH₃ | OCH₃ | CH | |
| 497 | Cl | CH₃ | OCH₃ | OCH₃ | CH | |
| 498 | SCH₃ | H | OCH₃ | OCH₃ | CH | |
| 499 | SCH₃ | CH₃ | OCH₃ | OCH₃ | CH | |
| 500 | SC₂H₅ | H | OCH₃ | OCH₃ | CH | |
| 501 | SC₂H₅ | CH₃ | OCH₃ | OCH₃ | CH | |

TABLE 36

General formula

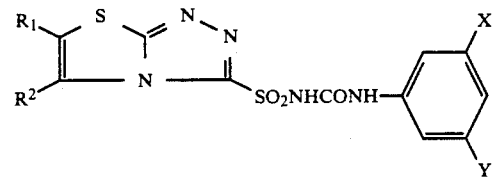

| Compound No. | R₁ | R₂ | X | Y | mp. (°C.) |
|---|---|---|---|---|---|
| 502 | H | H | OCH₃ | OCH₃ | |
| 503 | H | H | OCH₃ | OCH₃ | |
| 504 | CH₃ | CH₃ | CH₃ | CH₃ | 176~178 |
| 505 | CH₃ | CH₃ | OCH₃ | OCH₃ | |
| 506 | H | CO₂C₂H₅ | OCH₃ | OCH₃ | |

TABLE 37

General formula

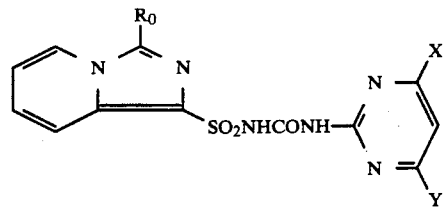

| Compound No. | R₀ | X | Y | mp. (°C.) |
|---|---|---|---|---|
| 507 | H | OCH₃ | OCH₃ | 184~187 |
| 508 | CH₃ | OCH₃ | OCH₃ | 225 (decomp.) |
| 509 | Cl | OCH₃ | OCH₃ | 180-183 |
| 510 | SCH₃ | OCH₃ | OCH₃ | 184~187 |
| 511 | SO₂CH₃ | OCH₃ | OCH₃ | 202~205 |
| 512 | CO₂C₂H₅ | OCH₃ | OCH₃ | |

TABLE 38

General formula

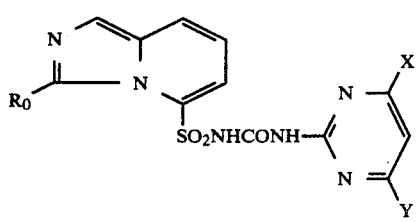

| Compound No. | $R_0$ | X | Y | mp. (°C.) |
|---|---|---|---|---|
| 513 | H | $OCH_3$ | $OCH_3$ | 175~178 |
| 514 | $CH_3$ | $OCH_3$ | $OCH_3$ | 175~177 |
| 515 | Cl | $OCH_3$ | $OCH_3$ | |
| 516 | $SCH_3$ | $OCH_3$ | $OCH_3$ | 181 (decomp.) |
| 517 | $SO_2CH_3$ | $OCH_3$ | $OCH_3$ | |
| 518 | $CO_2C_2H_5$ | $OCH_3$ | | |

TABLE 39

General formula

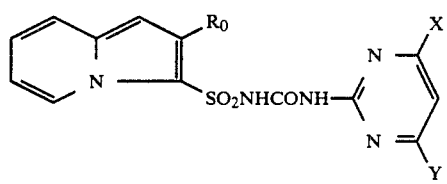

| Compound No. | $R_0$ | X | Y | mp. (°C.) |
|---|---|---|---|---|
| 519 | $CH_3$ | $CH_3$ | $OCH_3$ | 178~180 |
| 520 | Cl | $OCH_3$ | $OCH_3$ | 184~186 |
| 521 | $CO_2C_2H_5$ | $OCH_3$ | $OCH_3$ | 173~175 |

TABLE 40

General formula

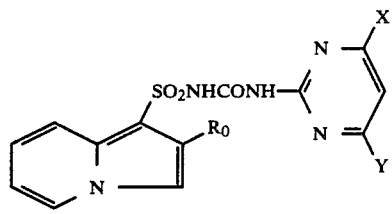

| Compound No. | $R_0$ | X | Y | mp. (°C.) |
|---|---|---|---|---|
| 522 | $CH_3$ | $CH_3$ | $OCH_3$ | 188~189 |
| 523 | Cl | $OCH_3$ | $OCH_3$ | 179~181 |
| 524 | $CO_2C_2H_5$ | $OCH_3$ | $OCH_3$ | |

TABLE 41

General formula

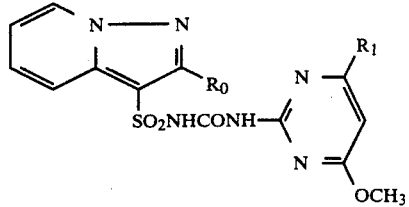

| Compound No. | $R_0$ | $R_1$ | mp. (°C.) |
|---|---|---|---|
| 525 | H | $OCH_3$ | |
| 526 | $CH_3$ | Cl | |
| 527 | $CH_3$ | $OCH_3$ | 190~194 |
| 528 | Cl | $CH_3$ | |
| 529 | Cl | Cl | |
| 530 | Cl | $OCH_3$ | |
| 531 | $CO_2C_2H_5$ | $CH_3$ | |
| 532 | $CO_2C_2H_5$ | Cl | |
| 533 | $CO_2C_2H_5$ | $OCH_3$ | |

TABLE 42

General formula

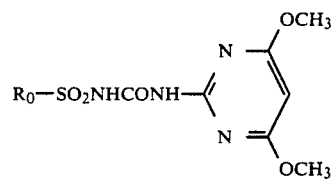

| Compound No. | $R_0$ | mp (°C.) |
|---|---|---|
| 534 | 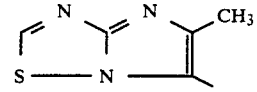 | |
| 535 | 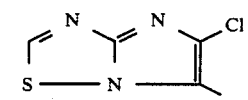 | |
| 536 | 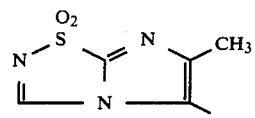 | |
| 537 | 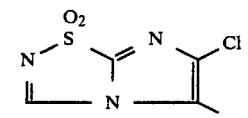 | |
| 538 | 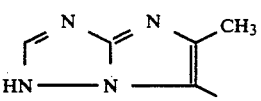 | |
| 539 | 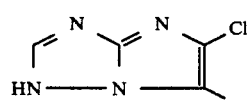 | |
| 540 | 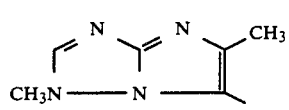 | |

TABLE 42-continued

General formula $$R_0\text{—}SO_2NHCONH\text{—}\underset{N}{\overset{N}{\diagdown}}\hspace{-0.5em}\underset{\phantom{N}}{\underset{OCH_3}{\bigg\langle}}\hspace{-1em}\underset{OCH_3}{\phantom{N}}$$

| Compound No. | $R_0$ | mp (°C.) |
|---|---|---|
| 541 | 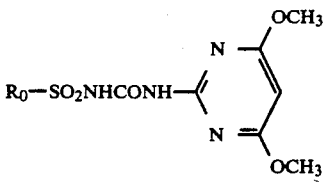 | |
| 542 | 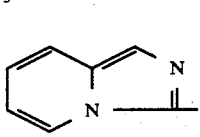 | 175~179 |

TABLE 43

General formula $$\underset{R_1}{\diagup}\hspace{-0.5em}\underset{N}{\overset{N}{\diagdown}}\hspace{-0.5em}\underset{SO_2NH}{\overset{R_0}{=}}\hspace{-0.5em}\underset{N}{\overset{N}{\diagdown}}\hspace{-0.5em}\underset{OCH_3}{\overset{OCH_3}{\bigg\langle}}$$

| Compound No. | $R_0$ | $R_1$ | mp (°C.) |
|---|---|---|---|
| 543 | Cl | $C_2H_5O$ | 168~169 |
| 544 | Cl | $n\text{-}C_3H_7O$ | 194~196 |
| 545 | Cl | $i\text{-}C_3H_7O$ | |
| 546 | Cl | $CH_2=CHCH_2O$ | |
| 547 | Cl | $n\text{-}C_3H_7S$ | 170~173 |
| 548 | Cl | $i\text{-}C_3H_7S$ | |
| 549 | Cl | $CH_2=CHCH_2O$ | |
| 550 | F | $CH_3O$ | |
| 551 | F | $CH_3S$ | |
| 552 | F | $(CH_3)_2N$ | |
| 553 | Br | $CH_3O$ | |
| 554 | Br | $CH_3S$ | |
| 555 | Br | $(CH_3)_2N$ | |

FORMULATION EXAMPLE 1

Emulsifiable concentrates, containing:

| Compound No. 98 | 2% |
|---|---|
| xylene | 75% |
| dimethylformamide | 18% |
| polyethylene glycol ether (Nonipol 85 ®) | 5% |

(to be used suitably with dilution in water)

FORMULATION EXAMPLE 2

Wettable powders, as prepared by blending and grinding the following components:

| Compound No. 350 | 5% |
|---|---|
| sodium ligninsulfonate | 5% |
| polyoxyethylene glycol ether (Nonipol 85 ®) | 5% |
| clay | 80% |
| white carbon | 5% |

(to be used suitably with dilution in water)

FORMULATION EXAMPLE 3

Granules, as prepared by adding water to the following mixture, blending and granulating:

| Compound No. 3 | 0.25% |
|---|---|
| soidum ligninsulfonate | 2.00% |
| bentonite | 57.75% |
| talc | 40.00% |

FORMULATION EXAMPLE 4

Granules, as prepared by adding water to the following mixture, blending and granulating:

| Compound No. 1 | 0.25% |
|---|---|
| sodium ligninsulfonate | 5.00% |
| bentonite | 94.75% |

FORMULATION EXAMPLE 5

Granules, as prepared by adding water to the following mixture, blending and granulating:

| Compound No. 2 | 0.5% |
|---|---|
| sodium ligninsulfonate | 6.0% |
| bentonite | 93.5% |

FORMULATION EXAMPLE 6

Granules, as prepared by adding water to the following mixture, blending and granulating:

| Compound No. 1 | 0.25% |
|---|---|
| sodium ligninsulfonate | 5.00% |
| bentonite | 30.00% |
| clay | 64.75% |

TEST EXAMPLE 1 (Test for selectivity on rice)

Paddy soil was put in a square-shaped plastic pot having a surface area of 150 cm². After introducing water and scratching the bed, seeds of Echinochloa oryzicola, Cyperus difformis, Scirous juncoides, Lindernia procumberns and Rotala indica were sowed, and further tubers of Sagittavia pygmaea were planted. Cultivation was effected for a prescribed term, while filling the pot with water up to 3 cm height over the bed surface. On the other hand, paddy soil was put in a Wagner pot having a surface area of 1/10000 are. After introducing water and scratching the bed, 2 nursery rice-plants were transplanted to the bed and the pot was filled with water up to 3 cm height over the bed surface. One week after the transplantation of the rice-plants, when monocotyl weeds grew up to the mono-leaf period, a dilute solution containing a compound (I) was applied into the pot, so that 1 g of the compound (I) was applied per 1 are of the bed surface. The dilute solution was prepared by dissolving 1 g of the compound (I) in 300 ml of acetone containing 2%(W/V) of a surface active agent Tween 20 ® and diluting with water up to 40 l in total.

Three weeks after the application, herbicidal effect against various weeds and harmful effect on the transplanted rice-plant were evaluated according to the following standards:

| Index number | Effect | Control ratio (Herbicidal ratio) % |
|---|---|---|
| 0 | non | 0 |
| 1 | slight | 0.1 to 50 |
| 2 | small | 50.1 to 75 |
| 3 | medium | 75.1 to 87.5 |
| 4 | large | 87.6 to 99.9 |
| 5 | extremely large | 100 |

Harmful effect on rice-plant was shown by the following index numbers (also in the following Test Examples):

| Index number | Harmful Effect | Damage ratio % |
|---|---|---|
| 0 | non | 0 |
| 1 | slight | 0.1 to 12.5 |
| 2 | small | 12.6 to 25 |
| 3 | medium | 25.1 to 50.0 |
| 4 | large | 50.1 to 99.9 |
| 5 | extremely large | 100 |

The results obtained are shown in Table 44.

TABLE 44

| Compound No. | Harmful Effect rice | Herbicidal Effect A | B | C | D | E | F |
|---|---|---|---|---|---|---|---|
| 1 | 0 | 4 | 5 | 4 | 4 | 4 | 4 |
| 2 | 0 | 4 | 4 | 3 | 4 | 4 | 4 |
| 3 | 0 | 4 | 4 | 3 | 3 | 4 | 4 |
| 104 | 0 | 3 | 4 | 3 | 3 | 4 | 3 |
| 179 | 1 | 3 | 4 | 4 | 3 | 3 | 4 |
| 201 | 0 | 3 | 4 | 4 | 4 | 4 | 4 |
| 207 | 0 | 4 | 4 | 4 | 4 | 4 | 4 |
| 350 | 0 | 3 | 3 | 4 | 3 | 4 | 4 |
| 471 | 1 | 4 | 5 | 4 | 4 | 4 | 4 |

A: *Echinochloa oryzicola*
B: *Cyperus difformis*
C: *Lindernia procumbens*
D: *Rotala indica*
E: *Scirpus juncoides*
F: *Sagittavia pygmaea*

TEST EXAMPLE 2 (Test for selectivity on rice)

Paddy soil was put in a Wagner pot having a surface area of 1/10000 are, and seeds of *Cyperus difformis, Monochoria vaginalis, Lindernia procumbens* and *Rotala indica* were sowed. After cultivation for one week, two nursery rice-plants were transplanted to the bed. In another pot were sowed seeds of *Echinochloa oryzicola* and *Scirupus juncoides*, and in still another pot was scattered paddy soil containing biennal stems of *Eleocharis acicularis* and, after planting budding tubers of *Sagittaria pygmaea*, were planted budding tubers of *Cyperus serotinus* with the buds bared on the surface of the soil. Every pot was filled with water up to 3 cm height over the bed surface. Then, one week after the transplantation of rice-plants (the mono-leaf period of *Echinochloa oryzicola*), a prescribed amount of granules containing a compound (I), which were prepared in the same manner as Preparation Example 3, or of Simetryn for contrast, was applied to each pot.

Three weeks after the application, herbicidal effect and harmful effect were evaluated according to the same standards as Test Example 1. The results obtained are shown in Table 45.

TABLE 45

| Compound No. | Application rate (g/are) | Harmful Effect rice | Herbicidal Effect A | B | C | D | E | F | G | H | I |
|---|---|---|---|---|---|---|---|---|---|---|---|
| 1 | 0.5 | 0 | 4 | 4 | 4 | 3 | 3 | 4 | 4 | 4 | 4 |
|   | 1.0 | 0 | 4 | 4 | 5 | 4 | 4 | 4 | 4 | 4 | 4 |
|   | 2.0 | 0 | 4 | 5 | 5 | 5 | 4 | 4 | 4 | 4 | 4 |
| 2 | 0.5 | 0 | 4 | 4 | 3 | 3 | 3 | 4 | 4 | 4 | 4 |
|   | 1.0 | 0 | 4 | 4 | 4 | 4 | 4 | 4 | 4 | 4 | 4 |
|   | 2.0 | 1 | 4 | 4 | 4 | 4 | 4 | 4 | 4 | 4 | 4 |
| 98 | 0.5 | 0 | 3 | 4 | 4 | 3 | 2 | 3 | 4 | 4 | 3 |
|   | 1.0 | 0 | 3 | 4 | 5 | 3 | 3 | 3 | 4 | 4 | 3 |
|   | 2.0 | 0 | 4 | 4 | 5 | 3 | 4 | 4 | 4 | 4 | 4 |
| 350 | 0.5 | 0 | 3 | 4 | 4 | 4 | 4 | 4 | 4 | 4 | 4 |
|   | 1.0 | 0 | 4 | 4 | 4 | 4 | 4 | 4 | 4 | 4 | 4 |
|   | 2.0 | 1 | 4 | 4 | 5 | 4 | 5 | 4 | 4 | 4 | 4 |
| Simetryn (for Contrast) | 2.5 | 1 | 1 | 3 | 4 | 4 | 4 | 1 | 1 | 1 | 1 |
|   | 5.0 | 2 | 4 | 4 | 5 | 5 | 5 | 3 | 1 | 2 | 1 |
|   | 10.0 | 3 | 5 | 5 | 5 | 5 | 5 | 4 | 1 | 3 | 2 |

A: *Echinochloa oryzicola*
B: *Cyperus difformis*
C: *Monochoria vaginalis*
D: *Lindernia procumbens*
E: *Rotala indica*
F: *Scirpus juncoides*
G: *Cyperus serotinus*
H: *Eleocharis acicularis*
I: *Sagittaria pygmaea*

What we claim is:
1. A compound of the formula

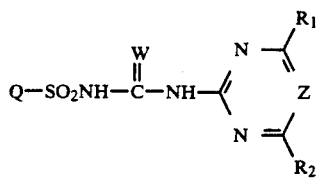 (I)

wherein Q is a condensed heterocyclic group which is formed by removing one hydrogen atom bonded to a heterocyclic ring-constituting carbon atom at a position other than a bridgehead from a condensed heterocyclic ring selected from the group consisting of

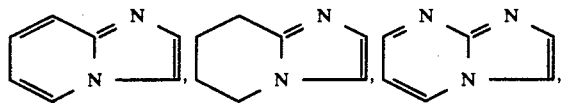

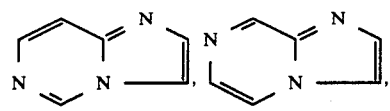

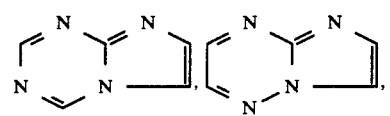

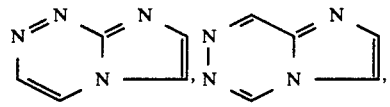

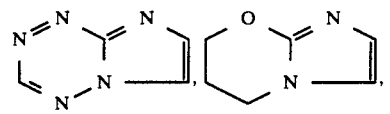

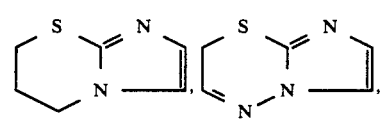

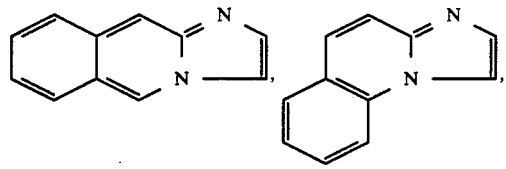

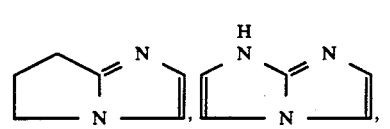

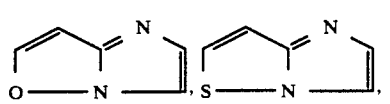

-continued

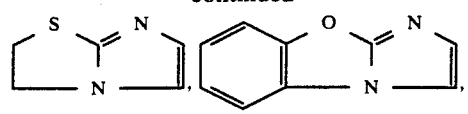

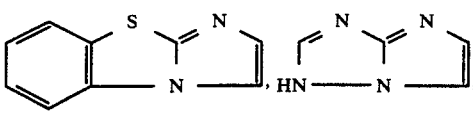

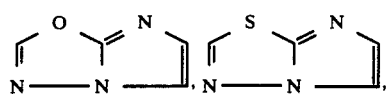

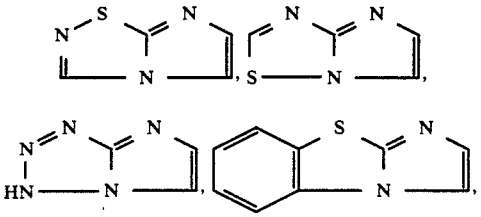

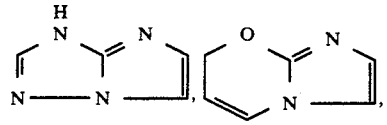

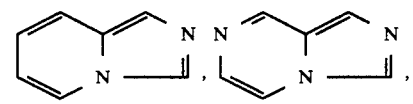

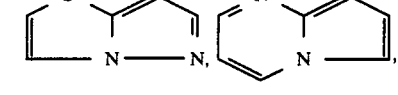

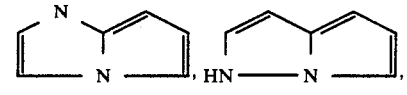

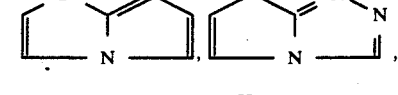

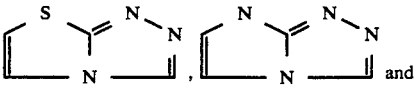 and

which sulfur atom may be in mono- or di-oxidized form, wherein bonding of Q to SO$_2$ in formula (I) always occurs through a heterocyclic ring of Q, which condensed heterocyclic group is unsubstituted or substituted by the same or different one to three substituents selected from the group consisting of (1) hydroxy, (2) amino, (3) cyano, (4) sulfamoyl, (5) sulfamoyloxy, (6) mercapto, (7) nitro, (8) a halogen, (9) a straight chain, branched chain or cyclic alkyl group containing 1 to 6 carbon atoms, which is unsubstituted or substituted by one to three members selected from the group consisting of (a) a straight chain or branched chain alkylthio group containing 1 to 4 carbon atoms, (b) a halogen, (c) a straight chain or branched chain alkoxy group containing 1 to 6 carbon atoms, (d) nitro, (e) an alkoxycarbonyl group containing 1 to 6 carbon atoms in the alkoxy moiety and (f) a mono- or di-($C_{1-6}$ alkyl) amino group, (10) a straight chain, branched chain or cyclic alkenyl group containing 3 to 6 carbon atoms, which is unsubstituted or substituted by one to three members selected from the group consisting of (a) a straight chain or branched chain alkylthio group containing 1 to 4 carbon atoms, (b) a halogen, (c) a straight chain or branched chain alkoxy group containing 1 to 6 carbon atoms, (d) nitro, (e) an alkoxycarbonyl group containing 1 to 6 carbon atoms in the alkoxy moiety and (f) a mono or di-($C_{1-6}$ alkyl) amino group, (11) an alkynyl group containing 3 to 6 carbon atoms, which is unsubstituted or substituted by one to three members selected from the group consisting of (a) a straight chain or branched chain alkylthio group containing 1 to 4 carbon atoms, (b) a halogen, (c) a straight chain or branched chain alkoxy group containing 1 to 6 carbon atoms, (d) nitro, (e) an alkoxycarbonyl group containing 1 to 6 carbon atoms in the alkoxy moiety and (f) a mono- or di-($C_{1-6}$ alkyl) amino group, (12) an aryl group containing 6 to 14 carbon atoms, which is unsubstituted or substituted by one to three members selected from the group consisting of (a) a straight chain, branched chain or cyclic alkyl group containing 1 to 6 carbon atoms, (b) a straight chain, branched chain or cyclic alkenyl group containing 3 to 6 carbon atoms, (c) an alkynyl group containing 3 to 6 carbon atoms, (d) a straight chain or branched chain alkoxy group containing 1 to 6 carbon atoms, (e) an acyl group derived from an organic carboxylic acid, (f) an acyloxy group in which the acyl group is as defined just above in (e), (g) nitro, (h) cyano, (i) a halogen, (j) an acylamino in which acyl is as defined above in (e), and (k) a straight chain or branched chain alkylthio group containing 1 to 4 carbon atoms, (13) an aralkyl group containing 7 to 19 carbon atoms, (14) a 5 or 6 membered heterocyclic group selected from the group consisting of 2- or 3-pyrrolyl, 3-, 4- or 5-pyrazolyl, 2-, 4- or 5-imidazolyl, 1,2,3-triazol-4-yl, 1,2,4-triazol-3-yl, 1H- or 2H-tetrazol-5-yl, 2- or 3-furyl, 2- or 3-thienyl, 2-,4- or 5-oxazolyl, 3-, 4- or 5-isoxazolyl, 1,2,3-oxadiazol-4- or 5-yl, 1,2,4-oxadiazol-3 or 5-yl, 1,2,5-oxadiazol-3 or 4-yl, 1,3,4-oxadiazol-2- or 5-yl, 2-, 4- or 5-thiazolyl, 3-, 4- or 5-isothiazolyl, 1,2,3-thiadiazol-4 or 5-yl, 1,2,4-thiadiazol-3 or 5-yl, 1,2,5-thiadiazol-3 or 4-yl, 1,3,4-thiazol-2 or 5-yl, 2- or 3-pyrrolidinyl, 2-,3- or 4-pyridyl, 3- or 4-pyridazinyl, 2-, 4- or 5-pyrimidinyl, pyrazinyl, 2-, 3- or 4-piperidinyl, piperazinyl, 3H-indol-2 or 3-yl, 2-, 3- or 4-pyranyl, 2-, 3-or 4-thiopyranyl, benzopyranyl, quinolyl, pyrido[2,3-d]pyrimidinyl, 1,5-, 1,6-, 1,7- 1,8-, 2,6- or 2,7-naphthyridinyl, thieno[2,3-d]pyridyl, pyrazinoquinolyl and chromenyl, in which the nitrogen and sulfur atoms may be oxidized, which is unsubstituted or substituted by one to three members selected from the group consisting of the substituents (9) to (13) as defined above, an acyl group derived from an organic carboxylic acid and a halogen, (15) an acyl group derived from an organic carboxylic acid, (16) a group of the formula —T— $Q_0$ in which $Q_0$ is any one of the substituents (9) to (15) as defined above, and T is O, S—(O)n or S—S, n being 0, 1 or 2, (17) a group of the formula

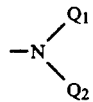

in which $Q_1$ is hydrogen or any one of the substituents (9) to (13) and (15) as defined above and $Q_2$ is any one of the substituents (9) to (13) and (15) as defined above, (18) a group of the formula

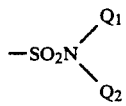

in which $Q_1$ and $Q_2$ are as defined above, (19) a carbamoyl, carbamoyloxy, ureido or thiocarbamoyl group which is unsubstituted or substituted by the same or different 1 or 2 substituents of (9) to (15) as defined above, (20) carboxyl, (21) a group of the formula —O—$SO_2$—$Q_2$ in which $Q_2$ has the same meaning as defined above, and (22) sulfo, the acyl group derived from an organic carboxylic acid in the above items (12)(e), (14) and (15) being one selected from the group consisting of an alkanoyl group containing 1 to 7 carbon atoms, an arylcarbonyl group containing 6 to 14 carbon atoms, an alkoxycarbonyl group containing 1 to 6 carbon atoms, an aryloxycarbonyl group containing 6 to 14 carbon atoms, an aralkylcarbonyl group containing 7 to 19 carbon atoms, 2-,3- or 4-pyrrolylcarbonyl, 3-,4- or 5-pyrazolylcarbonyl, 2-,4- or 5-imidazolylcarbonyl, 1,2,3-triazol-4-ylcarbonyl, 1,2,4-triazol-3-ylcarbonyl, 1H- or 2H-tetrazol-5-ylcarbonyl, 2- or 3-furylcarbonyl, 2- or 3-thienylcarbonyl, 2-,4-or 5-oxazolylcarbonyl, 3-,4- or 5-isoxazolylcarbonyl, 1,2,3-oxadiazol-4 or 5-ylcarbonyl, 1,2,4-oxadiazol-3 or 5-ylcarbonyl, 1,2,5-oxadiazolyl-3 or 4-carbonyl, 1,2,4-oxadiazol-2 or 5-ylcarbonyl, 2-,4- or 5-thiazolylcarbonyl, 3-,4- or 5-isothiazolylcarbonyl, 1,2,3-thiadiazol-4 or 5-ylcarbonyl, 1,2,4-thiadiazol-3 or 5-ylcarbonyl, 1,2,5-thiadiazol-3 or 4-ylcarbonyl, 1,3,4-thiadiazol-2 or 5-ylcarbonyl, 2- or 3-pyrrolidinylcarbonyl, 2-,3- or 4-pyridylcarbonyl, 2-,3- or 4-pyridyl-N-oxide-carbonyl, 3- or 4-pyridazinylcarbonyl, 3- or 4-pyridazinyl-N-oxide-carbonyl, 2-,4- or 5-pyrimidinylcabonyl, 2-,4- or 5-pyrimidinyl-N-oxide-carbonyl, pyrazinylcarbonyl, 2-,3- or 4-piperidinylcarbonyl, piperazinylcarbonyl, 3H-indol-2 or 3-ylcarbonyl, 2-,3-or 4-pyranylcarbonyl, 2-,3- or 4-thiopyranylcarbonyl, 3-,4-,5-,6-,7- or 8-quinolylcarbonyl, pyrido[2,3-d]pyrimidinylcarbonyl, 1,5-, 1,6-, 1,7-, 1,8-, 2,6- or 2,7-naphthyridinylcarbonyl, thieno[2,3-d]pyridylcarbonyl, pyrazinoquinolylcarbonyl, chromenylcarbonyl, 2-pyrrolylacetyl, 3-imidazolylacetyl and 5-isoxazolylacetyl, W is O or S, $R_1$ and $R_2$ each are a straight chain, branched chain or cyclic alkyl group containing 1 to 6 carbon atoms, a straight chain or branched chain alkoxy group containing 1 to 6 carbon atoms, or a halogen, and Z is CH,
or a salt thereof.

2. A compound of claim 1 in which Q is

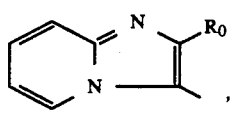

wherein $R_0$ is hydrogen, a $C_{1-4}$ alkyl group which may be substituted by halogen, a $C_{1-4}$ alkylthio, $C_{1-4}$ alkylsulfonyl or $C_{1-4}$ alkoxycarbonyl group or a halogen.

3. A compound of claim 1 in which Q is a group which is formed by removing one hydrogen atom bonded to a heterocyclic ring-constituting carbon atom at a position other than a bridgehead from a condensed heterocyclic ring selected from the group consisting of

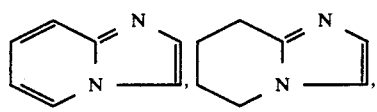
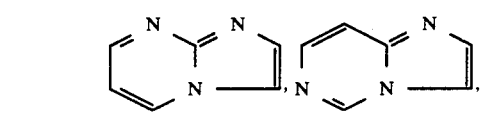
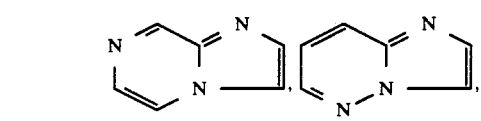
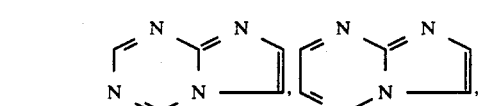
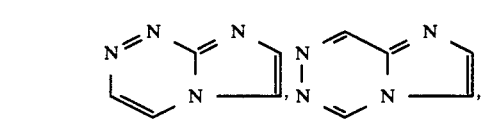
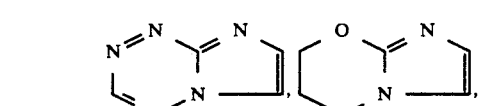
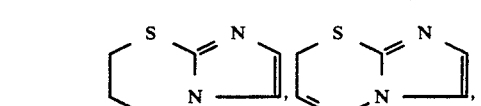
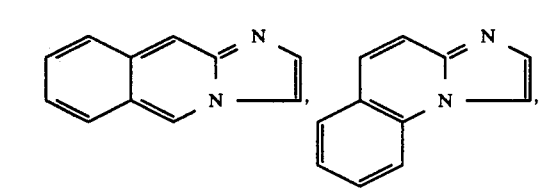
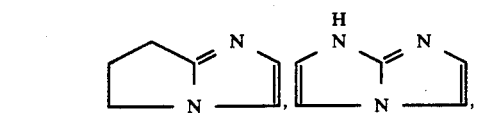

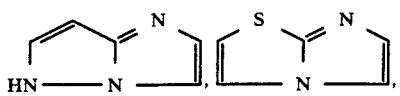
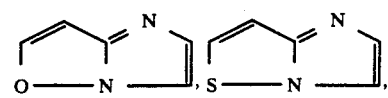
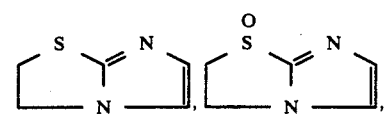
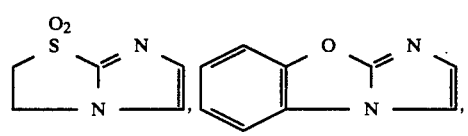
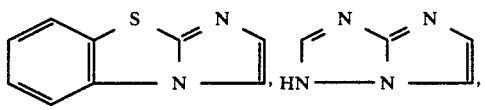
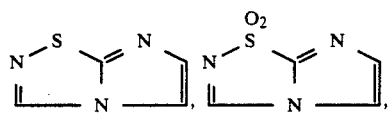
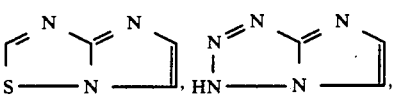
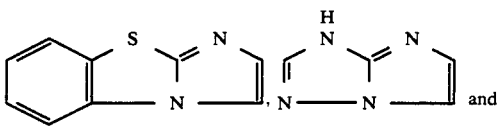 and

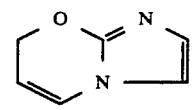

which is unsubstituted or substituted by any one of the substituents (1)–(22) as defined in claim 33, and wherein bonding of Q to $SO_2$ in formula (I) always occurs through a heterocyclic ring of Q.

4. A compound of claim 1 in which the condensed heterocyclic ring of Q is
imidazo[1,2-a]pyridine

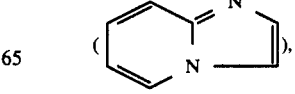

imidazo[2,1-b]thiazole

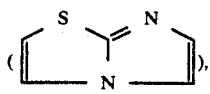

imidazo[1,2-a]pyrimidine

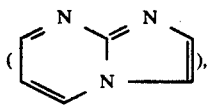

imidazo[1,2-c]pyrimidine

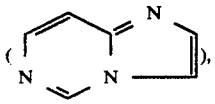

imidazo[2,1-b](1,3,4)thiadiazole

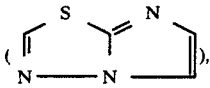

2,3-dihydroimidazo[2,1-b]thiazole

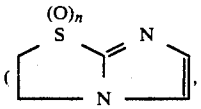

(or its mono- or di-oxide; n is 0, 1 or 2)
pyrazolo[5,1-b]thiazole

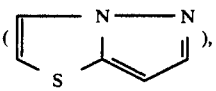

imidazo[1,5-a]pyridine

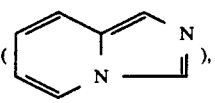

(1,2,4)triazolo[3,4-b]thiazole

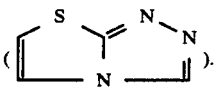

5. A compound of claim 1 in which Q is

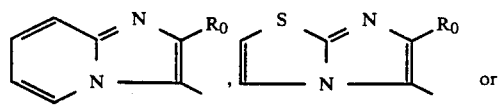

-continued

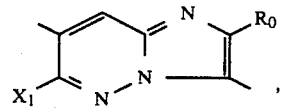

wherein $R_0$ is hydrogen, a lower alkyl group which may be substituted by a halogen, a lower alkylthio group, a lower alkylsulfonyl group, a lower alkoxycarbonyl group or a halogen, and $X_1$ l is a halogen, a lower alkylamino group or a di-(lower alkyl)amino group.

6. A compound of claim 1 which is N-(2-chloroimidazo[1,2-a]pyridin-3-ylsulfonyl)-N'-(4,6-dimethoxy-2-pyrimidinyl)urea.

7. A compound of claim 1 is N-(2-chloroimidazo[1,2-a]pyrimidin-3-ylsulfonyl)-N'-(4-methoxy-6-methyl-2-pyrimidinyl) urea.

8. A compound of claim 1 which is N-(2-bromoimidazo[1,2-a]pyridin-3-ylsulfonyl)-N'-(4,6-dimethoxy-2-pyrimidinyl)urea.

9. A compound of claim 1 in which is N-(6-chloroimidazo[2,1-b]thiazol-5-ylsulfonyl)-N'-(4,6-dimethoxy-2-pyrimidinyl) urea.

10. A method of killing weeds in a paddy field which comprises applying a herbicidally effective amount of a compound salt of claim 1 to the paddy field.

11. A herbicidal composition comprising as an active ingredient an effective amount of a compound or salt of claim 1, and a carrier therefor suitable for herbicidal use of the composition.

12. A herbicidal composition of claim 11 in which the compound of the formula (I) is N-(2-chloroimidazo[1,2-a]pyridin-3-ylsulfonyl)-N'-(4,6-dimethoxy-2-pyrimidinyl)urea, N-(2-chloroimidazo[1,2-a]pyrimidin-3-ylsulfonyl)-N'-(4-methoxy-6-methyl-2-pyridimidinyl)urea, N-(2-bromoimidazo[1,2-a]pyridin-3-ylsulfonyl)-N'-(4,6-dimethoxy-2-pyrimidinyl)urea, or N-(6-chloroimidazo[2,1-b]thiazol-5-ylsulfonyl)-N'-(4,6-dimethoxy-2-pyrimidinyl)urea.

13. A compound of the formula

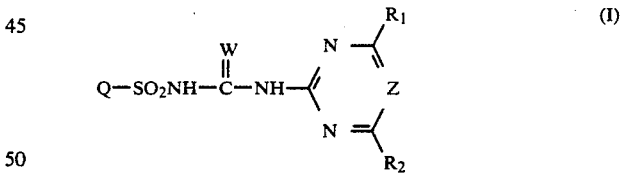

(I)

wherein Q is a condensed heterocyclic group which is formed by removing one hydrogen atom bonded to a heterocyclic ring-constituting carbon atom at a position other than a bridgehead from a condensed heterocyclic ring selected from the group consisting of

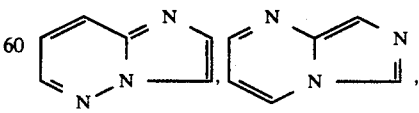

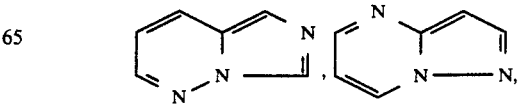

-continued

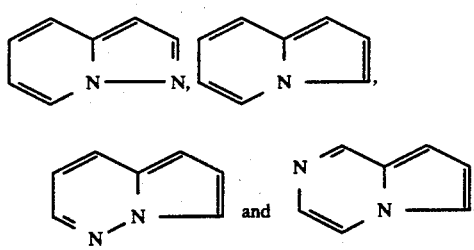

which sulfur atom may be in mono- or di-oxidized form, wherein bonding of Q to SO₂ in formula (I) always occurs through a heterocyclic ring of Q, which condensed heterocyclic group is unsubstituted or substituted by the same or different one to three substituents selected from the group consisting of (1) hydroxy, (2) amino, (3) cyano, (4) sulfamoyl, (5) sulfamoyloxy, (6) mercapto, (7) nitro, (8) a halogen, (9) a straight chain, branched chain or cyclic alkyl group containing 1 to 6 carbon atoms, which is unsubstituted or substituted by one to three members selected from the group consisting of (a) a straight chain or branched chain alkylthio group containing 1 to 4 carbon atoms, (b) a halogen, (c) a straight chain or branched chain alkoxy group containing 1 to 6 carbon atoms, (d) nitro, (e) an alkoxycarbonyl group containing 1 to 6 carbon atoms in the alkoxy moiety and (f) a mono- or di-($C_{1-6}$ alkyl) amino group, (10) a straight chain, branched chain or cyclic alkenyl group containing 3 to 6 carbon atoms, which is unsubstituted or substituted by one to three members selected from the group consisting of (a) a straight chain or branched chain alkylthio group containing 1 to 4 carbon atoms, (b) a halogen, (c) a straight chain or branched chain alkoxy group containing 1 to 6 carbon atoms, (d) nitro, (e) an alkoxycarbonyl group containing 1 to 6 carbon atoms in the alkoxy moiety and (f) a mono- or di-($C_{1-6}$ alkyl) amino group, (11) an alkynyl group containing 3 to 6 carbon atoms, which is unsubstituted or substituted by one to three members selected from the group consisting of (a) a straight chain or branched chain alkylthio group containing 1 to 4 carbon atoms, (b) a halogen, (c) a straight chain or branched chain alkoxy group containing 1 to 6 carbon atoms, (d) nitro, (e) an alkoxycarbonyl group containing 1 to 6 carbon atoms in the alkoxy moiety and (f) a mono- or di-($C_{1-6}$ alkyl) amino group, (12) an aryl group containing 6 to 14 carbon atoms, which is unsubstituted or substituted by one to three members selected from the group consisting of (a) a straight chain, branched chain or cyclic alkyl group containing 1 to 6 carbon atoms, (b) a straight chain, branched chain or cyclic alkenyl group containing 3 to 6 carbon atoms, (c) an alkynyl group containing 3 to 6 carbon atoms, (d) a straight chain or branched chain alkoxy group containing 1 to 6 carbon atoms, (e) an acyl group derived from an organic carboxylic acid, (f) an acyloxy group in which the acyl group is as defined just above in (e), (g) nitro, (h) cyano, (i) a halogen, (j) an acylamino in which acyl is as defined above in (e), and (k) a straight chain or branched chain alkylthio group containing 1 to 4 carbon atoms, (13) an aralkyl group containing 7 to 19 carbon atoms, (14) a 5 or 6 membered heterocyclic group selected from the group consisting of 2- or 3-pyrrolyl, 3-, 4- or 5-pyrazolyl, 2-, 4- or 5-imidazolyl, 1,2,3-triazol-4-yl, 1,2,4-triazol-3-yl, 1H- or 2H-tetrazol-5-yl, 2- or 3-furyl, 2- or 3-thienyl, 2-,4- or 5-oxazolyl, 3-, 4- or 5-isoxazolyl, 1,2,3-oxadiazol-4 or 5-yl, 1,2,4-oxadiazol-3 or 5-yl, 1,2,5- oxadiazol-3 or 4-yl, 1,3,4-oxadiazol-2- or 5-yl, 2-, 4- or 5-thiazolyl, 3-, 4- or 5-isothiazolyl, 1,2,3-thiadiazol-4 or 5-yl, 1,2,4-thiadiazol-3 or 5-yl, 1,2,5-thiadiazol-3 or 4-yl, 1,3,4-thiazol-2 or 5-yl, 2- or 3-pyrrolidinyl, 2-,3- or 4-pyridyl, 3- or 4-pyridazinyl, 2-, 4- or 5-pyrimidinyl, pyrazinyl, 2-, 3- or 4-piperidinyl, piperazinyl, 3H-indol-2 or 3-yl, 2-, 3- or 4-pyranyl, 2-, 3-or 4-thiopyranyl, benzopyranyl, quinolyl, pyrido[2,3-d]pyrimidinyl, 1,5-, 1,6-, 1,7-, 1,8-, 2,6- or 2,7-naphthyridinyl, thieno[2,3-d]pyridyl, pyrazinoquinolyl and chromenyl, in which the nitrogen and sulfur atoms may be oxidized, which is unsubstituted or substituted by one to three members selected from the group consisting of the substituents (9) to (13) as defined above, an acyl group derived from an organic carboxylic acid and a halogen, (15) an acyl group derived from an organic carboxylic acid, (16) a group of the formula —T—$Q_0$ in which $Q_0$ is any one of the substituents (9) to (15) as defined above, and T is O, S—(O)n or S—S, n being 0, 1 or 2, (17) a group of the formula

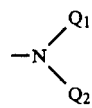

in which $Q_1$ is hydrogen or any one of the substituents (9) to (13) and (15) as defined above and $Q_2$ is any one of the substituents (9) to (13) and (15) as defined above, (18) a group of the formula

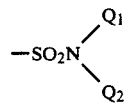

in which $Q_1$ and $Q_2$ are as defined above, (19) a carbamoyl, carbamoyloxy, ureido or thiocarbamoyl group which is unsubstituted or substituted by the same or different 1 or 2 substituents of (9) to (15) as defined above, (20) carboxyl, (21) a group of the formula —O—SO₂—$Q_2$ in which $Q_2$ has the same meaning as defined above, and (22) sulfo, the acyl group derived from an organic carboxylic acid in the above items (12)(e), (14) and (15) being one selected from the group consisting of an alkanoyl group containing 1 to 7 carbon atoms, an arylcarbonyl group containing 6 to 14 carbon atoms, an alkoxycarbonyl group containing 1 to 6 carbon atoms, an aryloxycarbonyl group containing 6 to 14 carbon atoms, an aralkylcarbonyl group containing 7 to 19 carbon atoms, 2-,3- or 4-pyrrolylcarbonyl, 3-,4- or 5-pyrazolylcarbonyl, 2-,4- or 5-imidazolylcarbonyl, 1,2,3-triazol-4-ylcarbonyl, 1,2,4-triazol-3-ylcarbonyl, 1H- or 2H-tetrazol-5-ylcarbonyl, 2- or 3-furylcarbonyl, 2- or 3-thienylcarbonyl, 2-,4-or 5-oxazolylcarbonyl, 3-,4- or 5-isoxazolylcarbonyl, 1,2,3-oxadiazol-4 or 5-ylcarbonyl, 1,2,4-oxadiazol-3- or 5-ylcarbonyl, 1,2,5-oxadiazolyl-3 or 4-carbonyl, 1,2,4-oxadiazol-2 or 5-ylcarbonyl, 2-,4- or 5-thiazolylcarbonyl, 3-,4- or 5-isothiazolylcarbonyl, 1,2,3-thiadiazol-4 or 5-ylcarbonl, 1,2,4-thiadiazol-3 or 5-ylcarbonyl, 1,2,5-thiadiazol-3 or 4-ylcarbonyl, 1,3,4-thiadiazol-2 or 5-ylcarbonyl, 2- or 3-pyrrolidinylcarbonyl, 2-,3- or 4-pyridylcarbonyl, 2-,3- or 4-pyridyl-N-oxide-carbonyl, 3- or 4-pyridazinylcarbonyl, 3- or 4-pyridazinyl-N-oxide-carbonyl, 2-,4- or 5- pyrimidinylcarbonyl, 2-,4- or 5-pyrimidinyl-N-oxide-carbonyl, pyrazinylcarbonyl, 2-,3- or 4-piperidinylcarbonyl, piperazinylcarbonyl, 3H-indol-2 or 3-ylcarbonyl, 2-,3-or 4-pyranylcarbonyl, 2-,3- or 4-thiopyranylcarbonyl, 3-,4-,5-,6-,7- or 8-quinolylcarbonyl, pyrido[2,3-d]pyrimidinylcarbonyl, 1,5-, 1,6-, 1,7-, 1,8-, 2,6- or 2,7-naphthyridinylcarbonyl, thieno[2,3-d]pyridylcarbonyl, pyrazinoquinolylcarbonyl, chromenylcarbonyl, 2-pyrrolylacetyl, 3-imidazolylacetyl and 5-isoxazolylacetyl, W is O or S, R₁ and R₂ each are a straight chain, branched chain or cyclic alkyl group containing 1 to 6 carbon atoms, a straight chain or branched chain alkoxy group containing 1 to 6 carbon atoms, or a halogen, and Z is CH, or a salt thereof.

14. A compound of claim 13 which is N-(2-chloro-6-methoxyimidazo[1,2-b]pyridazin-3-ylsulfonyl)-N'-(4,6-dimethoxy-2-pyrimidinyl)urea.

15. A compound of claim 1 which is N-(2-chloro-6-methylthio imidazo[1,2-b]pyridazin-3-ylsulfonyl)-N'-(4,6-dimethoxy-2-pyrimidinyl)urea.

16. A compound of claim 13 in which the condensed heterocyclic ring of Q is imidazo[1,2-b]pyridazine

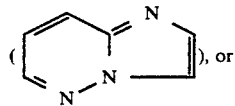, or or pyrazolo[1,5-a]pyrimidine

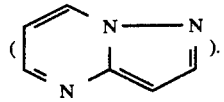.

17. A compound of claim 13 in which Q is

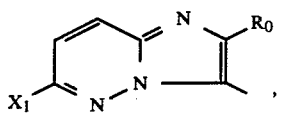, wherein R₀ is hydrogen, a lower alkyl group which may be substituted by a halogen, a lower alkylthio group, a lower alkylsulfonyl group, a lower alkoxycarbonyl group or a halogen, and X₁ is hydrogen, a lower alkoxy group or a lower alkylthio group.

18. A herbicidal composition comprising as an active ingredient an effective amount of a compound or salt of claim 13 and a carrier therefor suitable for herbicidal use of the composition.

19. A herbicidal composition of claim 18 in which the compound of the formula (I) is N-(2-chloro-6-methoxyimidazo[1,2-b]pyridazin-3-ylsulfonyl)-N'-(4,6-dimethoxy-2-pyrimidinyl) urea or N-(2-chloro-6-methylthioimidazo[1,2-b]pyridazin-3-ylsulfonyl)-N'-(4,6-dimethoxy-2-pyrimidinyl)urea.

20. A method of killing weeds in a paddy field which comprises applying a herbicidally effective amount of a compound or salt of claim 13 to the paddy field.

21. A compound of claim 1 which is N-(2-ethylsulfonylimidazo[1,2-a]pyridin-3-ylsulfonyl)-N'-(4,6-dimethoxy-2-pyrimidinyl)urea or a salt thereof.

22. A compound of claim 1 which is N-(6-ethylsulfonylimidazo[2,1-b]thiazol-5-ylsulfonyl)-N'(4,6-dimethoxy-2-pyrimidinyl)urea or a salt thereof.

* * * * *